(12) United States Patent
Shi et al.

(10) Patent No.: US 7,741,086 B2
(45) Date of Patent: Jun. 22, 2010

(54) HISTONE DEMETHYLATION MEDIATED BY THE NUCLEAR AMINE OXIDASE HOMOLOG LSD1

(75) Inventors: Yang Shi, Brookline, MA (US); Yujiang Shi, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 4 days.

(21) Appl. No.: 11/721,789

(22) PCT Filed: Dec. 16, 2005

(86) PCT No.: PCT/US2005/045987

§ 371 (c)(1),
(2), (4) Date: Feb. 19, 2009

(87) PCT Pub. No.: WO2006/071608

PCT Pub. Date: Jul. 6, 2006

(65) Prior Publication Data

US 2009/0170796 A1 Jul. 2, 2009

Related U.S. Application Data

(60) Provisional application No. 60/636,095, filed on Dec. 16, 2004.

(51) Int. Cl.
*C12N 9/00* (2006.01)
*C12N 15/09* (2006.01)

(52) U.S. Cl. ................ 435/183; 435/69.2; 435/199; 536/23.2

(58) Field of Classification Search .......... 435/69.2, 435/183, 199; 536/23.2
See application file for complete search history.

(56) References Cited

U.S. PATENT DOCUMENTS

2003/0083283 A1  5/2003  Bennett et al.

FOREIGN PATENT DOCUMENTS

| EP | 1 693 383 | 8/2006 |
|---|---|---|
| EP | 1 704 859 | 9/2006 |
| WO | WO-2006/087206 | 8/2006 |

OTHER PUBLICATIONS

Bannister et al., "Histone Methylation: Dynamic or Static?," Cell, 109:801-806 (2002).
Chosed et al., "A Two-Way Street: LSD1 Regulates Chromatin Boundary Formation in *S. pombe* and *Drosophila*," Molecular Cell, 26:160-162 (2007).
Di Stefano et al., "Mutation of *Drosophila Lsd1* Disrupts H3-K4 Methylation, Resulting in Tissue-Specific Defects during Development," Current Biology, 17:808-812 (2007).
Fang et al., "Expression of Dnmt1, demethylase, MeCP2 and methylation of tumor-related genes in human gastric cancer," World J Gastroenterol., 10(23):3394-3398 (2004).
Garcia-Bassets et al., "Histone Methylation-Dependent Mechanisms Impose Ligand Dependency for Gene Activation by Nuclear Receptors," Cell, 128:505-518 (2007).
Hakimi et al., "A Candidate X-linked Mental Retardation Gene Is a Component of a New Family of Histone Deacetylase-containing Complexes," J Bio Chemistry, 278(9):7234-7239 (2003).
Hakimi et al., "A core-BRAF35 complex containing histone deacetylase mediates repression of neuronal-specific genes," PNAS, 99(11)7420-7425 (2002).
Huang, Shi "Histone methyltransferases, diet nturients and tumour suppressors," Nature Reviews, 2:469-476 (2002).
Huang et al., "Inhibition of lysine-specific demethylase 1 by polyamine analogues results in reexpression of aberrantly silenced genes," PNAS, 104(19):8023-8023 (2007).
Humphrey et al., "Stable Histone Deacetylase Complexes Distinguished by the Presence of SANT Domain Proteins CoREST/kiaa0071 and Mta-L1," J Bio Chemistry, 276(9):6817-6824 (2001).
Isogai et al., "*Homo sapiens*cDNA FLJ43328 fis, clone NT2RI3004510," Unpublished (2003), Abstract Only.
Kondo et al., "Epigenetic changes in colorectal cancer," Cancer and Metastasis Reviews, 23:29-39 (2004).
Kubicek et al., "A Crack in Histone Lysine Methylation," Cell, 119:903-906 (2004).
Lan et al., "*S.pombe* LSD1 Homologs Regulate heterochromatin Propagation and Euchromatic Gene Transcription," Molecular Cell, 26:1-13 (2007).
Lan et al., "A histone H3 lysine 27 demethylase regulates animal posterior development," Nature, 449:689-694 (2007).
Lan et al., Supplementary Information of Nature manuscript 2007-05-05498A, 1-13.
Lee et al., "An essential role for CoRest in nucleosomal histone 3 lysine 4 demethylation," Nature, 437:432-435 (2005).
Metzger et al., "LSD1 demethylates repressive histone marks to promote androgen-receptor-dependent transcription," Nature, 437:436-439 (2005).
Nagase et al., "Prediction of the coding sequences of unidentified human genes," DNA Res. 5(1):31-39 (1998) Abstract Only.
Paik et al., "Enzymatic Demethylation of Calf Thymus Histones," Biochemical and Biophysical Research Communications, 51(3):781-788 (1973).

(Continued)

*Primary Examiner*—Tekchand Saidha
(74) *Attorney, Agent, or Firm*—Foley Hoag LLP

(57) ABSTRACT

LSD1, a homolog of nuclear amine oxidases, functions as a histone demethylase and transcriptional co-repressor. LSD1 specifically demethylates histone H3 lysine 4, which is linked to active transcription. Lysine demethylation occurs via an oxidation reaction that generates formaldehyde. Importantly, RNAi inhibition of LSD1 causes an increase in H3 lysine 4 methylation and concomitant de-repression of target genes, suggesting that LSD1 represses transcription via histone demethylation. The results thus identify a histone demethylase conserved from *S. pombe* to human and reveal dynamic regulation of histone methylation by both histone methylases and demethylases.

18 Claims, 3 Drawing Sheets

OTHER PUBLICATIONS

Shi et al., "Histone Demethylation Mediated by the Nuclear Amine Oxidase Homolog LSD1," Cell, 119:941-953 (2004).
Shi, "Taking LSD1 to a New High," Cell 654-658 (2005).
Shi et al., "Regulation of LSD1 Histone Demethylase Activity by Its Associated Factors," Molecular Cell, 19:1-8 (2005).
Shi et al., "Metabolic Enzymes and Coenzymes in Transcription—a Direct Link Between Metabolism and Transcription?," Trends in Genetics 20(9):445-452 (2004).
Tsukada et al., "Histone Demethylation by a Family of JmjC Domain-Containing Proteins," Nature (2006) 439:811 Epub Dec. 18, 2005.
Wang et al., "Human PAD4 Regulates Histone Arginine Methylation Levels via Demethylimination," Science, 306:279-283 (2004).
Yamane et al., "JHDM2A, a JmjC-Containing H3K9 Demethylase, Facilitates Transcription Activation by Androgen Receptor," Cell 125 (2006).
International Search Report for PCT/US2005/045987 mailed on Aug. 11, 2006.

HISTONE DEMETHYLATION MEDIATED BY THE NUCLEAR AMINE OXIDASE HOMOLOG LSD1

CROSS-REFERENCE TO RELATED APPLICATIONS

This application is the National Stage of International Application No. PCT/US2005/045987, filed Dec. 16, 2005, which claims the benefit of Provisional Application No. 60/636,095, filed Dec. 16, 2004, both of which are specifically incorporated by reference herein.

GOVERNMENT INTEREST

This invention was made using funds from grant GM071004 from the U.S. National Institutes of Health. The U.S. government therefore retains certain rights in the invention.

TECHNICAL FIELD OF THE INVENTION

This invention is related to the area of gene regulation. In particular, it relates to the area of modification of chromosome structure as a means of regulating transcription. This modification importantly impacts disease processes as well as normal physiology and development.

BACKGROUND OF THE INVENTION

The histone N-terminal tails are subjected to multiple covalent modifications that affect chromatin structure and consequently transcription. One of the best-characterized modifications is acetylation, which is controlled by both histone acetyltransferases (HATs) and deacetylases (HDACs) suggesting that acetylation regulation is a dynamic process (Kouzarides, 2000). More recently, histone methylation has also emerged as a form of posttranslational modification that significantly impacts chromatin structure (Rice and Allis, 2001; Zhang and Reinberg, 2001). Unlike histone acetylation, which takes places only on lysine (K), methylation occurs on both lysine and arginine (R). While acetylation is generally correlated with active transcription (Roth et al., 2001), histone methylation is linked to both transcriptional activation and repression (Zhang and Reinberg, 2001). For instance, histone H3 K9 (H3-K9) methylation is associated with heterochromatin formation (Nakayama et al., 2001; Peters et al., 2002; Rea et al., 2000) and also euchromatic gene repression (Nielsen et al., 2001; Shi et al., 2003). In the case of heterochromatin assembly, H3-K9 is first methylated by Suv39H, and the methylated K9 is then recognized and bound by the chromodomain protein HP1 (Bannister et al., 2001; Lachner et al., 2001; Nakayama et al., 2001). The Suv39H-HP1 methylation system is proposed to be responsible for heterochromatin propagation. In contrast, methylation of histone H3 K4 (H3-K4) is linked to active transcription (Liang et al., 2004; Litt et al., 2001; Noma et al., 2001; Santos-Rosa et al., 2002; Schneider et al., 2004), as is methylation of arginine residues of histone H3 and H4 (Zhang and Reinberg, 2001). Mechanisms that underlie methylation-dependent transcriptional activation are not completely understood, although H3-K4-specific methylases have recently been shown to associate with RNA polymerase II (Hamamoto et al., 2004; Ng et al., 2003b).

While histone acetylation is dynamically regulated by HATs and HDACs, histone methylation has been considered a "permanent" modification. At least two models are currently being considered to explain the turnover of methyl groups on histones. The first one suggests that a cell may remove histone methylation by clipping the histone tail (Allis et al., 1980) or by replacing the methylated histone with a variant histone in the case of methyl group turnover at H3-K9 (Ahmad and Henikoff, 2002; Briggs et al., 2001; Johnson et al., 2004). However, this mechanism would not allow for dynamic regulation of histone methylation and the plasticity that may be essential for gene transcription regulation in some biological processes. The second model proposes the existence of histone demethylases that function to remove the methyl groups from lysine and arginine, which would make dynamic regulation possible. Recently, a human peptidyl arginine deiminase, PAD14/PAD4, has been shown to antagonize methylation on the arginine residues by converting arginine to citrulline, (Cuthbert et al., 2004; Wang et al., 2004). PAD14/PAD4 catalyzes the deimination reaction irrespective of whether the arginine residue is methylated or not. These findings suggest that histone methylation can be dynamically regulated through the opposing actions of histone methylases and enzymes such as PAD14/PAD4. However, since PAD14/PAD4 catalyzes deimination but not demethylation, it remains unclear whether bona fide histone demethylases exist. The search for histone demethylases began in the 1960s when Paik and colleagues first reported an enzyme that can demethylate free mono- and di-N-methyllysine (Kim et al., 1964). Subsequently, the same investigators partially purified an activity that can demethylate histones (Paik and Kim, 1973; Paik and Kim, 1974). These early studies suggested the possibility that histone demethylases may exist but the molecular identity of these putative histone demethylases have remained elusive for the past four decades.

Classical amine oxidases play important roles in metabolism and their substrates range from small molecules (e.g., spermine and spermidine) to proteins. More recently, amine oxidases have also been proposed to function as histone demethylases via an oxidation reaction that removes methyl groups from lysine or arginine residues of histones (Bannister et al., 2002). KIAA0601 encodes a protein that shares significant sequence homology with FAD-dependent amine oxidases (Humphrey et al., 2001; Shi et al., 2003). We identified KIAA0601/NPAO as a component of the CtBP co-repressor complex (Shi et al., 2003), and it has also been found in a number of other co-repressor complexes, including NRD (Tong et al., 1998), Co-REST (You et al., 2001), and subsets of the HDAC complexes (Hakimi et al., 2002; Hakimi et al., 2003; Humphrey et al., 2001). Recent studies of the *C. elegans* homolog, SPR-5, provided genetic evidence for a role in transcriptional repression (Eimer et al., 2003; Jarriault and Greenwald, 2002). However, its exact role in transcriptional regulation has been unclear.

There is a continuing need in the art to identify the components of the transcription regulatory system so that they can be manipulated to treat diseases that involve aberrations of the system.

SUMMARY OF THE INVENTION

In one embodiment of the invention a method is provided for monitoring eukaryotic histone demethylase activity. An eukaryotic histone demethylase protein is contacted with a histone peptide. The histone peptide is lysine- or arginine-methylated. The methylation status of the histone peptide is determined.

A second embodiment of the invention provides a method of screening for modulators of eukaryotic histone demethylase activity. An eukaryotic histone demethylase protein and a histone peptide are contacted in the presence and in the absence of a test substance. The histone peptide is lysine-methylated. The methylation status of the histone peptide is determined. A test substance is identified as an inhibitor of eukaryotic histone demethylase activity if more methylated lysine is found in the presence than in the absence of the test substance. A test substance is identified as an enhancer of eukaryotic histone demethylase protein activity if less methylated lysine is found in the presence than in the absence of the test substance.

A third embodiment of the invention provides a method of up-regulating methylated histone-activated genes. An RNAi for an eukaryotic histone demethylase is administered to cells in an amount sufficient to inhibit expression of the eukaryotic histone demethylase.

A fourth embodiment of the invention provides a method of up-regulating methylated histone-activated genes. An antisense RNA for an eukaryotic histone demethylase is administered to cells in an amount sufficient to inhibit expression of the eukaryotic histone demethylase.

A fifth embodiment of the invention provides a method of up-regulating methylated histone-activated genes. An antisense construct for an eukaryotic histone demethylase is administered to cells in an amount sufficient to inhibit expression of the eukaryotic histone demethylase.

A sixth embodiment of the invention provides a method of down-regulating methylated histone-activated genes. An expression vector encoding an eukaryotic histone demethylase is administered to cells in an amount sufficient to increase expression of the eukaryotic histone demethylase in the cell.

A seventh embodiment of the invention provides a method of screening for modulators of LSD1 activity. A LSD1 protein and a histone peptide are contacted in the presence and in the absence of a test substance. The histone peptide comprises at least six contiguous amino acid residues of histone H3 which include lysine residue 4, and the lysine residue 4 is mono- or di-methylated. The methylation status of the histone peptide is determined. A test substance is identified as an inhibitor of LSD1 activity if more methylated lysine is found in the presence than in the absence of the test substance. A test substance is identified as an enhancer of LSD1 activity if less methylated lysine residue 4 is found in the presence than in the absence of the test substance.

An eighth embodiment of the invention provides a method of up-regulating methyl lysine 4 histone 3-activated genes. An RNAi for LSD1 is administered to cells in an amount sufficient to inhibit expression of the LSD1 histone demethylase.

A ninth embodiment of the invention provides a method of up-regulating methyl lysine 4 histone 3-activated genes. An antisense RNA for LSD1 histone demethylase is administered to cells in an amount sufficient to inhibit expression of the LSD1 histone demethylase.

A tenth embodiment of the invention provides a method of up-regulating methyl lysine 4 histone 3-activated genes. An antisense construct for an LSD1 histone demethylase is administered to cells in an amount sufficient to inhibit expression of the LSD1 histone demethylase.

An eleventh embodiment of the invention provides a method of down-regulating methyl lysine 4 histone 3-activated genes. An expression vector encoding LSD1 histone demethylase is administered to cells in an amount sufficient to increase expression of the eukaryotic histone demethylase in the cell.

A twelfth embodiment of the invention provides a method of up-regulating methylated histone-repressed genes. An inhibitor for an eukaryotic histone demethylase is administered to cells in an amount sufficient to inhibit activity of the eukaryotic histone demethylase.

A thirteenth embodiment of the invention provides a method of down-regulating methylated histone-activated genes. An enhancer of an eukaryotic histone demethylase is administered to cells in an amount sufficient to increase activity of the eukaryotic histone demethylase. Other embodiments are further described in the claims and specification.

Also provided herein are methods for identifying an agent that modulates the interaction between a histone demethylase protein and a CoREST protein. A method may comprise contacting a histone demethylase reagent and a CoREST reagent in the presence of a test agent; and (ii) determining the level of interaction between the histone demethylase reagent and the CoREST reagent, wherein a different level of interaction between the histone demethylase reagent and the CoREST reagent in the presence of the test agent relative to the absence of the test agent indicates that the test agent is an agent that modulates the interaction between a histone demethylase protein and a CoREST protein. A method may further comprise at least one other component of a histone demethylase transcription complex. A method may further comprise determining the effect of the test agent on a biological activity of the histone demethylase, e.g., by a method comprising contacting a histone demethylase reagent and a CoREST reagent with the test agent and determining the biological activity of the histone demethylase reagent, wherein a different activity of the histone demethylase reagent in the presence of the test agent relative to the absence of the test agent indicates that the test agent is an agent that modulates the biological activity of a histone demethylase.

Further provided are methods for identifying an agent that modulates the biological activity of a histone demethylase. A method may comprise (i) contacting a histone demethylase reagent with a CoREST reagent in the presence of a test agent; and (ii) determining the biological activity of the histone demethylase reagent, wherein a different activity of the histone demethylase reagent in the presence of the test agent relative to the absence of the test agent indicates that the test agent is an agent that modulates the biological activity of a histone demethylase. The biological activity of the histone demethylase reagent is demethylase activity or amine oxidase activity. The CoREST reagent may comprise at least about amino acids 293 to 381 at least about amino acids 293 to 482 of human CoREST.

A method for identifying an agent that modulates the interaction between a histone demethylase protein and a BHC80 protein may comprise contacting a histone demethylase reagent and a BHC80 reagent in the presence of a test agent; and (ii) determining the level of interaction between the histone demethylase reagent and the BHC80 reagent, wherein a different level of interaction between the histone demethylase reagent and the BHC80 reagent in the presence of the test agent relative to the absence of the test agent indicates that the test agent is an agent that modulates the interaction between a histone demethylase protein and a BHC80 protein. A method may further comprise at least one other component of a histone demethylase transcription complex. A method may further comprise determining the effect of the test agent on a biological activity of the histone demethylase, e.g., by a method comprising contacting a histone demethylase reagent and a HDC80 reagent with the test agent and determining the biological activity of the histone demethylase reagent, wherein a different activity of the histone demethylase reagent in the presence of the test agent relative to the absence of the test agent indicates that the test agent is an agent that modulates the biological activity of a histone demethylase.

A method for identifying an agent that modulates the biological activity of a histone demethylase may comprise (i) contacting a histone demethylase reagent with a HDC80 reagent in the presence of a test agent; and (ii) determining the biological activity of the histone demethylase reagent, wherein a different activity of the histone demethylase reagent in the presence of the test agent relative to the absence of the test agent indicates that the test agent is an agent that modulates the biological activity of a histone demethylase. The biological activity of the histone demethylase reagent may be demethylase activity or amine oxidase activity.

Also provided herein are molecular complexes or compositions, e.g., pharmaceutical compositions, comprising a histone demethylase reagent and a CoREST reagent; and/or a BHC80 reagent.

A method for repressing the transcription of a methylated histone activated gene in a cell may comprise contacting the cell with, or administering into the cell, an agent that increases the protein or activity level of a histone demethylase in the cell. The agent may be a histone demethylase protein or functional homolog thereof. The agent may also be a nucleic acid encoding a histone demethylase protein or functional homolog thereof. The agent may be an agent that increases the level of protein or activity of CoREST. The agent may be a CoREST protein or functional homolog thereof. The agent may be a nucleic acid encoding a CoREST protein or functional homolog thereof. The agent may be an agent that stimulates the interaction between a histone demethylase and CoREST. The agent may be an agent that decreases the level of protein or activity of BHC80, e.g., a BHC80 siRNA, or an agent that inhibits the interaction between a histone demethylase and BHC80. The method may further comprise contacting the cell with, or administering into the cell, a second agent that increases the level or protein or activity of a histone deacetylase (HDAC). The second agent may be an HDAC protein or a functional homolog thereof. The second agent may be a nucleic acid encoding an HDAC protein or a functional homolog thereof.

Other exemplary methods provided herein include methods for increasing the transcription of a methylated histone activated gene in a cell, comprising contacting the cell with an agent that decreases the protein or activity level of a histone demethylase in the cell. The agent may be a histone demethylase siRNA; an agent that decreases the protein or activity level of CoREST in the cell, such as a CoREST siRNA; an agent that inhibits the interaction between a histone demethylase and CoREST; an agent that increases the level of protein or activity of BHC80, such as a BHC80 protein or functional homolog thereof or a nucleic acid encoding a BHC80 protein or functional homolog thereof; or an agent that stimulates the interaction between a histone demethylase and BHC80. A method may further comprise contacting the cell with, or administering into the cell, a second agent that decreases the level or activity of an HDAC.

A method for treating or preventing a disease associated with the abnormal expression of a methylated histone activated gene in a subject may comprise administering to the subject a therapeutically effective amount of an agent that modulates the level of protein or activity of a histone demethylase. The disease may be a hyperproliferative disease, e.g. cancer, and the agent is an agent that increases the level of protein or activity of a histone demethylase. The method may further comprise administering to the subject a therapeutically effective amount of a second agent that increases the level of protein or activity of a histone deacetylase. The first and second agents may be administered to the subject by intratumoral injection, perfusion of a target tissue through its vasculature or by direct injection to a target tissue.

These and other embodiments which will be apparent to those of skill in the art upon reading the specification provide the art with reagents and methods for drug screening and therapy relating to histone methylation, neurological diseases and cancer.

BRIEF DESCRIPTION OF THE DRAWINGS

FIG. 1A. Diagram of the LSD1-like amine oxidase family members in different species. The deduced amino acid sequences are retrieved from NCBI GenBank and analyzed by the NCBI Conserved Domain Search Program. The SWIRM, amine oxidase domains and FAD binding motif are drawn proportionally. Some family members contain a spacer region in their amine oxidase domain, which is shown by white-red stripes. Additionally, the *S. pombe* protein SPAC23E2.02 contains a HMG domain and *A. thaliana* protein AAF19542 has an EFh and a copper amine oxidase domain. FIG. 1B. Two subfamilies of LSD1-like proteins. The amine oxidase domains of these proteins are classified into two subfamilies based on ClustalW-aligned phylogenetic tree. A noted difference is that the LSD1 subfamily (7 members) contains the spacer region but not the AOF1 subfamily (6 members) (except NP_193364.1). FIG. 1C. Diagrams of G4LSD1 and the C-terminal deletion mutant G4LSD1ΔC. AO: amine oxidase.

DETAILED DESCRIPTION OF THE INVENTION

Figure 1:
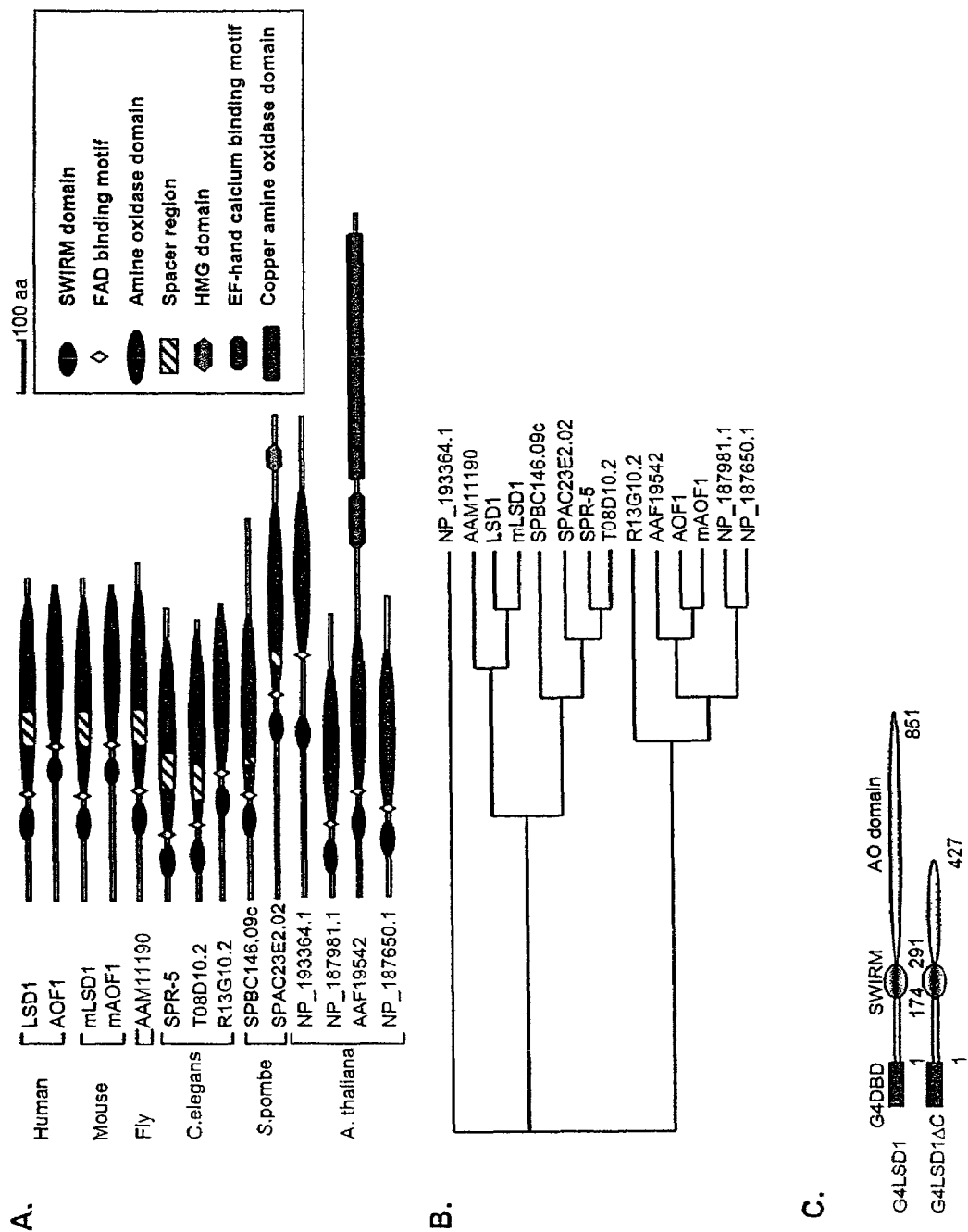
FIGS. 1A-1C. LSD1 is a transcriptional co-repressor and is evolutionarily conserved.

It is a discovery of the present inventors that LSD1 functions as a transcriptional co-repressor that participates in the silencing of endogenous neuron-specific genes. Significantly, RNAi knock down of LSD1 results in an increase in histone H3-K4 methylation and a concomitant de-repression of the target genes. These findings indicate that LSD1 represses transcription by demethylating histone H3 at K4, whose methylation is linked to active transcription (Liang et al., 2004; Litt et al., 2001; Noma et al., 2001; Santos-Rosa et al., 2002; Schneider et al., 2004). Since LSD1 and its related proteins are present from *S. pombe* to mammals, demethylation is likely an evolutionarily conserved function for this family of proteins. The identification of LSD1 as a histone demethylase indicates that histone methylation, like histone acetylation, is a dynamic process and is subject to regulation by both methylases and demethylases.

It has also been shown herein that the activity of LSD1 is modulated by its interaction with other proteins, such as CoREST and BHC80, as well as by the acetylation status of histones that are bound to the promoter of LSD1 target genes.

Exemplary Methods and Composition

Provided herein are methods for modulating the expression of genes that are regulated by methylation/demethylation of a transcriptional regulator protein, such as a histone ("demethylase target gene"). Some genes are upregulated by methylation of a histone ("methylated histone-activated genes"), whereas other genes are downregulated by methylation of a histone ("methylated histone-repressed gene"). The following genes are upregulated by the methylation of histone H3 at the lysine K4: M4 AchR, SCN1A, SCN2A, SCN3A, and p57. Other target genes include those containing a REST-responsive repressor element 1 (RE1). These genes are repressed by a demethylase, such as LSD1. Accordingly, the expression of these methylated histone-activated genes can be repressed by the presence of LSD1 and activated (or derepressed) by removing LSD1, such as by using an LSD1 siRNA or antisense or dominant negative mutant. Similarly, methylated histone-activated genes can be repressed by the presence of CoREST and activated (or derepressed) by removing CoREST, such as by using a CoREST siRNA or antisense or dominant negative mutant. In addition, methylated histone-activated genes can be repressed by removing BHC80, such as by using a BHC80 siRNA or antisense or dominant negative mutant, and activated by the presence of BHC80. The methylated histone-activated genes may also be modulated by modulating the expression of one or more of LSD1, CoREST and BHC80.

Genes that are downregulated by the methylation of histone H3 include those that are regulated by the androgen receptor (Metzger et al. (2005) Nature 437:436), such as those containing an androgen receptor element (ARE) in their promoter. Exemplary genes that are regulated by the androgen receptor include: prostate specific antigen isoform 1 (PSA)(NP_001639); Synaptotagmin-like 4 (SYTL4) (CAI42004); nerve growth factor receptor associated protein 1(NGFRAP1) (CAI41523); 6-phosphofructo-2-kinase/fructose-2,6-biphosphatase 1 (PFKFB1) (NP_002616); fatty acid synthase (FAS) (NP_004095); and Proteinase-activated receptor 1 precursor (PAR-1) (P25116). Genes regulated by the androgen receptor may be activated by a demethylase, such as LSD1. Accordingly, the expression of these methylated histone-repressed genes can be activated (or derepressed) by the presence of LSD1 and repressed by removing LSD1, such as by using an LSD1 siRNA or antisense or dominant negative mutant. Expression of methylated histone-repressed genes can also be activated (or derepressed) by the presence of CoREST and repressed by removing CoREST, such as by using a CoREST siRNA or antisense or dominant negative mutant. In addition, methylated histone-repressed genes can be activated by removing BHC80, such as by using a BHC80 siRNA or antisense or dominant negative mutant, and repressed by the presence of BHC80. The methylated histone-repressed genes may also be modulated by modulating the expression of one or more of LSD1, CoREST and BHC80.

The following Table I summarizes how gene expression of methylated histone-repressed and histone-activated genes can be modulated:

| Gene | modulation | LSD1 | CoREST | BHC80 |
|---|---|---|---|---|
| methylated histone-repressed | activation | increase | increase | decrease |
| | repression | decrease | decrease | increase |
| methylated histone-activated | activation | decrease | decrease | increase |
| | repression | increase | increase | decrease |

In Table I, "increase" of a protein refers to increasing its level of protein or activity. Increasing the level of protein or activity of a particular protein in a cell may be achieved by contacting the cell with, or administering into the cell: the protein or a functional homolog thereof; a nucleic acid (e.g., an expression vector) encoding the protein or a functional homolog thereof; an agent that upregulates the level of expression of the gene encoding the protein; or an agent that upregulates the activity of the protein, such as a cofactor. Increasing the level of protein or activity of a protein may be by a factor of at least about 50%, 2 fold, 5 fold, 10 fold, 30 fold, 50 fold or 100 fold.

In Table I, "decrease" of a protein refers to decreasing its level of protein or activity. Decreasing the level of protein or activity of a particular protein in a cell may be achieved by contacting the cell with, or administering into the cell: an siRNA; an antisense; a ribozyme; a triplex nucleic acid; a dominant negative mutant of the protein; a substrate mimetic; an agent that down-regulates the expression of the gene encoding the protein; or an agent that decreases the activity of the protein. Decreasing the level of protein or activity of a protein may be by a factor of at least about 50%, 2 fold, 5 fold, 10 fold, 30 fold, 50 fold or 100 fold.

Eukaryotic histone demethylase enzymes, according to the present invention are those eukaryotic proteins which have a SWIRM domain, a FAD binding motif, and an amine oxidase domain. The presence of these domains can be determined using tools available in the art including NCBI GenBank and NCBI Conserved Domain Search Program. Particular exemplary members of this class of enzymes are shown in FIG. 1A.

A histone demethylase may be an enzyme that demethylates the residue K4 on histone H3 (a "H3-K4 demethylase"). An exemplary H3-K4 demethylase is LSD1, which is also referred to as "FAD-binding protein BRAF35-HDAC complex, 110 kDa subunit" ("BHC110"), "KIAA0601", and "amine oxidase (flavin containing) domain 2" ("AOF2"). The protein exists in two isoforms: variant (1) represents the longer transcript and encodes the longer isoform (a); and variant (2) lacks two alternate in-frame exons, compared to variant 1, resulting in a shorter protein (isoform b), compared to isoform a.

The following Table (Table 2) provides references for the nucleotide and amino acid sequences of the human LSD1 proteins:

| isoform | nucleic acid | SEQ ID NO | protein | SEQ ID NO |
|---|---|---|---|---|
| a | NM_015013.2 | 28 | NP_001009999 (876 aas) | 29 |
| b | NM_015013.2 | 30 | NP_055828.2 (852 aas) | 31 |

TABLE 3

Approximate location of conserved domains in human LSD1 proteins:

| isoform | amino oxidase domain | SWIRM domain | FAD binding motif |
|---|---|---|---|
| a | aas 548-849; 311-450 | aas 195-284 | aas 300-359 |
| b | aas 524-825; 291-426 | aas 175-264 | aas 280-339 |

The amino acid sequence of the FAD binding motif is KVIIIGSGVSGLAAARQLQSFGMDVTL-LEARDRVGGRVATFRKGNYVADLGAMVV TGLGG (SEQ ID NO: 43).

Another demethylase is AOF1 or amine oxidase (flavin containing) domain 1 protein. The amino acid and nucleotide sequences of human AOF1 are set forth in GenBank Accession numbers NM_153042 (SEQ ID NO: 36) and NP_694587 (SEQ ID NO: 37) and in SEQ ID NOs: 26 and 27, respectively. An NAD/FAD-dependent oxidoreductase domain is located at about amino acids 268-588 and a flaving containing amine oxidoreductase domain located at about amino acids 319-587 and 267-322 of SEQ ID NO: 37.

"CoREST" is a corepressor of RE1-silencing transcription factor (REST) and is also referred to as "REST corepressor 1" and "RCOR1". The nucleotide and amino acid sequences of human CoREST are set forth in GenBank Accession Nos. NM_015156.1 and NP_055971.1 (482 amino acids), which correspond to SEQ ID NOs: 32 and 33, respectively. The human protein contains the following conserved domains: SANT1 (about amino acids 190-293), SANT2 (about amino acids 381-450) and ELM (about amino acids 105-182).

"BHC80" is also referred to as "PHD finger protein 21A" ("PHF21A"), "BM-006" and "KIAA1696," and is a component of the "BRAF35/HDAC2 complex" or "BRAF35/HDAC2 complex (80 kDa)." The nucleotide and amino acid sequences of the human BHC80 are set forth in GenBank Accession Nos. NM_016621.2 and NP_057705.2, which correspond to SEQ ID NOs: 34 and 35, respectively. The human protein contains a PHD zinc finger domain at about amino acids 444-487.

BHC is a multiprotein complex consisting of two enzymatic activities: a histone deacetylase (HDAC 1 or 2) and LSD1.

Human histone H3 is encoded by the nucleotide sequence set forth in GenBank Accession No. NM_003493.2 and has the amino acid sequence set forth in GenBank Accession No. NP_003484.1.

A homolog of a protein of interest, such as LSD1, CoREST or BHC80, includes proteins comprising or consisting of an amino acid sequence that has at least about 70%, 80%, 90%, 95%, 98% or 99% identity with the amino acid sequence of the protein described herein, such as SEQ ID NOs: 23, 26, 29, 31, 33, 35 and 37. A homolog may also be a protein that is encoded by a nucleic acid that has at least about 70%, 80%, 90%, 95%, 98% or 99% identity with a nucleotide sequence described herein, such as SEQ ID NOs: 24, 27, 28, 30, 32, 34 and 36 or the coding sequence thereof. A homolog may also be a protein that is encoded by a nucleic acid that hybridizes, e.g., under stringent hybridization conditions, to a nucleic acid consisting of a nucleotide sequence described herein, e.g., SEQ ID NOs: 24, 27, 28, 30, 32, 34 and 36, or the coding sequence thereof.

For example, homologs may be encoded by nucleic acids that hybridize under high stringency conditions of 0.2 to 1×SSC at 65° C. followed by a wash at 0.2×SSC at 65° C. to a nucleic acid consisting of a sequence described herein. Nucleic acids that hybridize under low stringency conditions of 6×SSC at room temperature followed by a wash at 2×SSC at room temperature to nucleic acid consisting of a sequence described herein or a portion thereof can be used. Other hybridization conditions include 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays," Elsevier, New York provide a basic guide to nucleic acid hybridization.

Homologs of proteins described herein, such as LSD1, CoREST and BHC80 may also be analogs, e.g., that differ from the naturally occurring protein, e.g. a protein having an amino acid sequence set forth as SEQ ID NO: 23, 26, 29, 31, 33, 35 and 37, by conservative amino acid sequence differences or by modifications which do not affect sequence, or by both. Analogs can differ from naturally occurring proteins by conservative amino acid sequence differences or by modifications which do not affect sequence, or by both. Any number of procedures may be used for the generation of mutant, derivative or variant forms of a protein of interest using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

For example, conservative amino acid changes may be made, which although they alter the primary sequence of the protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine (in positions other than proteolytic enzyme recognition sites); phenylalanine, tyrosine.

Homologs of a protein of interest also includes portions thereof, such as portions comprising one or more conserved domains, such as those described herein.

A "functional homolog" of a protein of interest refers to a homolog of the protein having at least one biological activity of the protein. For example, a functional homolog of LSD1 may be a protein having an amine oxidase activity, a demethylase activity, the ability to bind to another protein, such as CoREST or BHC80 or a protein from a nucleosome, or other biological activities, such as those described herein.

A functional homolog of LSD1 may be a portion of the wild type LSD1 protein including one or more of the conserved domains. A functional homolog of LSD1 may comprise at least a portion of the amino oxidase domain, the SWIRM domain and/or the FAD binding motif. Exemplary functional homologs of LSD1 isoform a include polypeptides comprising from about amino acid 195, 190, 175, 150 or 100 to about amino acid 849, 850, 860, 870 or 876 of SEQ ID NO: 29. Exemplary functional homologs of LSD1 isoform b include polypeptides comprising from about amino acid 175, 174, 170, 150 or 100 to about amino acid 825, 830, 840, 850, 851 or 852 of SEQ ID NO: 31. Functional LSD1 homologs may also include those comprising an amino acid sequence from about amino acid 311, 310, 300 or 250 to about amino acid 849, 850, 860, 870 or 876 of SEQ ID NO: 29 (LSD1 isoform a) and those comprising an amino acid sequence from about amino acid 291, 290, 280, 270 or 250 to about amino acid 825, 830, 840, 850, 851 or 852 of SEQ ID NO: 31 (homologs comprising the amino oxidase domain). Other LSD1 homologs that may have a biological activity include those comprising the SWIRM domain, e.g., about amino acid 195, 190, 175, 150 or 100 to about amino acid 284, 285, 290 or 300 of SEQ ID NO: 29 (LSD1 isoform a) or about amino acid 175, 174, 170, 150 or 100 to about amino acid 264, 265, 270, 280, 290 or 300 of SEQ ID NO: 31 (LSD1 isoform b).

Functional homologs of AOF1 include an oxidoreductase domain, e.g., the NAD/FAD-dependent oxidoreductase domain or the flavin containing amine oxidoreductase domain. Exemplary functional homologs of AOF1 include those comprising from about amino acid 268, 260, 250 or 200 to about amino acid 588, 590, 595 or 600 of SEQ ID NO: 37.

Functional homologs of CoREST include the ELM, SANT1 and/or SANT2 domains. Exemplary functional homologs of CoREST include those comprising about from about amino acid 293, 290, 280, 270, 260 or 250 to about amino acid 480 or 482 of SEQ ID NO: 33. Other CoREST functional homologs may comprise from about amino acid 293, 290, 280, 270, 260 or 250 to about amino acid 381, 385, 390 or 300 of SEQ ID NO: 31.

Functional homologs of BHC80 comprise at least about amino acid 444, 440, 430, or 400 to about amino acid 487, 490, or 500 of SEQ ID NO: 35.

Whether a homolog is a functional homolog can be determined according to methods known in the art. For example, a demethylase activity can be determined as described in the Examples. An illustrative example for determining whether a demethylase homolog has demethylase activity includes contacting the demethylase homolog with a target peptide that is methylated, and determining whether the demethylase homolog is capable of demethylating the target peptide. The assay may further comprise one or more other components, such as other proteins, e.g., CoREST, or cofactors, e.g., flavin adenine dinucleotide (FAD). A target peptide may be a histone peptide. Any histone peptide can be used. Preferably it is used with a histone demethylase enzyme that recognizes the histone peptide as a substrate. The full histone protein can be used or a peptide comprising only a portion of the histone protein can be used, so long as that portion contains the methylated residue upon which the demethylase enzyme acts and the portion contains sufficient contextual residues to permit its recognition by the enzyme. Typically at least 3, at least 4, at least 5, at least 6, or at least 7 residues on either side of the methylated residue are believed to be sufficient for recognition. The methylated residue can be either a lysine or an arginine. Preferably the histone peptide and the histone demethylase are derived from the same species of organism.

Measurement of the reaction between a histone and an eukaryotic histone demethylase protein can be accomplished by any means known in the art. These include, without limitation Western blotting, measuring formation of formaldehyde, mass spectrometry, and measuring formation of peroxide.

Methods for modulating the expression of a gene whose expression is modulated by the methylation status of one or more histones may comprise modulating the acetylation/deacetylation status of one or more histones. In one embodiment, demethylation is facilitated or improved by deacetylation. Accordingly, in certain embodiments, a method comprising increasing LSD1 protein level or activity in a cell comprises contacting the cell with an agent that increases histone deacetylase (HDAC) protein or activity levels and/or an agent that decreases histone acetylase protein or activity levels. On the other hand, a method comprising decreasing LSD1 protein level or activity in a cell may comprise contacting the cell with an agent that decreases HDAC protein or activity levels and/or an agent that increases histone acetylase protein or activity levels.

Methods for modulating the expression of a gene whose expression is modulated by the methylation status of one or more histones may also comprise (i) modulating the methylation status and (ii) modulating the acetylation status of one or more histones involved in regulating the expression of the gene.

The following Table (Table 4) summarizes how gene expression of methylated histone-repressed and histone-activated genes can be modulated by modulating the level of protein or activity of deacetylases or acetylases:

| Gene | modulation | deacetylase | acetylase |
|---|---|---|---|
| methylated histone-repressed | activation | increase | decrease |
| | repression | decrease | increase |

-continued

| Gene | modulation | deacetylase | acetylase |
|---|---|---|---|
| methylated histone-activated | activation | decrease | increase |
| | repression | increase | decrease |

"Increase" and "decrease" is as described above for Table 1.

An "acetylase" is used interchangeable herein with "acetyl transferase" and refers to an enzyme that catalyzes the addition of an acetyl group ($CH_3CO^-$) to an amino acid. Exemplary acetyl transferases are histone acetyl transferases (HAT).

The term "deacetylase" refers to an enzyme that catalyzes the removal of an acetyl group ($CH_3CO^-$) from an amino acid. Class I histone deacetylases (HDACs) includes the yeast Rpd3-like proteins (HDAC1, HDAC2, HDAC3, HDAC8, and HDAC11. Class II HDACs includes the yeast Hda1-like proteins HDAC4, HDAC5, HDAC6, HDAC7, HDAC9, and HDAC10 (Fischle, W., et al., *J. Biol. Chem.*, 274, 11713-11720 (1999)). Class III HDACs includes the silent mating type information regulation 2 (Sir2) and homologs thereof, such as SIRT1 in humans.

The nucleotide and amino acid sequences of each of these human HDACs and the location of conserved domains in their amino acid sequences is set forth in the following table (Table 5) ("i" refers to "isoform"):

| HDAC | nucleotide sequence | amino acid sequence | conserved domains (in amino acids) |
|---|---|---|---|
| HDAC1 | NM_004964 | NP_004955 | 28-321 |
| HDAC2 | NM_001527 | NP_001518 | 29-322 |
| HDAC3 | NM_003883 | NP_003874 | 3-315 |
| HDAC4 | NM_006037 | NP_006028 | 91-142; 653-994 |
| HDAC5i1 | NM_001015053 | NP_001015053 | 683-1026 |
| i2 | NM_005474 | NP_005465 | 682-1025 |
| HDAC6 | NM_006044 | NP_006035 | 1132-1180; 883-1068; 480-796; 84-404 |
| HDAC7Ai1 | NM_015401 | NP_056216 | 519-829 |
| i2 | NM_016596 | NP_057680 | 479-789 |
| HDAC8 | NM_018486 | NP_060956 | 16-324 |
| HDAC9i1 | NM_014707 | NP_055522 | |
| i2 | NM_058176 | NP_478056 | 633-974 |
| i3 | NM_058177 | NP_478057 | 633-860 |
| i4 | NM_178423 | NP_848510 | 633-974 |
| i5 | NM_178425 | NP_848512 | 636-977 |
| HDAC10 | NM_032019 | NP_114408 | 1-315 |
| HDAC11 | NM_024827 | NP_079103 | 17-321 |
| SIRT1 | NM_012238 | NP_036370 | 431-536; 254-489 |
| SIRT2 i1 | NM_012237 | NP_036369 | 77-331 |
| i2 | NM_030593 | NP_085096 | 40-294 |
| SIRT3 ia | NM_012239 | NP_036371 | 138-373 |
| ib | NM_001017524 | NP_001017524 | 1-231 |
| SIRT4 | NM_012240 | NP_036372 | 47-308 |
| SIRT5 i1 | NM_012241 | NP_036373 | 51-301 |
| i2 | NM_031244 | NP_112534 | 51-287 |
| SIRT6 | NM_016539 | NP_057623 | 45-257 |
| SIRT7 | NM_016538 | NP_057622 | 100-314 |

Other sirtuin family members include the yeast Sir2-like genes termed "HST genes" (homologues of Sir two) HST1, HST2, HST3 and HST4 and their human homologues.

Methods for modulating gene expression of methylated histone repressed or activated genes may also include modulating the level of protein or activity of methylases. Thus, in a situation in which one desires to reduce methylation, a method may comprise decreasing the level of protein or activity of one or more methylases, whereas in a situation in which one desires to increase methylation, a method may comprise increasing the level of protein or activity of one or more methylases.

Nucleic acids, e.g., those encoding a protein of interest or functional homolog thereof, or a nucleic acid intended to inhibit the production of a protein of interest (e.g., siRNA or antisense RNA) can be delivered to cells, e.g., eukaryotic cells, in culture, to cells ex vivo, and to cells in vivo. The cells can be of any type including without limitation cancer cells, stem cells, neuronal cells, and non-neuronal cells. The delivery of nucleic acids can be by any technique known in the art including viral mediated gene transfer, liposome mediated gene transfer, direct injection into a target tissue, organ, or tumor, injection into vasculature which supplies a target tissue or organ.

Polynucleotides can be administered in any suitable formulations known in the art. These can be as virus particles, as naked DNA, in liposomes, in complexes with polymeric carriers, etc. Polynucleotides can be administered to the arteries which feed a tissue or tumor. They can also be administered to adjacent tissue, whether tumor or normal, which could express the demethylase protein.

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

A polynucleotide of interest can also be combined with a condensing agent to form a gene delivery vehicle. The condensing agent may be a polycation, such as polylysine, polyarginine, polyornithine, protamine, spermine, spermidine, and putrescine. Many suitable methods for making such linkages are known in the art.

In an alternative embodiment, a polynucleotide of interest is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, Biochemistry, pp. 236-240, 1975 (W.H. Freeman, San Francisco, Calif.); Szoka et al., Biochim. Biophys. Acta 600:1, 1980; Bayer et al., Biochim. Biophys. Acta. 550:464, 1979; Rivnay et al., Meth. Enzymol. 149:119, 1987; Wang et al., PROC. NATL. ACAD. SCI. U.S.A. 84: 7851, 1987, Plant et al., Anal. Biochem. 176:420, 1989, and U.S. Pat. No. 4,762,915. Liposomes can encapsulate a variety of nucleic acid molecules including DNA, RNA, plasmids, and expression constructs comprising growth factor polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., Proc. Natl. Acad. Sci. USA 84:7413-7416, 1987), mRNA (Malone et al., Proc. Natl. Acad. Sci. USA 86:6077-6081, 1989), and purified transcription factors (Debs et al., J. Biol. Chem. 265:10189-10192, 1990), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Felgner et al., Proc. Natl. Acad. Sci. USA 91: 5148-5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA 75:4194-4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

One or more protein (e.g., a demethylaes) or nucleic acid (e.g., siRNA) of interest may be encoded by a single nucleic acid delivered. Alternatively, separate nucleic acids may encode different protein or nucleic acids of interest. Different species of nucleic acids may be in different forms; they may use different promoters or different vectors or different delivery vehicles. Similarly, the same protein or nucleic acid of interest may be used in a combination of different forms.

Antisense molecules, siRNA or shRNA molecules, ribozymes or triplex molecules may be contacted with a cell or administered to an organism. Alternatively, constructs encoding these may be contacted with or introduced into a cell or organism. Antisense constructs, antisense oligonucleotides, RNA interference constructs or siRNA duplex RNA molecules can be used to interfere with expression of a protein of interest, e.g., a histone demethylase. Typically at least 15, 17, 19, or 21 nucleotides of the complement of the mRNA sequence are sufficient for an antisense molecule. Typically at least 19, 21, 22, or 23 nucleotides of a target sequence are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired histone demethylase sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

Antisense or RNA interference molecules can be delivered in vitro to cells or in vivo, e.g., to tumors of a mammal. Typical delivery means known in the art can be used. For example, delivery to a tumor can be accomplished by intratumoral injections. Other modes of delivery can be used without limitation, including: intravenous, intramuscular, intraperitoneal, intraarterial, local delivery during surgery, endoscopic, subcutaneous, and per os. In a mouse model, the antisense or RNA interference can be adminstered to a tumor cell in vitro, and the tumor cell can be subsequently administered to a mouse. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

Exemplary siRNA or antisense molecules targeting LSD1 genes comprise the following nucleotide sequences or the complement thereof: 5'atgtcaaagatgagcagatt 3' (SEQ ID NO: 38; which targets both mouse and human LSD1); 5'ggcgaaggtagagtacagaga 3' (SEQ ID NO: 39; which targets human LSD1); and 5'ccatggttgtaacaggtctt 3' (SEQ ID NO: 40; which targets mouse LSD1).

An exemplary siRNA or antisense molecule targeting human and mouse CoREST genes comprises the following nucleotide sequence or the complement thereof: 5'gacaatcttggcatgttggt 3' (SEQ ID NO: 41).

An exemplary siRNA or antisense molecule targeting human BHC80 genes comprises the following nucleotide sequences or the complement thereof: 5' ggacctcaaactgtacagctt 3' (SEQ ID NO: 42).

Also provided herein are compositions, e.g., pharmaceutical compositions, and kits comprising one or more agent described herein. Kits may further comprise devices for administering the one or more agent to a subject. A device may be a syringe or a stent.

Exemplary Methods of Treatment and Diseases

Provided herein are methods of treatment or prevention of conditions and diseases that can be improved by modulating the methylation status of histones, and thereby, e.g., modulate the level of expression of methylation activated and methylation repressed target genes, such as an acetylcholine receptor, an SCN gene, p57 and genes regulated by the androgen receptor. A method may comprise administering to a subject, e.g., a subject in need thereof, a therapeutically effective amount of an agent described herein.

Diseases such as cancers and neurological disease can be treated by administration of modulators of histone methylation, e.g., modulators of histone demethylase enzyme activity. Histone methylation has been reported to be involved in overexpression of certain genes in cancers and of silencing of neuronal genes in non-neuronal cells. Modulators that are identified by the disclosed methods or modulators that are described herein can be used to treat these diseases, i.e., to restore normal methylation to affected cells.

Based at least on the fact that increased histone methylation has been found to be associated with certain cancers, a method for treating cancer in a subject may comprise administering to the subject a therapeutically effective amount of one or more agents that decrease methylation or restores methylation to its level in corresponding normal cells.

It is believed that modulators of methylation can be used for modulating cell proliferation generally. Excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growths.

Exemplary cancers that may be treated include leukemias, e.g., acute lymphoid leukemia and myeloid leukemia, and carcinomas, such as colorectal carcinoma and hepatocarcinoma. Other cancers include Acute Lymphoblastic Leukemia; Acute Lymphoblastic Leukemia; Acute Myeloid Leukemia; Acute Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Brain Tumor; Breast Cancer; Breast Cancer and Pregnancy; Breast Cancer; Breast Cancer, Male; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cerebral Astrocytoma/Malignant Glioma; Cervical Cancer; Childhood Cancers; Chronic Lymphocytic Leukemia; Chronic Myelogenous Leukemia; Chronic Myeloproliferative Disorders; Colon Cancer; Colorectal Cancer; Cutaneous T-Cell Lymphoma, see Mycosis Fungoides and Sezary Syndrome; Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sézary Syndrome; Lymphoma, Hodgkin's; Lymphoma, Hodgkin's; Lymphoma, Hodgkin's During Pregnancy; Lymphoma, Non-Hodgkin's; Lymphoma, Non-Hodgkin's; Lymphoma, Non-Hodgkin's During Pregnancy; Lymphoma, Primary Central Nervous System; Macroglobulinemia, Waldenström's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer; Neuroblastoma; Non-Hodgkin's Lymphoma; Non-Hodgkin's Lymphoma; Non-Hodgkin's Lymphoma During Pregnancy; Non-Small Cell Lung Cancer; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Unknown Primary Site, Carcinoma of; Unknown Primary Site, Cancer of; Unusual Cancers of Childhood; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenström's Macroglobulinemia; Wilms' Tumor; and Women's Cancers.

Neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetics, in particular methylation, plays a role is likely to be treatable or preventable by applying methods described herein.

Screening Methods

Also provided herein are screening methods for identifying agents that modulate methylation of a target protein, such as a histone, e.g., lysine 4 (K4) of histone 3.

One method comprises identifying an agent that modulates the interaction between a histone demethylase protein and a CoREST protein, comprising contacting a histone demethylase reagent and a CoREST reagent in the presence of a test agent; and (ii) determining the level of interaction between the histone demethylase reagent and the CoREST reagent, wherein a different level of interaction between the histone demethylase reagent and the CoREST reagent in the presence of the test agent relative to the absence of the test agent indicates that the test agent is an agent that modulates the interaction between a histone demethylase protein and a CoREST protein. The method may further comprise at least one other component of a histone demethylase transcription complex. The method may also comprise determining the effect of the test agent on a biological activity of the histone demethylase. For example, a method may further comprise contacting a histone demethylase reagent and a CoREST reagent with the test agent and determining the biological activity of the histone demethylase reagent, wherein a different activity of the histone demethylase reagent in the presence of the test agent relative to the absence of the test agent indicates that the test agent is an agent that modulates the biological activity of a histone demethylase.

A method for identifying an agent that modulates the biological activity of a histone demethylase may comprise: (i) contacting a histone demethylase reagent with a CoREST reagent in the presence of a test agent; and (ii) determining the biological activity of the histone demethylase reagent, wherein a different activity of the histone demethylase reagent in the presence of the test agent relative to the absence of the test agent indicates that the test agent is an agent that modulates the biological activity of a histone demethylase. A higher activity indicates that the test agent is an agent that stimulates the biological activity of a histone demethylase. The biological activity of the histone demethylase reagent may be demethylase activity or amine oxidase activity. The CoREST reagent may comprise at least about amino acids 293 to 381 or 293 to 482 of human CoREST.

A method for identifying an agent that modulates the interaction between a histone demethylase protein and a BHC80 protein may comprise contacting a histone demethylase reagent and a BHC80 reagent in the presence of a test agent; and (ii) determining the level of interaction between the histone demethylase reagent and the BHC80 reagent, wherein a different level of interaction between the histone demethylase reagent and the BHC80 reagent in the presence of the test agent relative to the absence of the test agent indicates that the test agent is an agent that modulates the interaction between a histone demethylase protein and a BHC80 protein. Step (i) may further comprise at least one other component of a histone demethylase transcription complex. The method may further comprise determining the effect of the test agent on a biological activity of the histone demethylase. The method may comprise contacting a histone demethylase reagent and a HDC80 reagent with the test agent and determining the biological activity of the histone demethylase reagent, wherein a different activity of the histone demethylase reagent in the presence of the test agent relative to the absence of the test agent indicates that the test agent is an agent that modulates the biological activity of a histone demethylase.

A method for identifying an agent that modulates the biological activity of a histone demethylase may comprise: (i) contacting a histone demethylase reagent with a HDC80 reagent in the presence of a test agent; and (ii) determining the biological activity of the histone demethylase reagent, wherein a different activity of the histone demethylase reagent in the presence of the test agent relative to the absence of the test agent indicates that the test agent is an agent that modulates the biological activity of a histone demethylase. A higher activity indicates that the test agent is an agent that stimulates the biological activity of a histone demethylase. The biological activity of the histone demethylase reagent is demethylase activity or amine oxidase activity.

"LSD1 reagent", "CoREST reagent" and "BHC80 reagent" refers to an LSD1, CoREST or BHC80 protein, homolog, or functional homolog thereof or portion thereof sufficient for use in the particular assay. For example, in an assay for determining whether two proteins interact, it is only necessary to include portions of those proteins that interact with each other.

Reagents may comprise at least a portion of a protein of interest, e.g., an LSD1, CoREST or BHC80 protein fused directly or indirectly to another moiety or label, e.g., a fluorophore or radioactive label or another peptide that may be useful in identifying, quantitating, isolating or purifying the reagent.

Other methods for identifying agents that modulate demethylase activity include methods using a reporter gene and a gene involved in methylation, e.g., LSD1, CoREST or BHC80. A method may comprise (i) providing a cell or cell lysate comprising an LSD1, CoREST or BHC80 gene or portion, e.g., promoter and/or enhancer, thereof, operably linked to a reporter gene and (ii) contacting the cell or cell lysate with a test agent and (iii) determining the level of expression of the reporter gene, wherein a higher level of expression of the reporter gene in the presence of the test agent relative to the absence of the test agent indicates that the test agent is an agent that increases the level of expression of the LSD1, CoREST or BHC80 gene, whereas a lower level of expression of the reporter gene in the presence of the test agent relative to the absence of the test agent indicates that the test agent is an agent that decreases the level of expression of the LSD1, CoREST or BHC80 gene. A reporter gene may encode firefly luciferase, chloramphenicol acetyltransferase, beta-galactosidase, green fluorescent protein, or alkaline phosphatase.

A screening assay described herein may further comprise testing the effect of the test agent on the demethylase activity in a cell. For example, a test reagent may be contacted with or administered into a cell and the level of expression of one or more genes whose expression is regulated by methylation may be measured. Alternatively, or in addition, the level of protein, e.g., LSD1, CoREST or BHC80 protein may be measured.

Test agents (or substances) for screening as inhibitors or enhancers of the demethylase enzymes can be from any source known in the art. They can be natural products, purified or mixtures, synthetic compounds, members of compound libraries, etc. The compounds to be tested may be chosen at random or may be chosen using a filter based on structure and/or mechanism of the enzymes. The test substances can be selected from those that have previously identified to have biological or drug activity or from those that have not. In some embodiments a natural substrate is the starting point for designing an inhibitor. Modifications to make the substrate non-modifiable by the enzyme can be used to make an inhibitor.

Also provided herein are compositions and molecular complexes comprising one or more proteins described herein. A composition may be a pharmaceutical composition.

All publications, including patents, applications, and GenBank Accession numbers mentioned herein are hereby incorporated by reference in their entirety as if each individual publication or patent was specifically and individually indicated to be incorporated by reference. In case of conflict, the present application, including any definitions herein, will control.

The invention now being generally described, it will be more readily understood by reference to the following examples, which are included merely for purposes of illustration of certain aspects and embodiments of the present invention, and are not intended to limit the invention.

EXAMPLE 1

To understand the function and mechanism of action of KIAA0601, we undertook molecular, biochemical and enzymological analyses of the protein. Using multiple experimental approaches, we demonstrate that KIAA0601 is a lysine-specific demethylase with substrate specificity for K4 methylated histone H3. We now refer to protein as LSD1 (Lysine Specific Demethylase 1) to reflect this newly identified role. The text and figures corresponding to this example may be found in Shi et al. Cell (2004) 119:903, which is specifically incorporated by reference herein.

LSD1 is a Transcriptional Co-repressor that is Evolutionarily Conserved

FIG. 1A shows a schematic diagram of the predicted domains of LSD1 and its related proteins. The C-terminal 2/3 of LSD1 display significant sequence homology with FAD-dependent amine oxidases. The N-terminus of LSD1 has a SWIRM domain, which is found in a number of proteins involved in chromatin regulation (Aravind and Iyer, 2002). Although the function of the SWIRM domain is currently unclear, the domain sets LSD1 and its family members apart from the conventional amine oxidases involved in metabolism. By searching for proteins that have both the amine oxidase and the SWIRM domains, we identified an LSD1-like protein AOF1 in human (FIG. 1A). In addition, we found three LSD-like proteins in *C. elegans*, one in *Drosophila*, five in Arabadopsis, and two in *S. pombe* (FIG. 1A). Some members such as SPAC23E2.02 of *S. pombe* contain an additional HMG box, suggesting possible DNA binding activity. The amino oxidase homology region was used for the construction of a phylogenetic tree shown in FIG. 1B. Interestingly, LSD1 homologs appear to be absent in *S. cerevisiae*.

Since LSD1 has been found in a number of co-repressor complexes (Hakimi et al., 2002; Hakimi et al., 2003; Humphrey et al., 2001; Shi et al., 2003; Tong et al., 1998; You et al., 2001), we wished to determine whether it plays a direct role in transcriptional repression. We first asked whether LSD1 functions as a repressor when directed to a target promoter. When fused to the GAL4 DNA binding domain (G4LSD1), LSD1 repressed G4-TK-Luc reporter gene in a dose-dependent manner. As a control, G4 DNA binding domain alone (G4DBD) had no repressive effect on the same promoter and instead activated the promoter slightly. Furthermore, G4LSD1 had no effect on TK-Luc reporter lacking the G4 binding sites suggesting that repression was not due to squelching. Importantly, a C-terminal deletion mutant (G4LSD1ΔC) that lacks a large portion of the amine oxidase homologous region (diagrammed in FIG. 1C) and is therefore enzymatically inactive (see below) was significantly compromised in its ability to repress transcription, although some residual repression activity was observed for this mutant. Since repression mediated by LSD1 requires the C-terminal amine oxidase homology domain, the transcriptional function of LSD1 may therefore be linked to its enzymatic activity.

EXAMPLE 2

LSD1 is a Lysine-specific Histone Demethylase

Figure 2:
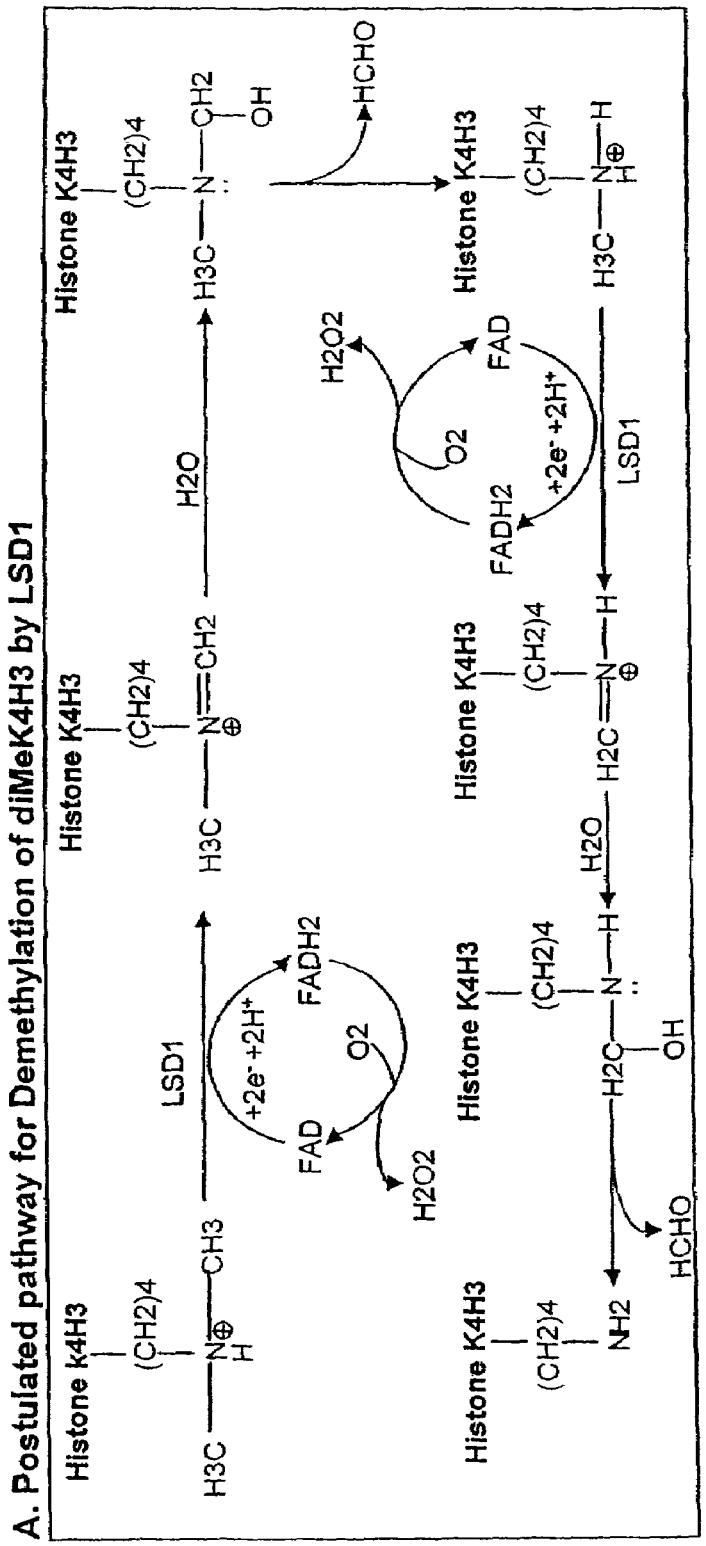
FIG. 2. Demethylation of diMeK4H3 peptides by LSD1. Possible chemical reactions for LSD1-catalyzed demethylation. Only diMeK4H3 is shown, but the proposed reactions are also compatible with mono-methylated lysines or methylated arginines.

LSD1 is a flavin-containing protein based on its ability to bind FAD ((Humphrey et al., 2001), and data not shown). Its sequence homology with amine oxidases predicts that LSD1 may catalyze oxidation reactions of biogenic amines including monoamine, polyamines or N-methylated protein substrates (such as histones) (Bannister et al., 2002). Amine oxidation catalyzed by flavin-containing amine oxidase is characterized by oxidative cleavage of the α-carbon bond of the substrate to form an imine intermediate, which, in turn, is hydrolyzed to form an aldehyde and amine via a non-enzymatic process. In a complete catalytic cycle, the cofactor FAD is reduced to $FADH_2$ and then is likely to be re-oxidized by oxygen to produce hydrogen peroxide (Binda et al., 2002). We hypothesized that, as a flavin-containing amine oxidase homolog, LSD1 may catalyze the conversion of mono- or dimethylated K (or R) to non-methylated K (or R) and formaldehyde (FIG. 2). Since LSD1 is a transcriptional co-repressor, we further speculated that it might specifically remove methyl groups from lysine (or arginine) whose methylation is linked to active transcription. We chose to focus on H3-K4 methylation since this is one of the best-characterized sites where both di- and tri-methylation have been linked to active transcription (Liang et al., 2004; Litt et al., 2001; Noma et al., 2001; Santos-Rosa et al., 2002; Schneider et al., 2004). To investigate this possibility, a histidine epitope-tagged LSD1 (HIS-LSD1) was expressed in bacteria and purified to near homogeneity (FIG. 2). FAD was found to co-purify with LSD1 rendering the purified protein yellow, which is characteristic of FAD-bound proteins. The HIS-LSD1 proteins were incubated with histone H3 peptides carrying dimethylated K4 (diMeK4H3) or K9 (diMeK9H3) and the methylation status was determined using a diMeK4H3 or diMeK9H3 specific antibody, respectively. Even the lowest amount of LSD1 used (1 μg=10 pmole) effectively reduced dimethylation level at K4 (1 nmole of diMeK4H3) but had no effect on non-methylated H3. This represented approximately 1:100 molar ratio of LSD1 to diMeK4H3, consistent with this being an enzyme-driven reaction. In contrast, LSD1 failed to reduce the dimethylation level at K9, indicating substrate specificity of this enzyme. The significant reduction of the methylation signal on K4 in the presence of LSD1 was not due to degradation of the diMeK4H3 peptides since LSD1 had no affect on the stability of the H3 peptides. This putative enzymatic activity is abolished upon heat treatment, which caused protein denaturation, consistent with the possibility that LSD1 was the enzyme responsible for the observed demethylation. As a control, FMS1, which is an amine oxidase related to LSD1 in sequence, failed to catalyze the same enzymatic reaction. In contrast, FMS1 has previously been shown to catalyze oxidation of polyamine (Landry and Sternglanz, 2003). Importantly, HIS-LSD1 had barely detectable polyamine oxidation activity, yielding only a two-fold above background signal, which was about a thousand fold less active than FMS 1. Therefore, LSD1 is likely a histone demethylase but not a polyamine oxidase. Significantly, the same C-terminal deletion mutant LSD1ΔC, which was compromised transcriptionally (FIG. 1E), also failed to demethylate diMeK4H3 peptides suggesting that LSD1-mediated transcriptional repression may be linked to this potential histone demethylase activity.

We next asked whether LSD1 can mediate demethylation reactions using native histones isolated from HeLa cells as substrates. Wild type LSD1, but, not LSD1ΔC, significantly reduced the signals detected by the diMeK4H3 antibody. The same blot was re-probed by a pan H3 acetylation antibody, which detected similar levels of acetylation with or without LSD1, suggesting that the loss of the methylation signal was not due to fortuitous degradation of histone H3. We next determined whether LSD1 could catalyze demethylation of histone H3 with either mono- or tri-methylated K4, the latter modification being also linked to active transcription. While LSD1 reduced the signal representing mono-methylated K4 of histone H3, it had no effect on trimethylated K4. The inability of LSD1 to convert tri-methylated K4 to an unmodified product is likely to be due to the inherent chemistry of the flavin-containing amine oxidases, which requires a protonated nitrogen in the substrates, thus restricting the substrates to mono- or dimethylated peptides (FIG. 2). The modification-specific antibodies used in the above assays were either commercial antibodies (see experimental procedures) or antibodies that have been reported in the literatures (e.g., anti-diMeK79H3 and anti-diMeK20H4 (Feng Q, 2002 and Fang J, 2002)).

To further determine the substrate specificity of LSD1, we examined a number of other amino acid residues on histones whose methylation is likely to be linked to active transcription, including K36 and K79 of histone H3 (Feng et al., 2002; Krogan et al., 2003; Ng et al., 2003a; Schaft et al., 2003), R2, R17 and R26 of histone H3 (Bauer et al., 2002; Chen et al., 1999; Schurter et al., 2001) and R3 of histone H4 (Strahl et al., 2001). We found no difference in the signal intensity detected by Western blotting, in the presence or absence of LSD1, using the modification-specific antibodies designed to visualize methylation at these sites, suggesting a high level of substrate specificity of this putative enzymatic activity. LSD1 also failed to remove the methyl groups from H3-K9, H3-K27 and H4-K20, modifications that are linked to transcriptional silencing (Cao et al., 2002, Czermin, 2002 #2921; Fang et al., 2002; Kuzmichev et al., 2002; Muller et al., 2002; Nishioka et al., 2002; Rea et al., 2000). Similar to the bacterially purified LSD1, endogenous LSD1 isolated from HeLa cells also displayed the same substrate specificity as the recombinant HIS-LSD1 protein. Taken together, these findings support our model that LSD1 functions as a transcriptional co-repressor by demethylating sites associated with active transcription but not repression.

To confirm the above results, we turned to mass spectrometry. As predicted by the chemical reaction outlined in FIG. 2, demethylation of a dimethyl-K4 histone H3 by LSD1 is expected to regenerate an unmodified histone H3 with the net loss of 28 Dalton equal to the molecular weight of 2 $CH_2$. K4- and K9-dimethylated histone H3 peptides were incubated with purified HIS-LSD1, respectively, and the reaction mixtures were analyzed by mass spectrometry. The diMeK4H3 peptide peaked at molecular mass of 2863 Dalton as expected. Significantly, upon incubation with HIS-LSD1 but not HIS-LSD1ΔC, a new peak appeared at a molecular mass of 2835 Dalton that corresponded to the molecular weight of the unmodified histone H3 peptide. As a control, the K9-dimethylated H3 peptides were found to be unaffected by HIS-LSD1, consistent with the Western blotting results described earlier. Taken together these findings strongly suggest that LSD1 is a histone demethylase with a substrate preference for methylated K4 over K9 of histone H3.

EXAMPLE 3

LSD1-mediated Histone Demethylation Generates Formaldehyde

We used a third independent method to investigate the possibility that LSD1 is a histone demethylase. As shown in FIG. 2, the demethylation reaction mediated by LSD1 is predicted to generate formaldehyde. To determine whether formaldehyde was produced in LSD1-mediated enzymatic reactions, we first used the formaldehyde dehydrogenase (FDH) assay to detect the presence of formaldehyde (Lizcano et al., 2000). This assay employs formaldehyde dehydrogenase to convert formaldehyde to formic acid using $NAD^+$ as the electron acceptor, whose reduction to NADH can be spectrophotometrically measured at OD 340 nm. Thus, when the demethylation reaction is coupled with the FDH assay, the enzymatic activity of LSD1 and reaction kinetics can be determined by measuring the production of NADH. A standard curve was first generated using purified FDH (EC 1.2.1.46), $NAD^+$ and different concentrations of formaldehyde ranging from 1 μM to 10 mM, within which a linear relationship was found between the production of NADH and the range of formaldehyde used in the assay. Subsequently, the coupled demethylation-FDH assays were carried out within this linear range and were initiated with the addition of the diMeK4H3 substrates. The continuous production of the formaldehyde as the demethylation proceeded was monitored by OD measurement at 340 nm at different time points. A robust increase of absorbance at 340 nm was observed within the first five minutes of the reaction, indicating that substantial amounts of formaldehyde were produced in the LSD1-catalyzed demethylation reaction. The fact that formaldehyde was generated in the demethylation reaction strongly suggests that the reaction had occurred as proposed in FIG. 2. Increasing the amount of either the enzyme (LSD1) or the substrates (diMeK4H3) in the demethylation reaction resulted in a dose-responsive increase in the conversion of NAD to NADH, respectively. We next used the demethylation-FDH coupled spectrophotometric assay as another independent means to investigate the substrate specificity of LSD1. Only when HIS-LSD1 was incubated with diMeK4H3, but not diMeR2H3 or diMeK9H3, did we detect a robust increase in the absorbance at OD 340 nm, indicating the production of formaldehyde and thus successful demethylation. Furthermore, we failed to detect formaldehyde when triMeK4H3 was used as substrate, suggesting that LSD1 is also unable to catalyze demethylation of the triMeK4H3 peptide. This result is consistent with the Western blotting assays using modification specific antibodies.

To further confirm the production of formaldehyde in the LSD1-mediated demethylation reaction, we next used Electrospray Ionization Liquid Chromatography-Mass Spectrometry (ESI-LC-MS) to detect formaldehyde. The formaldehyde produced in the demethylation reaction was captured by dimedone to irreversibly form the dimedone adduct, formaldemethone, which can be detected by the absorbance at OD 254 nm (Rozylo et al., 2000). The formaldemethone was eluted from an HPLC column and the mass of the formaldehyde derivative was analyzed by LC-MS. Using this assay, we identified formaldehyde in the LSD1-, but not LSD1ΔC-mediated demethylation reaction. Taken together, mass spectrometry and the FDH assay identified formaldehyde and unmodified histone H3 peptides as the products of the demethylation reaction catalyzed by LSD1.

EXAMPLE 4

LSD1 Regulation of Endogenous Target Gene Transcription and H3-K4 Methylation in vivo.

We next asked whether native LSD1 regulates endogenous target gene transcription and histone demethylation in vivo. Previous studies identified LSD1 in the Co-REST complex whose primary function is to silence neuronal specific genes in non-neuronal cells (Ballas et al., 2001). A number of Co-REST target genes have been reported including genes that encode the sodium channels (SCNs) and acetylcholine receptors (AchR) (Lunyak et al., 2002). We asked whether these promoters can be de-repressed when LSD1 was knocked down by DNA-vector based RNAi (Sui et al., 2002). The lsd1 RNAi plasmid reduced LSD1 expression efficiently, as judged by immunostaining and Western blotting. Concomitant with the decrease in LSD1 expression, we observed an increase in M4 AchR, SCN1A, SCN2A and SCN3A expression as determined by RT-PCR. De-repression of these target genes in the LSD1 knockdown cells indicates that LSD1 is an essential component of the Co-REST complex and is likely to be required for silencing specific neuronal genes in non-neuronal cells. However, LSD1 targets are probably not limited to neuron-specific genes. We also identified $p57^{KIP2}$, a cyclin-dependent kinase inhibitor (Lee et al., 1995), as a potential LSD1 target gene whose transcription also appeared to be negatively regulated by LSD1. Interestingly, $p57^{KIP2}$ has recently been shown to play a role in developing dopamine cells (Joseph et al., 2003).

We next investigated whether LSD1 regulates histone demethylation in vivo. Using chromatin immunoprecipitation (ChIP), we found LSD1 located at the target gene promoters (within 2 kb of the transcription initiation site) in HeLa or control RNAi treated cells, but LSD1 promoter occupancy was significantly reduced in the lsd1 RNAi cells. Importantly, concomitant with the decrease of LSD1 occupancy at the target promoters, we observed an increase in H3-K4 dimethylation that coincided with the increase in the promoter activity. Thus, LSD1 promoter occupancy appears to be inversely correlated with promoter activity and H3-K4 dimethylation. Taken together, these findings support the hypothesis that LSD1 regulates histone K4 demethylation at specific loci in vivo, which is correlated with LSD1-mediated repression of target gene transcription.

EXAMPLE 5

We have provided multiple lines of evidence that support the conclusion that LSD1 is a histone lysine demethylase. These include the direct demethylation assays; mass spectrometry and the demethylation-FDH coupled spectrophotometric assays that revealed the demethylation products, i.e., demethylated histone peptides (mass spectrometry) and formaldehyde (FDH and mass spectrometry). We have also shown that LSD1 functions as a transcriptional co-repressor and plays an important role in restricting neuron-specific gene transcription in non-neuronal HeLa cells. Importantly, RNAi inhibition of LSD1 resulted in an increase in H3-K4 methylation, which is linked to active transcription, and a concomitant de-repression of the target genes, suggesting that LSD1 mediates transcriptional repression via histone demethylation in vivo.

Strikingly, as a histone demethylase, LSD1 displays stringent substrate specificity, which is manifested at two different levels. First, LSD1 is able to distinguish histone H3 peptides with the same type of methylation (dimethylation on lysine) that occurred on different lysine residues (K4 versus K9, K36 and K79). It is possible that the sequences surrounding these two lysine residues may contribute to this selectivity. Second, the substrate specificity of LSD1 is further highlighted by its ability to discriminate between di- and tri-methylation methylation on the same lysine H3-K4. The inability to demethylate triMeK4H3 is consistent with the chemical nature of the amine oxidation reaction catalyzed by flavin-containing amine oxidases, which requires a protonated nitrogen and thus precludes triMeK4H3 as a substrate (FIG. 2 and (Bannister et al., 2002)). This suggests that either triMeK4H3 turnover is accomplished by histone replacement or by an unidentified triMeK4H3-specific demethylase. Alternatively, additional mechanisms, such as direct hydroxylation of the methyl groups, may be involved in converting triMeK4H3 to an unmodified product. Our findings further suggest that additional histone demethylases are yet to be identified that would catalyze demethylation reactions at other lysine and/or arginine residues that are associated with either activation or repression of transcription.

Kinetic analysis of LSD1 provided further support that LSD1 is a histone demethylase. The apparent Km for the diMeK4H3 substrates is approximately 30 µM, which is comparable to other histone modifying enzymes such as the NAD-dependent histone deacetylase Sir2 (Borra et al., 2004). The actual Km for the demethylation reaction in mammalian cells is likely to be lower since not all purified HIS-LSD1 proteins are expected to be fully active. Possible posttranslational modifications of LSD1 as well as interacting proteins of LSD1 may further enhance its activity in mammalian cells. The fact that the physiological substrates of LSD1 in vivo are nucleosomes may also influence the activity of LSD1, as could other posttranslational modifications on histones. Regardless, these findings provide important kinetic information that substantiates the idea that LSD1 is a histone demethylase.

Another crucial piece of information that supports the conclusion that LSD1 is a histone demethylase is our ability to identify the demethylation reaction products, i.e. formaldehyde and the unmodified histone H3 peptides. Thus we have accounted for the major reaction products during an amine oxidase-mediated demethylation reaction. In this oxidation reaction, the cofactor FAD is likely to be reduced to $FADH_2$ and then reoxidized to FAD by oxygen with the generation of H2O2. It will be important in the future to determine the fate of formaldehyde and $H_2O_2$, which could have potentially deleterious effects when present near promoters. Recently, a significant number of metabolic enzymes and coenzymes have been found to play central roles in regulating gene transcription (Shi, 2004). Further investigation of proteins such as LSD1 will provide insight into a possible direct link between metabolism and transcription.

Our finding that LSD1 regulates H3-K4 methylation at its target promoters but not global K4 demethylation (unpubl. result) suggests that LSD1 is a locus-specific histone demethylase. However, since LSD1 has been identified in numerous repressor complexes (Hakimi et al., 2002; Hakimi et al., 2003; Humphrey et al., 2001; Shi et al., 2003; Tong et al., 1998; You et al., 2001), we expect LSD1, much like the HDACs, to play a widespread and a central role in establishing repressive chromatin environment as a histone demethylase. We have previously shown that the CtBP repressor complex contains a number of potential enzymatic activities, including HDACs and HMTases that function coordinately to induce H3-K9 methylation, which is linked to transcriptional repression (Shi et al., 2003). We now show that another component of the CtBP complex, i.e., LSD1/nPAO, demethylates H3-K4 that is linked to active transcription. Taken together, these findings suggest that the establishment of a repressive environment mediated by the CtBP complex is likely to involve not only the process that confers the repressive modifications (HDACs and HMTases) but also events that erase histone modifications (LSD1) associated with active transcription. This level of complexity is consistent with the histone code hypothesis (Jenuwein and Allis, 2001) and is likely to represent a general principle underlying transcriptional regulation in eukaryotes. Lastly, in addition to H3-K9 methylation, H3-K4 hypomethylation has also been correlated with heterochromatin formation in S. pombe (Noma et al., 2001). It would be interesting to determine whether LSD1 homologs play a role in heterochromatin silencing as well as in euchromatic gene repression.

As with any fundamental biological processes, histone demethylation is expected to be conserved through evolution. In support of this hypothesis, we have identified LSD1 orthologs and homologs throughout the eukaryotic kingdom, ranging from S. pombe to human (FIG. 1). Curiously, LSD1-like proteins appear to be absent in S. cerevisiae where histone methylation also plays an important role in chromatin structure and transcriptional regulation. Thus, it is possible that S. cerevisiae may have evolved a different strategy to remove methyl groups from histones. Alternatively, different types of enzymes yet to be identified may be involved in demethylating histones in S. cerevisiae. In this regard, it is interesting to note that the S. cerevisiae genome, as do all the other eukaryotic genomes, has a large number of genes predicted to encode amine oxidases. It is possible that in addition to LSD1 family members, amine oxidases with a different architecture may also function as histone demethylases in S. cerevisiae and other organisms. Importantly, our findings documenting an amine oxidase functioning as a histone demethylase lays the foundation for investigation of other amine oxidases as candidates for histone demethylases. It will be exciting to determine if LSD1-related proteins and other types of oxidases function as histone demethylases with different substrate specificities to impact chromatin structure and gene transcription. Given our finding that histone demethylases exist, it will also be exciting to explore other types of enzymes that are also predicted to convert methylated peptides (such as histones) to unmethylated products (Chinenov, 2002).

Finally, recent studies provided a potential important connection between methylation at H3-K4 and cancer. The trithorax group protein MLL, which methylates H3-K4 is found to be frequently involved in chromosomal translocation in both acute lymphoid and myeloid leukemia (Ayton and Cleary, 2001). Another H3-K4 histone methylase, SMYD3, has been shown to be upregulated in colorectal and hepatocarcinoma cells (Hamamoto et al., 2004). Over-production of SMYD3 increases cell proliferation dependent on the histone methylase activity, consistent with the possibility that SMYD3 is a candidate oncogene (Hamamoto et al., 2004). These findings support the hypothesis that H3-K4 methylation regulation may play a crucial role in tumorigenesis. With the identification of LSD1 as a H3-K4 demethylase, we are now poised to investigate if LSD1 or related histone demethylases play a role in cancer, and if so, whether the demethylase activity is essential for this regulation.

EXAMPLE 6

Experimental Procedures

Peptides, histones, antibodies and chemical reagents. Synthetic histone peptides with specific modifications as well as antibodies (Ab) that recognize different histone modifications were purchased from either Upstate Group, INC (Lake Placid, N.Y.) (UP) or Abcam Ltd (Cambridge UK) (Ab). They are: diMeK4H3(1-21 aa) (UP 12-460), diMeK9H3 (1-21aa) (UP12-430), H3 (1-21aa) (UP12-403), PanH3Ac (1-21aa) (UP12-402), anti-diMeK4H3 Ab (UP07-030), anti-diMeK9H3 Ab (UP05-768), anti-panH3Ac (UP06-599), anti-monoMeK4H3 Ab (UP07-436), anti-H3 Ab (UP06-755), anti-diMeR2H3 Ab (Ab8046), anti-diMeR3H4 (UP07-213), anti-diMeK79H3 Ab (UP07-366), anti-diMeR17H3 (UP07-214), anti-diMeR26H3 (UP07-215) and triMeK4H3 (Ab1342). Anti-diMeK36H3 and Anti-diMeK20H4 antibodies were gifts from Y. Zhang. Bulk histones were either purchased from Sigma (catalog #H9250) or isolated from HeLa cells according to the protocol provided by Upstate. Formaldehyde dehydrogenase (EC1.2.1.46) purified from Pseudomonas putida was purchased from Sigma (F1879). Purified recombinant yeast polyamine oxidase FMS1 was a kind gift from Dr. Rolf Sternglanz.

Protein expression and purification. Full length (1-851aa) and C-terminal deleted (1-427 aa) human LSD1 cDNAs were cloned into N-terminal 6×HIS-tag bacterial expression vector pET15b. The plasmids were transformed into bacteria and expression of the recombinant proteins was induced by 0.2 mM IPTG at 37° C. for 6 hours. The HIS-tagged proteins were purified by Ni-NTA affinity column (Qiagen, Valencia, Calif.). After washing the column, the bound proteins were eluted from the column by 200 mM imidazole. The eluate was then extensively dialyzed in PBS with 3 times change at 4° C. The homogeneity and concentration of the protein were estimated on SDS-PAGE by Coomassie Blue staining using BSA as standard.

Demethylase assay. Bulk histones or histone peptides were incubated with purified HIS-LSD1 or HIS-LSD1ΔC in the histone demethylase activity (HDM) assay buffer 1 (50 mM Tris pH8.5, 50 mM KCl, 5 mM MgCl, 0.5% BSA and 5% glycerol) from 30 min up to 4 hours at 37° C. For a typical reaction, the volume of the reaction is 100 μl, in which either 20 μg of purified bulk histones or 3 μg of modified histone peptides were used as substrates. Different amounts of HIS-LSD1 ranging from 1-20 μg were used in the reaction. The reaction mixture was analyzed by SDS-PAGE/Western blotting using methyl-specific antibodies, or by formaldehyde formation assay to examine the removal and conversion of the methyl group to formaldehyde, or by mass spectrometry to identify the demethylated peptide.

MALDI Mass spectrometry (Matrix-assisted laser desorption/ionization mass spectroscopy). 2 μl of the 100 μl demethylation reaction mixture was desalted by passing through a $C_{18}$ ZipTip (Millipore). Prior to desalting, the ZipTips were activated and equilibrated using 10 μl of 50% acetonitrile/0.1% TFA (2×), followed by 10 μl of 0.1% trifluoroacetic acid (TFA) (3×). The reaction mixture was then loaded onto the activated ZipTips. The ZipTips were washed with 10 μl of 0.1% TFA (5×), and the bound material was eluted from the ZipTip using 2 μl of 70% acetonitrile containing 1 mg/ml α-cyano-4-hydroxycinnamic acid MALDI matrix and 0.1% TFA. The eluates were spotted onto a circle of open MALDI target areas to allow solvent evaporation and peptide/matrix co-crystallization. The samples were analyzed by a MALDI-TOF/TOF mass spectrometer (Ultraflex, Bruker Daltonics, Billerica, Mass.) at the PFPC core facility of Department of Pathology, Harvard Medical School.

Formaldehyde Dehydrogenase (FDH) assay. Formaldehyde formation was continuously monitored by a coupled spectrophotometric assay (Lizcano et al., 2000) using formaldehyde dehydrogenase (FDH). HIS-LSD1 was first incubated in buffer containing 50 mM potassium phosphate, pH 7.2, 2 mM NAD+ and 0.1 U FDH (100 µl reaction volume) at 37° C. for 5 min without substrates. The demethylation-FDH coupled reaction was initiated by the addition of the substrates. The absorbance at 340 nm ($\epsilon_{340}$=6.22 mM$^{-1}$cm$^{-1}$ for NADH) was measured at each time point in a 0.5 min interval using Beckman DU640 spectrophotometer. The OD 340 nm absorbance at the moment of the substrate addition was considered as 0 and this was used as the 0 min time point. Over a 10 min period, a kinetic software program automatically recorded the absorbance at each time point. The data were analyzed using the Excel program. Standard curves were obtained using various concentrations of formaldehyde diluted from 37% formaldehyde solution (Fisher). $K_m$ and $V_{max}$ values for the purified LSD1 catalyzing demethylation of the diMeK4H3 substrates were estimated using Lineweaver-Burk transformation of the Michaelis-Menten kinetic equation.

Electrospray Ionization-liquid chromatography-mass spectrometry (ESI-LC-MS). Standard formaldehyde or formaldehyde (FA) produced in the demethylation reaction was converted to formaldemethone (FDM) by the addition of dimedone, which has a strong absorbance at OD 254 nm and an increased mass suitable for MS detection. In a demethylation assay, 10 µg of enzyme and 15 µg of diMeK4H3 peptide were used in a 100 µl demethylation reaction. To convert FA to FDM, dimedone was added to the demethylation reaction (500 µl final volume with final concentration 0.0125%). For detection of FDM, samples were subjected to a reverse-phase high pressure liquid chromatography (HPLC) system (Agilent 1100) equipped with an analytical column (Waters Symmetry C18, 2.1×50 mm) at a flow rate of 0.4 ml/min. The HPLC system was directly coupled to a LCT mass spectrometer (MS) (Waters/Micromass). Analysis was performed in positive-ion electrospray (ESI) mode with acquisition across a mass range of 100 to 1000 daltons. The FDM were identified by the presence of a unique ion having a mass to charge ratio of 293.2, corresponding to the calculated molecular mass, with the addition of a single proton (M+H)$^+$.

RT-PCR. Total RNA samples were isolated from 2×10$^6$ cells by Trizol reagent (Sigma). After DNase treatment, the RNA samples were purified by phenol-chloroform extraction and ethanol precipitation. 38 PCR cycles were used for SCN1A, SCN2A, SCN3A and M4 AchR and 28 PCR cycles for GAPDH. Primers used in RT-PCR were as follows: SCN1A up (5'-gcgaaatagcagaacaagcc-3'; SEQ ID NO: 1), down (5'-ctcattgctcgttgcctttg-3'; SEQ ID NO: 2); SCN2A up (5'-gatgaggatgatgaaaatggc-3'; SEQ ID NO: 3), down (5'-ctaattttctaataggtttgaaggg-3'; SEQ ID NO: 4) SCN3A up (5'-caccacttcctactttaatggca-3'; SEQ ID NO: 5), down (5'-aaatagagacaggaaagcccag-3'; SEQ ID NO: 6); p57$^{KIP2}$ up (5'-ggcgatcaagaagctgtcc-3'; SEQ ID NO: 7), down (5'-caccttgggaccagtgtacc-3'; SEQ ID NO: 8); GAPDH up (5'-gaaggtgaaggtcggagtc-3'; SEQ ID NO: 9), down (5'-gaagatggtgatgggatttc-3'; SEQ ID NO: 10).

Chromatin Immunoprecipitation (ChIP) analysis. ChIP assays were carried out in IP buffer without SDS due to the sensitivity of the LSD1 antibody to SDS. Briefly, 3×10$^7$ cells were used per LSD1 ChIP and 3×10$^6$ cells per H3K4diMe ChIP. After 10 min 0.75% formaldehyde treatment, cells were harvested and sonicated in the ChIP lysis buffer (1% Triton X-100, 10 mM EDTA, 50 mM Tris-HCl and protease inhibitors) to produce soluble chromatin with average sizes between 300-1000 bp. The chromatin samples were then diluted 10 fold in the dilution buffer (5 mM EDTA, 25 mM Tris-HCl, 167 mM NaCl and cocktails of protease inhibitors) and pre-cleaned for 1 hour using salmon sperm DNA/protein-A agarose beads. 10 µg of rabbit anti-LSD1, 3 µl of anti-H3K4diMe or control antibodies were then added to each sample and incubated overnight at 4° C. To collect the immunocomplex, 40 µl of salmon sperm DNA/protein-A agarose beads were added to the samples for 1 hr at 4° C. The beads were washed 3× in the wash buffer 1 (0.1% Triton X-100, 5 mM EDTA, 30 mM Tris-HCl, 150 mM NaCl) and 1× in wash buffer 2 (1% Triton X-100, 5 mM EDTA, 30 mM Tris-HCl, 300 mM NaCl). The bound protein-DNA immunocomplexes were eluted with 100 µl elution buffer (1% SDS, 0.1 M NaHCO3, 250 mM NaCl and 0.2 µg/µl Protease K) and de-crosslinked at 65° C. for 4 hrs. The de-crosslinked chromatin DNA was further purified by QIAquick PCR Purification Kit (Qiagen) and eluted in 100 µl TE buffer. 4 µl of eluted DNA sample was used for each PCR reaction. 36 PCR cycles were used for LSD1 ChIP and 32 PCR cycles for H3K4diMe ChIP. Primers used for amplifications were as follows: M4 AchR forward (5'-gaacagaacacctccctcca-3'; SEQ ID NO: 11), reverse (5'-gagtcagaaggcaggacagg-3'; SEQ ID NO: 12); SCN1A forward (5'-taaagcccagtcaagacagc-3'; SEQ ID NO: 13), reverse (5'-gacacacccagaagatggag-3'; SEQ ID NO: 14); SCN2A forward (5'-cgtgtttcaaggctacagca-3'; SEQ ID NO: 15), reverse (5'-ctctagcctcccaaccttcc-3'; SEQ ID NO: 16); SCN3A forward (5'-ctctgtcacagggaggaaag-3'; SEQ ID NO: 17), reverse (5'-agactagagcaggccacaag-3; SEQ ID NO: 18); p57$^{KIP2}$ forward (5'-ccgtggtgttgttgaaactg-3'; SEQ ID NO: 19), reverse (5'-tgtccggtggtggactcttc-3'; SEQ ID NO: 20); GAPDH forward (5'-tcctcctgtttcatccaagc-3'; SEQ ID NO: 21), reverse (5'-tagtagccgggccctactt-3'; SEQ ID NO: 22).

Sequence of KIAA0601 is SEQ ID NO: 23. The nucleotide sequence encoding KIAA0601 is SEQ ID NO: 24. The sequence of Histone H3 is SEQ ID NO: 25. The sequence of AOF1 protein is SEQ ID NO: 26 and the sequence of AOF1 coding sequence is SEQ ID NO: 27:

References

The disclosure of each reference cited is expressly incorporated herein.

Ahmad et al. (2002) Mol Cell 9, 1191-1200; Allis et al. (1980) Cell 20, 55-64; Aravind et al. (2002) Genome Biol 3; Ayton et al. (2001) Oncogene 20, 5695-5707; Ballas et al. (2001) Neuron 31, 353-365; Bannister et al. (2002) Cell 109, 801-806; Bannister et al. (2001) Nature 410, 120-124; Bauer et al. (2002) EMBO Rep 3, 39-44; Binda et al. (2002) J Biol Chem 277, 23973-23976; Borra et al. (2004) Biochemistry 43, 9877-9887; Briggs et al. (2001) Genes Dev 15, 3286-3295; Cao et al. (2002) Science 298, 1039-1043; Chen (1999) Science 284, 2174-2177; Chinenov (2002) Trends Biochem Sci 27, 115-117; Cuthbert et al. (2004) Cell 118, 545-553; Eimer et al. (2003) EMBO Jo 21, 5787-5796; Fang et al. (2002) Curr Biol 12, 1086-1099; Feng et al. (2002) Curr Biol 12, 1052-1058; Hakimi et al. (2002) Proc Natl Acad Sci USA 99, 7420-7425; Hakimi et al. (2003) J Biol Chem 278, 7234-7239; Hamamoto et al. (2004) Nat Cell Biol 6, 731-740; Humphrey et al. (2001) J Biol Chem 276, 6817-6824; Jarriault et al. (2002) Genes & Dev 16, 2713-2728; Jenuwein et al. (2001) Science 293, 1074-1080; Johnson et al. (2004) Nat Immunol 5, 853-861; Joseph et al. (2003) Proc Natl Acad Sci USA 100, 15619-15624; Kim et al. (1964) J Biol Chem 239, 3790-3796; Kouzarides, T. (2000) EMBO Jo 19, 1176-1179;

Krogan et al. (2003) Mol Cell 11, 721-729; Kuzmichev et al. (2002) Genes Dev 16, 2893-2905; Lachner et al. (2001) Nature 410, 116-120; Landry et al. (2003) Biochem Biophys Res Commun 303, 771-776; Lee et al. (1995 Genes Dev 9, 639-649; Liang et al. (2004) Proc Natl Acad Sci USA 101, 7357-7362; Litt et al. (2001) Science 293, 2453-2455; Lizcano et al. (2000) Anal Biochem 286, 75-79; Lunyak et al. (2002) Science 298, 1747-1752; Muller et al. (2002) Cell 111, 197-208; Nakayama et al. (2001) Science 292, 110-113; Ng et al. (2003a) Proc Natl Acad Sci USA 100, 1820-1825; Ng et al. (2003b) Mol Cell 11, 709-719; Nielsen et al. (2001) Nature 412, 561-565; Nishioka et al. (2002) Mol Cell 9, 1201-1213; Noma et al. (2001) Science 293, 1150-1155; Paik et al. (1973) Biochem Biophys Res Commun 51, 781-788; Paik et al. (1974) Arch Biochem Biophys 165, 369-378; Peters et al. (2002) Nat Genet. 30, 77-80; Rea et al. (2000) Nature 406, 593-599; Rice et al. (2001) Curr Opin Cell Biol 13, 263-273; Roth et al. (2001) Annu Rev Biochem 70, 81-120; Rozylo et al. (2000) Biomed Chromatogr 14, 173-179; Santos-Rosa et al. (2002) Nature 419, 407-411; Schaft et al. (2003) Nucleic Acids Res 31, 2475-2482; Schneider et al. (2004) Nat Cell Biol 6, 73-77; Schurter et al. (2001) Biochemistry 40, 5747-5756; Shi et al. (2004) Trends Genet 20, 445-452; Shi et al. (2003) Nature 422, 735-738; Strahl et al. (2001) Curr Biol 11, 996-1000; Sui et al. (2002) Proc Natl Acad Sci USA 99, 5515-5520; Tong et al. (1998) Nature 395, 917-921; Wang et al. (2004) Science; You et al. (2001) Proc Natl Acad Sci USA 98, 1454-1458; and Zhang et al. (2001) Genes & Dev 15, 2343-2360.

EXAMPLE 7

Regulation of LSD1 Histone Demethylase Activity by its Associated Factors

LSD1 is a recently identified human lysine (K)-specific histone demethylase. LSD1 is associated with HDAC1/2, CoREST, a SANT domain-containing co-repressor, and BHC80, a PHD domain-containing protein, among others. We show that CoREST endows LSD1 with the ability to demethylate nucleosomal substrates and protects LSD1 from proteasomal degradation in vivo. We find hyperacetylated nucleosomes less susceptible to CoREST/LSD1-mediated demethylation, suggesting that hypoacetylated nucleosomes may be the preferred physiological substrates. This raises the possibility that histone deacetylases and LSD1 may collaborate to generate a repressive chromatin environment. Consistent with this model, TSA treatment results in de-repression of LSD1 target genes. While HDAC1/2 and CoREST positively regulate LSD1 function, BHC80 inhibits CoREST/LSD1-mediated demethylation in vitro and may therefore confer negative regulation. Taken together, these findings suggest that LSD1-mediated histone demethylation is regulated dynamically in vivo, and this is expected to have profound effects on gene expression under both physiological and pathological conditions. The text and figures corresponding to this example may be found in Shi et al. Mol. Cell. (2005) 19:1, which is specifically incorporated by reference herein.

The N-terminal tails of histones are subjected to multiple posttranslational modifications including methylation, which occurs on both lysine (K) and arginine (R) residues. Methylation on histone H3-K9 plays an important role in heterochromatin formation (Nakayama et al., 2001; Peters et al., 2002; Rea et al., 2000) as well as in euchromatin gene repression (Shi et al., 2003; Zhang and Reinberg, 2001). In contrast, methylation on the R and some K residues (such as H3-K4) is associated with active transcription (Kouzarides, 2002). Thus methylation represents a critical posttranslational modification of histones that impacts chromatin structure and gene transcription regulation (Bannister et al., 2002; Lachner and Jenuwein, 2002; Zhang and Reinberg, 2001).

Unlike other modifications that take place on histones such as acetylation and phosphorylation, methylation has long been thought to be a "permanent" modification. Challenging this current dogma, the recent discovery of the lysine specific histone demethylase LSD1 strongly suggests that histone methylation can be regulated dynamically via both histone methylases and demethylases (Shi et al., 2004). LSD1 (alias KIAA0601, p110b, npao and BHC110) is an amine oxidase, which mediates histone demethylation via an FAD-dependent oxidative reaction (Shi et al., 2004), and has been identified in a number of co-repressor complexes including CoREST, CtBP and a subset of HDAC complexes (Ballas et al., 2001; Hakimi et al., 2002; Hakimi et al., 2003; Humphrey et al., 2001; Shi et al., 2003; You et al., 2001). Consistent with these findings, LSD1 has been shown to function as a transcriptional co-repressor by demethylating K4 of histone H3 (Shi et al., 2004), where methylation is linked to active transcription (Liang et al., 2004; Litt et al., 2001; Noma et al., 2001; Santo-Rosa et al., 2002; Schneider et al., 2004). Interestingly, LSD1 has also been found in a histone H3-K4-specific methylase supercomplex (Nakamura et al., 2002), suggesting that LSD1 demethylation activity may be regulated in vivo. However, it has remained unclear if, when, and how LSD1 is regulated.

In this report, we address the issue of LSD1 regulation. We provide evidence that multiple factors associated with LSD1 regulate LSD1 histone demethylase function. Our findings suggest that LSD1-mediated histone demethylation is a stepwise, highly coordinated process that involves multiple LSD1-associated positive and negative regulatory factors including HDACs, CoREST and BHC80. These findings further suggest that LSD1-mediated histone demethylation is regulated dynamically in vivo, and this is expected to have profound effects on gene expression under both physiological and pathological conditions.

Results and Discussion

CoREST endows recombinant LSD1 with the ability to demethylate nucleosomal substrates. As described previously, bacterially purified LSD1 can demethylate mono- or dimethylated lysine 4 of histone H3 (H3-K4) when the substrate is either a histone peptide or free histone (Shi et al., 2004). In contrast, recombinant LSD1 was unable to demethylate nucleosomal substrates. Significantly, LSD1 purified from HeLa cells using the tandem affinity tag purification approach demethylated histones regardless of whether the substrates were bulk histones or histones assembled into the nucleosome. Mass spectrometry and Western blotting analysis identified a putative LSD1 complex (LSD1.com) containing HDAC1/2, CtBP1, CoREST, BHC80 and BRAF35, among others, and is essentially identical to the BHC110 complex reported previously (Hakimi et al., 2003). A difference is the presence of CtBP and absence of TFII-I in the LSD1 purification, compared with the previously reported BHC110 complex, but the reason for this discrepancy is currently unclear. The finding above suggested that either posttranslational modifications and/or factors present in the LSD1 complex contribute to the capability of LSD1 to modify a more complex substrate. To address this issue, we first asked whether factors in the LSD1 complex conferred upon LSD1 the ability to demethylate nucleosomal substrates. We investigated whether two LSD1 direct interacting proteins, CoR- EST and BHC80, played a role (Iwase et al., 2004; Jarriault and Greenwald, 2002) (Shi lab, unpubl. result). While the addition of bacterially purified HDAC1 and BHC80 had no effect, addition of CoREST to the demethylation reaction restored the ability of recombinant LSD1 to demethylate nucleosomal substrates. In contrast, CoREST has little stimulatory effect on the LSD1 demethylase activity when assayed on free histones using purified CoREST ranging from 0.3 to 5 μg.

CoREST contains two SANT domains (SANT1 and SANT2), which is a conserved protein motif found in a number of chromatin-associated proteins (Boyer et al., 2004; de la Cruz et al., 2005). The SANT domain in the co-repressor SMRT protein has been shown to preferentially interact with hypoacetylated histone tails (Yu et al., 2003). We speculated that the SANT domain(s) in CoREST might function similarly, thus making CoREST a candidate protein that may bridge the nucleosomal substrates and the demethylase LSD1. Consistent with this model, we found hyperacetylated nucleosomes isolated from HeLa cells treated with the HDAC inhibitor TSA less susceptible to CoREST/LSD1-mediated demethylation (approximately 4 fold difference in demethylation, comparing untreated with TSA-treated nucleosomes). This suggests that the HDACs in the LSD1 complex are likely to function upstream of CoREST/LSD1, generating a hypoacetylated histone substrate, which can then be better recognized by CoREST/LSD1. Further supporting this model, we found that inhibition of HDAC activity by TSA resulted in de-repression of two LSD1 target genes, the human neuronal-specific sodium channel (SCN) genes, SCNA2 and SCNA3. It should be noted that SCN2A expression was previously shown to be unaffected by TSA treatment in the Rat-1 fibroblast cells, suggesting possible species-specific regulation of LSD1 target genes (Lunyak et al., 2002). Regardless, our results suggest that HDACs play an important role in LSD1-mediated repression in vivo, and that HDACs may collaborate with LSD1/CoREST in HeLa cells to repress some of the REST target genes.

We next analyzed a series of N- and C-terminal CoREST deletion mutants (FIG. 3) in order to identify regions of CoREST that are important for stimulating the LSD1 demethylase activity. We found that deletion of the C-terminal region (aa 293 to 482) of CoREST had the most significant effect; i.e., it abrogated about 70% of the stimulatory function of CoREST. Importantly, the same C-terminal region is also sufficient to mediate stimulation of LSD1 demethylation activity to a level that is comparable to that of the wildtype CoREST, while the N-terminal CoREST (aa 1-293) had a weaker stimulatory activity (~30% of the wildtype CoREST activity). Taken together, these findings show that majority of the stimulatory activity of CoREST can be attributed to the C-terminal region of CoREST.

Figure 3:
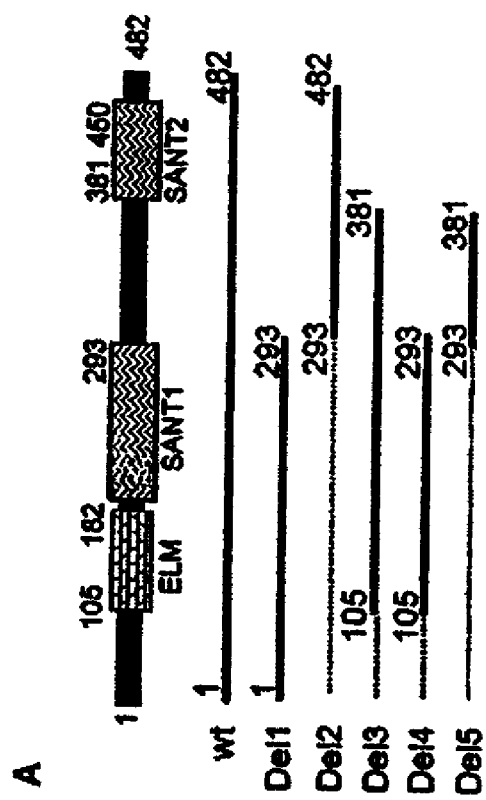
FIG. 3 shows diagrams of CoREST deletion mutants.

To identify domains of CoREST that are involved in physical interactions with LSD1, GST-LSD1 or GST was incubated with bacterially purified, HIS-tagged CoREST and its mutant derivatives. After extensive washing, the bound and the follow-through fractions were analyzed by SDS PAGE and Coomassie Blue staining. As predicted, the C-terminal domain of CoREST, del 2 (aa 293-482), which was sufficient to stimulate LSD1 activity, was also capable of binding LSD1. In addition to del2, del 3 (aa 105-381) and del 5 (aa 293-381) bound LSD1, but del 1 (aa 1-293) and del 4 (aa 105-293) did not, under the same assay conditions. This places the putative LSD1-binding domain within the C-terminal functional domain of CoREST, somewhere between aa 293-381 of CoREST. Interestingly, among the mutants that can bind LSD1 (del2, del3, del5), only del 2 stimulated LSD1 demethylation, indicating that physical interaction with LSD1 alone is not sufficient. A conspicuous difference between del2 and the mutants that bind LSD1 but fail to stimulate its activity is the SANT2 domain, which is present in del2 but not in del3 and del5 (FIG. 3). We therefore speculate that the SANT2 domain may be involved in mediate binding to the nucleosomal substrate. Taken together, these findings are consistent with the idea that CoREST functions as a bridging protein. The weak stimulatory activity of the N-terminal CoREST (del1, aa 1-293) remains unclear at the present time. Although we did not detect LSD1 binding to this region of CoREST, a low level of LSD1-binding activity can't be excluded. Interestingly, this region of CoREST also contains a SANT domain (SANT1), which, as discussed, has the potential to bind histone tails.

Previous studies identified spr-5 and spr-1 as *C. elegans* homologs of LSD1 and CoREST, respectively (Eimer et al., 2002; Jarriault and Greenwald, 2002). Mutations in either spr-5 or spr-1 suppress a presenilin mutation, suggesting that wildtype spr-5 and spr-1 normally function to repress Notch downstream target genes. The two mutations in spr-1 are nonsense mutations that are predicted to generate truncated spr-1 protein lacking the C-terminal region covering the area that corresponds to aa 340 to 482 of mammalian CoREST. Significantly, this is the same region we have shown to be important for stimulating LSD1 activity. Thus, both the genetic and biochemical data argued for a critical requirement of the C-terminal region of CoREST for stimulation of LSD1 activity.

CoREST regulates LSD1 stability in vivo. Having demonstrated that CoREST is crucial for LSD1 to mediate demethylation of nucleosomal substrates in vitro, we next wished to investigate the effect of loss of CoREST on LSD1-mediated transcription in vivo. We first inhibited CoREST expression by RNAi and unexpectedly found that a reduction of CoREST also led to a reduction of LSD1 expression. Immunostaining of cells transfected with a CoREST shRNA plasmid showed that there was not only a significant reduction of CoREST but also LSD1 in ~80% of the CoREST shRNA-transfected cells as compared to control shRNA treated cells. This co-regulation was also observed when the transfected cells were analyzed by Western blotting. We found that the reduction of LSD1 protein expression was not at the RNA level since the LSD1 mRNA level remained the same in the presence or absence of the CoREST shRNA. Consistently, we found that the proteasome inhibitor ZL3VS (Kadlcikova et al., 2004) restored the LSD1 steady state level in CoREST shRNA treated cells close to that of the wildtype cells. Taken together, these findings show that when CoREST is absent or significantly reduced, LSD1 becomes prone to proteasomal degradation, suggesting that CoREST is required for LSD1 stability in vivo. These observations further suggest that there may be yet-to-be-identified mechanisms in place that regulate CoREST expression and/or CoREST/LSD1 interaction, which consequently impact LSD1-mediated H3-K4 demethylation and transcriptional repression. To begin to test this hypothesis, we determined H3-K4 methylation and LSD1 target gene transcription in cells where CoREST level was reduced by RNAi. CoREST shRNA resulted in de-repression of SCN2A and SCN3A, which have previously been shown to be LSD1 target genes (Shi et al., 2004). Importantly, we also observed a significant increase of H3-K4 dimethylation and a concomitant decrease of LSD1 at the target promoters by chromatin immunoprecipitation (ChIP). The reduced LSD1 promoter occupancy is likely to be due to a reduction of the LSD1 protein level in the CoREST shRNA cells.

BHC80 inhibits LSD1 demethylase activity in vitro. In addition to CoREST, the other protein in the LSD1 complex that can directly interact with LSD1, and therefore may influence LSD1 activity, is BHC80 (Hakimi et al., 2002; Iwase et al., 2004). As discussed earlier, BHC80 did not stimulate or inhibit LSD1 activity when it alone was assayed on nucleosomal substrates, under which condition LSD1 was largely inactive. We therefore asked whether BHC80 might exhibit any activity towards LSD1 when LSD1 is actively demethylating histones. While recombinant LSD1 efficiently demethylated H3-K4 on free histones, the addition of recombinant BHC80 significantly dampened this activity. BHC80 remained inhibitory regardless of whether CoREST was present or not in the free histone assays. We next asked whether BHC80 may display the same activity towards the active demethylase unit LSD1/CoREST on nucleosomal substrates. Similarly, while BHC80 had no effect on the inactive LSD1 (LSD1 alone assayed on nucleosomal substrate), increasing amounts of BHC80 caused a proportional decrease in the demethylase activity of LSD1/CoREST assayed on nucleosomal substrates. Thus, in contrast to HDAC1/2 and CoREST, which are positive regulators of LSD1 activity, the in vitro evidence presented above suggests that BHC80 may function to inhibit LSD1 activity.

In summary, we provided evidence in this study that LSD1-mediated histone demethylation is regulated by multiple factors associated with LSD1. CoREST protects LSD1 from proteasomal degradation and also plays an indispensable role for LSD1 to demethylate nucleosomal substrate in vitro. This predicts a critical role for CoREST in LSD1 function in vivo, which is supported by the ChIP data demonstrating that a reduction in the CoREST level significantly affects H3-K4 methylation at the LSD1 target promoters and their repression. HDACs, on the other hand, are implicated in the generation of hypoacetylated nucleosomes, which we show are more susceptible to CoREST/LSD1-mediated histone demethylation. Based on these findings, we speculate that HDACs and LSD1 functionally interact to generate a repressive chromatin environment. Specifically, we suggest that the process of LSD1-mediated H3-K4 demethylation is preceded by HDACs, which cause histone hypoacetylation. The hypoacetylated histone H3 is preferentially recognized by CoREST, which bridges LSD1 to the nucleosomal substrates. Supporting this model, inhibition of HDAC activity by TSA caused de-repression of the LSD1 target genes SCNA2 and SCNA3. Lastly, although the in vivo function of the third component of the LSD1 complex, BHC80, is less clear, the fact that it inhibits LSD1-mediated histone demethylation in vitro suggests a possible negative regulatory mechanism that may provide negative feedback regulation and/or to limit LSD1 activity at the promoter.

The requirement for multiple factors in LSD1-mediated histone demethylation suggests possible dynamic regulation in vivo and predicts that signaling pathways or factors that can modulate LSD1 interactions with other proteins in the LSD1 complex such as CoREST and BHC80 may have profound effects on LSD1 activity in vivo. Importantly, this study has begun to shed light on the individual functions of the factors that are associated with LSD1, and lays the foundation for future exploration of signaling events that modulate these important interactions.

Experimental Procedures

Chemicals, antibodies and other reagents. Proteasome inhibitor ZL3VS was a kind gift from Dr. Hidde Ploegh's Lab (Harvard Medical School, Dept. of Pathology). Histone deacetylase inhibitor Trichostatin A (TSA) was purchased from Sigma. Antibodies (Ab) that recognize different histone modifications, namely anti-diMeK4H3 Ab (UP07-030), anti-diMeK9H3 Ab (UP05-768), anti-panH3Ac Ab (UP06-599), were purchased from Upstate Group, INC (Lake Placid, N.Y.) (UP). Anti-diMeK20H4 antibodies were gifts from Yi Zhang (UP). Bulk histones were purchased from Sigma.

Preparation of mononucleosome. Mononucleosome was made according to a standard protocol (Tagami et al., 2004; Utley et al., 1996). Briefly, nuclear pellet from both TSA-treated or non-treated HeLa cells was homogenized for 60 times with type A pestle to obtain oligo-nucleosomes. The oligo-nucleosomes were then digested with micrococcal nuclease (40 units/ml) for 10 mins at 30° C. The nuclease is inactivated by 5 mM EDTA. Digested materials were spun at 14000 rpm for 3 mins. Resulting supernatant was spun again for additional 3 mins at the same speed. Supernatant from the second spin was subject to 10-25% glycerol gradient sedimentation. The monocleosome-containing fractions were identified by examining aliquots of fractions (treated with proteinase K) on DNA agarose gel. An aliquot of TSA-treated or non TSA-treated mononucleosome, a kind gift from Dr. Yoshihiro Nakatani's Lab in Dana Faber Cancer Institute, Harvard Medical School (Tagami et al., 2004), was used here as a control for the quality of mononucleosome made in our lab.

Recombinant protein expression, purification and GST pulldown assay. His-tagged full length (1-482aa) and deletion mutants of human CoREST were generated by PCR using pcDNA3.1-CoREST-myc plasmid as a template (A kind gift from Dr. Gail Mendal) and cloned into N-terminal 6×His-tag bacterial expression vector and verified by DNA sequencing. The plasmid constructs were transformed into bacteria and the expression of the recombinant proteins was induced by 0.2 mM IPTG at 37° C. for 4 hours. His-tagged proteins were purified by Ni-NTA affinity column (Qiagen, Valencia, Calif.). After washing the column, the bound proteins were eluted from the column by 200 mM imidazole. The eluate was then extensively dialyzed in PBS for 3 times at 4° C. The homogeneity and concentration of the protein were estimated on SDS-PAGE gel followed by Coomassie Blue staining using BSA as standard. The primers used to generate CoREST wt and del mutants are as follows: CoREST-WT:

P1(cccgaattcatggtggagaagggcccccgagt) (SEQ ID NO: 35)+P2 (cccctcgagtcaggaggcagatgcatatct) (SEQ ID NO: 36);

CoREST-Del1: P1+P3(cccctcgaggacctgaggaactgtctcagt) (SEQ ID NO: 37);

CoREST-Del2: P4(cccgaattcactgagacagttcctcaggtc) (SEQ ID NO: 38)+P2;

CoREST-Del3 P5(cccgaattcagggtcggaccccagtacca) (SEQ ID NO: 39)+P6(cccctcgagccaacgtgcattacatttctga) (SEQ ID NO: 40); CoREST-Del4:P5+P3;

CoREST-Del5: P4+P6.

GST and GSTLSD1 plasmids were kind gifts from Dr. Tadashi Baba's Lab in Japan (Iwase et al., 2004). Expression and purification of GST and GSTLSD1 proteins were done using similar procedure as outlined for purification of his-tagged recombinant proteins. For GST-bead pulldown experiment, 2 μg of each purified his-tagged wt or del CoREST proteins were incubated with 5 μg of bound GST and GSTLSD1 proteins at 4° C. for 4 hrs in a binding buffer (50 mM Tris, pH 8.0, 300 mM NaCl, 1 mM DTT, 0.5 mM EDTA and 0.1% NP-40). The beads were washed 3 times in the binding buffer, resuspended in 2×SDS protein sample buffer, boiled for 5 mins and loaded onto 15% SDS PAGE gel. The gel was then stained with Coomassie Blue.

TAP protein complex isolation and identification. The detailed purification procedure has been described previously (Ogawa et al., 2002; Shi et al., 2003). In brief, Flag-HA-tagged human LSD1 was constructed in a retroviral expressing vector. Viruses containing the expressing cassette was made and transduced into HeLa cells. The Flag-HA-LSD1 stable cell line then was established and propagated as suspension cells. Nuclear extract was made from 30L of cells, from which the LSD1 complex was purified by using anti-Flag M2 mAb-conjugated agarose beads (Sigma) followed by anti-HA 12CA5 mAb-conjugated agarose beads in buffer B (100 mM KCl, 20 mM Tris-HCl, pH 7.9, 5 mM $MgCl_2$, 10% glycerol, 1 mM PMSF, 0.1% Nonidet P40, 10 mM 2-mercaptoethanol). The resulting LSD1 associated complex components were identified by MS/MS mass spectrometry as described previously (Shi et al., 2003).

Demethylation assay. LSD1 demethylation activity on free histone or nucleosomal histone was carried out as previously reported (Shi et al., 2004). Briefly, bulk histones or mononucleosomes were incubated with purified His-LSD1 with or without purified His-CoREST, His-CoREST mutants, His-BHC80 and/or GST-HDAC1 in the histone demethylase activity (HDM) assay buffer (50 mM Tris pH8.5, 50 mM KCl, 5 mM MgCl, 0.5% BSA and 5% glycerol) from 10 mins up to 1 hour at 37° C. The demethylase activity of LSD1 under various conditions was evaluated by Western blotting using K4-H3 methylation-specific antibodies.

Knockdown LSD, CoREST and Proteasome inhibitor (PI) treatment. Stable cell lines which express mutant GFP-shRNA, CtBP-shRNA, LSD1-shRNA or CoREST-shRNA were generated as previously described (Shi et al., 2003; Sui et al., 2002). To prevent proteasome-mediated protein degradation, the cells were treated with ZL3VS at final concentration 10 µM for 24 hours in culture then harvested. The protein and mRNA levels of the shRNA-knockdown cells with or without PI treatment were estimated by Western blotting and RT-PCR as previously described (Shi et al., 2004).

REFERENCES

EN.REFLIST

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of screening for modulators of LSD1 or AOF1 activity, comprising:
   contacting a LSD1 or AOF1 protein and a histone peptide in the presence and in the absence of a test substance, wherein the histone peptide is lysine-methylated;
   determining the methylation status of the histone peptide;
   identifying a test substance as an enhancer of LSD1 or AOF1 activity if less methylated lysine is found in the presence than in the absence of the test substance, and identifying a test substance as an inhibitor of LSD1 or AOF1 activity if more methylated lysine is found in the presence than in the absence of the test substance.

2. The method of claim 1, wherein the histone peptide comprises six contiguous amino acid residues of histone H3 which include lysine residue 4.

3. The method of claim 2, wherein the histone peptide is mono-methylated or di-methlyated at lysine residue 4.

4. The method of claim 1, further comprising contacting the LSD1 or AOF1 protein with a CoREST protein or a BHC80 protein.

5. The method of claim 1, wherein the test substance is a small molecule.

6. The method of claim 1, wherein the test substance is a polypeptide or protein.

7. The method of claim 1, wherein the methylation status of the histone peptide is determined by Western blotting or mass spectrometry.

8. The method of claim 1, wherein the contacting occurs in a cell or a cell lysate.

9. A method of screening for modulators of LSD1 activity, comprising:
   contacting a LSD1 protein and a lysine-methlyated histone peptide in the presence and in the absence of a test substance and detecting LSD1 activity.

10. The method of claim 9, wherein the lysine-methylated histone peptide comprises six contiguous amino acid residues of histone H3 which include lysine residue 4.

11. The method of claim 10, wherein the histone peptide is mono-methylated or di-methlyated at lysine residue 4.

12. The method of claim 9, wherein the LSD1 activity is detected by Western blotting, measuring formation of formaldehyde, mass spectrometry, or measuring formation of peroxide.

13. The method of claim 9, further comprising contacting the LSD1 protein with a CoREST protein or a BHC80 protein.

14. The method of claim 9, wherein the test substance is a small molecule.

15. The method of claim 9, wherein the test substance is a polypeptide.

16. The method of claim 9, wherein the contacting occurs within a cell or a cell lysate.

17. The method of claim 9, wherein the test substance is a small molecule.

18. The method of claim 9, wherein the test substance is a polypeptide or protein.

* * * * *

SEQUENCE LISTING

<160> NUMBER OF SEQ ID NOS: 50

<210> SEQ ID NO 1
<211> LENGTH: 20
<212> TYPE: DNA
<213> ORGANISM: Homo sapiens

<400> SEQUENCE: 1
gcgaaatagc agaacaagcc                                                    20

<210> SEQ ID NO 2
<211> LENGTH: 20
<212> TYPE: DNA
<213> ORGANISM: Homo sapiens

<400> SEQUENCE: 2
ctcattgctc gttgcctttg                                                    20

<210> SEQ ID NO 3
<211> LENGTH: 21
<212> TYPE: DNA
<213> ORGANISM: Homo sapiens

<400> SEQUENCE: 3
gatgaggatg atgaaaatgg c                                                  21

<210> SEQ ID NO 4
<211> LENGTH: 25
<212> TYPE: DNA
<213> ORGANISM: Homo sapiens

<400> SEQUENCE: 4
ctaattttct aatagggttg aaggg                                              25

<210> SEQ ID NO 5
<211> LENGTH: 23

```
<212> TYPE: DNA
<213> ORGANISM: Homo sapiens

<400> SEQUENCE: 5
caccacttcc tactttaatg gca                                            23

<210> SEQ ID NO 6
<211> LENGTH: 22
<212> TYPE: DNA
<213> ORGANISM: Homo sapiens

<400> SEQUENCE: 6
aaatagagac aggaaagccc ag                                             22

<210> SEQ ID NO 7
<211> LENGTH: 19
<212> TYPE: DNA
<213> ORGANISM: Homo sapiens

<400> SEQUENCE: 7
ggcgatcaag aagctgtcc                                                 19

<210> SEQ ID NO 8
<211> LENGTH: 20
<212> TYPE: DNA
<213> ORGANISM: Homo sapiens

<400> SEQUENCE: 8
caccttggga ccagtgtacc                                                20

<210> SEQ ID NO 9
<211> LENGTH: 19
<212> TYPE: DNA
<213> ORGANISM: Homo sapiens

<400> SEQUENCE: 9
gaaggtgaag gtcggagtc                                                 19

<210> SEQ ID NO 10
<211> LENGTH: 20
<212> TYPE: DNA
<213> ORGANISM: Homo sapiens

<400> SEQUENCE: 10
gaagatggtg atgggatttc                                                20

<210> SEQ ID NO 11
<211> LENGTH: 20
<212> TYPE: DNA
<213> ORGANISM: Homo sapiens

<400> SEQUENCE: 11
gaacagaaca cctccctcca                                                20

<210> SEQ ID NO 12
<211> LENGTH: 20
<212> TYPE: DNA
<213> ORGANISM: Homo sapiens

<400> SEQUENCE: 12
gagtcagaag gcaggacagg                                                20

<210> SEQ ID NO 13
```

```
<211> LENGTH: 20
<212> TYPE: DNA
<213> ORGANISM: Homo sapiens

<400> SEQUENCE: 13
taaagcccag tcaagacagc                                              20

<210> SEQ ID NO 14
<211> LENGTH: 20
<212> TYPE: DNA
<213> ORGANISM: Homo sapiens

<400> SEQUENCE: 14
gacacaccca gaagatggag                                              20

<210> SEQ ID NO 15
<211> LENGTH: 20
<212> TYPE: DNA
<213> ORGANISM: Homo sapiens

<400> SEQUENCE: 15
cgtgtttcaa ggctacagca                                              20

<210> SEQ ID NO 16
<211> LENGTH: 20
<212> TYPE: DNA
<213> ORGANISM: Homo sapiens

<400> SEQUENCE: 16
ctctagcctc ccaaccttcc                                              20

<210> SEQ ID NO 17
<211> LENGTH: 20
<212> TYPE: DNA
<213> ORGANISM: Homo sapiens

<400> SEQUENCE: 17
ctctgtcaca gggaggaaag                                              20

<210> SEQ ID NO 18
<211> LENGTH: 20
<212> TYPE: DNA
<213> ORGANISM: Homo sapiens

<400> SEQUENCE: 18
agactagagc aggccacaag                                              20

<210> SEQ ID NO 19
<211> LENGTH: 20
<212> TYPE: DNA
<213> ORGANISM: Homo sapiens

<400> SEQUENCE: 19
ccgtggtgtt gttgaaactg                                              20

<210> SEQ ID NO 20
<211> LENGTH: 20
<212> TYPE: DNA
<213> ORGANISM: Homo sapiens

<400> SEQUENCE: 20
tgtccggtgg tggactcttc                                              20
```

<210> SEQ ID NO 21
<211> LENGTH: 20
<212> TYPE: DNA
<213> ORGANISM: Homo sapiens

<400> SEQUENCE: 21
tcctcctgtt tcatccaagc                                                    20

<210> SEQ ID NO 22
<211> LENGTH: 20
<212> TYPE: DNA
<213> ORGANISM: Homo sapiens

<400> SEQUENCE: 22
tagtagccgg gccctacttt                                                    20

<210> SEQ ID NO 23
<211> LENGTH: 886
<212> TYPE: PRT
<213> ORGANISM: Homo sapiens

<400> SEQUENCE: 23

Arg Arg Ala Gly Ser Val Lys Arg Gly Glu Ala Arg Leu Phe Gly Pro
 1               5                  10                  15

Thr Glu Arg Gln Ser Glu Arg Pro Leu Arg Pro Ser Ala Ala Arg Arg
            20                  25                  30

Pro Glu Met Leu Ser Gly Lys Lys Ala Ala Ala Ala Ala Ala Ala Ala
        35                  40                  45

Ala Ala Ala Ala Thr Gly Thr Glu Ala Gly Pro Gly Thr Ala Gly Gly
    50                  55                  60

Ser Glu Asn Gly Ser Glu Val Ala Ala Gln Pro Ala Gly Leu Ser Gly
65                  70                  75                  80

Pro Ala Glu Val Gly Pro Gly Ala Val Gly Glu Arg Thr Pro Arg Lys
                85                  90                  95

Lys Glu Pro Pro Arg Ala Ser Pro Pro Gly Gly Leu Ala Glu Pro Pro
            100                 105                 110

Gly Ser Ala Gly Pro Gln Ala Gly Pro Thr Val Val Pro Gly Ser Ala
        115                 120                 125

Thr Pro Met Glu Thr Gly Ile Ala Glu Thr Pro Glu Gly Arg Arg Thr
    130                 135                 140

Ser Arg Arg Lys Arg Ala Lys Val Glu Tyr Arg Glu Met Asp Glu Ser
145                 150                 155                 160

Leu Ala Asn Leu Ser Glu Asp Glu Tyr Tyr Ser Glu Glu Glu Arg Asn
                165                 170                 175

Ala Lys Ala Glu Lys Glu Lys Lys Leu Pro Pro Pro Pro Gln Ala
            180                 185                 190

Pro Pro Glu Glu Glu Asn Glu Ser Glu Pro Glu Glu Pro Ser Gly Val
        195                 200                 205

Glu Gly Ala Ala Phe Gln Ser Arg Leu Pro His Asp Arg Met Thr Ser
    210                 215                 220

Gln Glu Ala Ala Cys Phe Pro Asp Ile Ile Ser Gly Pro Gln Gln Thr
225                 230                 235                 240

Gln Lys Val Phe Leu Phe Ile Arg Asn Arg Thr Leu Gln Leu Trp Leu
                245                 250                 255

Asp Asn Pro Lys Ile Gln Leu Thr Phe Glu Ala Thr Leu Gln Gln Leu
            260                 265                 270

Glu Ala Pro Tyr Asn Ser Asp Thr Val Leu Val His Arg Val His Ser

-continued

```
            275                 280                 285
Tyr Leu Glu Arg His Gly Leu Ile Asn Phe Gly Ile Tyr Lys Arg Ile
290                 295                 300
Lys Pro Leu Pro Thr Lys Lys Thr Gly Lys Val Ile Ile Ile Gly Ser
305                 310                 315                 320
Gly Val Ser Gly Leu Ala Ala Ala Arg Gln Leu Gln Ser Phe Gly Met
                325                 330                 335
Asp Val Thr Leu Leu Glu Ala Arg Asp Arg Val Gly Gly Arg Val Ala
            340                 345                 350
Thr Phe Arg Lys Gly Asn Tyr Val Ala Asp Leu Gly Ala Met Val Val
        355                 360                 365
Thr Gly Leu Gly Gly Asn Pro Met Ala Val Val Ser Lys Gln Val Asn
370                 375                 380
Met Glu Leu Ala Lys Ile Lys Gln Lys Cys Pro Leu Tyr Glu Ala Asn
385                 390                 395                 400
Gly Gln Ala Val Pro Lys Glu Lys Asp Glu Met Val Glu Gln Glu Phe
                405                 410                 415
Asn Arg Leu Leu Glu Ala Thr Ser Tyr Leu Ser His Gln Leu Asp Phe
            420                 425                 430
Asn Val Leu Asn Asn Lys Pro Val Ser Leu Gly Gln Ala Leu Glu Val
        435                 440                 445
Val Ile Gln Leu Gln Glu Lys His Val Lys Asp Glu Gln Ile Glu His
450                 455                 460
Trp Lys Lys Ile Val Lys Thr Gln Glu Glu Leu Lys Glu Leu Leu Asn
465                 470                 475                 480
Lys Met Val Asn Leu Lys Glu Lys Ile Lys Glu Leu His Gln Gln Tyr
                485                 490                 495
Lys Glu Ala Ser Glu Val Lys Pro Pro Arg Asp Ile Thr Ala Glu Phe
            500                 505                 510
Leu Val Lys Ser Lys His Arg Asp Leu Thr Ala Leu Cys Lys Glu Tyr
        515                 520                 525
Asp Glu Leu Ala Glu Thr Gln Gly Lys Leu Glu Glu Lys Leu Gln Glu
530                 535                 540
Leu Glu Ala Asn Pro Pro Ser Asp Val Tyr Leu Ser Ser Arg Asp Arg
545                 550                 555                 560
Gln Ile Leu Asp Trp His Phe Ala Asn Leu Glu Phe Ala Asn Ala Thr
                565                 570                 575
Pro Leu Ser Thr Leu Ser Leu Lys His Trp Asp Gln Asp Asp Asp Phe
            580                 585                 590
Glu Phe Thr Gly Ser His Leu Thr Val Arg Asn Gly Tyr Ser Cys Val
        595                 600                 605
Pro Val Ala Leu Ala Glu Gly Leu Asp Ile Lys Leu Asn Thr Ala Val
610                 615                 620
Arg Gln Val Arg Tyr Thr Ala Ser Gly Cys Glu Val Ile Ala Val Asn
625                 630                 635                 640
Thr Arg Ser Thr Ser Gln Thr Phe Ile Tyr Lys Cys Asp Ala Val Leu
                645                 650                 655
Cys Thr Leu Pro Leu Gly Val Leu Lys Gln Gln Pro Pro Ala Val Gln
            660                 665                 670
Phe Val Pro Pro Leu Pro Glu Trp Lys Thr Ser Ala Val Gln Arg Met
        675                 680                 685
Gly Phe Gly Asn Leu Asn Lys Val Val Leu Cys Phe Asp Arg Val Phe
690                 695                 700
```

-continued

```
Trp Asp Pro Ser Val Asn Leu Phe Gly His Val Gly Ser Thr Thr Ala
705                 710                 715                 720
Ser Arg Gly Glu Leu Phe Leu Phe Trp Asn Leu Tyr Lys Ala Pro Ile
            725                 730                 735
Leu Leu Ala Leu Val Ala Gly Glu Ala Ala Gly Ile Met Glu Asn Ile
        740                 745                 750
Ser Asp Val Ile Val Gly Arg Cys Leu Ala Ile Leu Lys Gly Ile
        755                 760                 765
Phe Gly Ser Ser Ala Val Pro Gln Pro Lys Glu Thr Val Val Ser Arg
770                 775                 780
Trp Arg Ala Asp Pro Trp Ala Arg Gly Ser Tyr Ser Tyr Val Ala Ala
785                 790                 795                 800
Gly Ser Ser Gly Asn Asp Tyr Asp Leu Met Ala Gln Pro Ile Thr Pro
                805                 810                 815
Gly Pro Ser Ile Pro Gly Ala Pro Gln Pro Ile Pro Arg Leu Phe Phe
            820                 825                 830
Ala Gly Glu His Thr Ile Arg Asn Tyr Pro Ala Thr Val His Gly Ala
        835                 840                 845
Leu Leu Ser Gly Leu Arg Glu Ala Gly Arg Ile Ala Asp Gln Phe Leu
850                 855                 860
Gly Ala Met Tyr Thr Leu Pro Arg Gln Ala Thr Pro Gly Val Pro Ala
865                 870                 875                 880
Gln Gln Ser Pro Ser Met
                885

<210> SEQ ID NO 24
<211> LENGTH: 2985
<212> TYPE: DNA
<213> ORGANISM: Homo sapiens

<400> SEQUENCE: 24
cggcgcgcgg gcagcgtgaa gcgaggcgag gcaaggcttt tcggacccac ggagcgacag      60
agcgagcggc ccctacggcc gtcggcggcc cggcggcccg agatgttatc tgggaagaag     120
gcggcagccg cggcggcggc ggctgcagcg gcagcaaccg ggacggaggc tggccctggg     180
acagcaggcg gctccgagaa cgggtctgag gtggccgcgc agcccgcggg cctgtcgggc     240
ccagccgagg tcgggccggg ggcggtgggg gagcgcacac cccgcaagaa agagcctccg     300
cgggcctcgc cccccggggg cctggcgaaa ccgccggggt ccgcagggcc tcaggccggc     360
cctactgtcg tgcctgggtc tgcgaccccc atggaaactg aatagcaga gactccggag      420 gggcgtcgga ccagccggcg caagcgggcg aaggtagagt acagagagat ggatgaaagc     480
ttggccaacc tctcagaaga tgagtattat tcagaagaag agagaaatgc aaagcagag      540 aaggaaaaga agcttccccc accaccccct caagccccac ctgaggaaga aaatgaaagt     600
gagcctgaag aaccatcggg tgtggagggc gcagctttcc agagccgact tcctcatgac     660
cggatgactt ctcaagaagc agcctgtttt ccagatatta tcagtggacc acaacagacc     720
cagaaggttt ttcttttcat tagaaaccgc acactgcagt tgtggttgga taatccaaag     780
attcagctga catttgaggc tactctccaa caattagaag cacttataaa cagtgatact     840
gtgcttgtcc accgagttca cagttattta gagcgtcatg gtcttatcaa cttcggcatc     900
tataaggagg taaaccccct accaactaaa aagacaggaa aggtaattat tataggctct     960
ggggtctcag gcttggcagc agctcgacag ttacaaagtt ttggaatgga tgtcacactt    1020
```

-continued

```
ttggaagcca gggatcgtgt gggtggacga gttgccacat ttcgcaaagg aaactatgta    1080
gctgatcttg gagccatggt ggtaacaggt cttggaggga atcctatggc tgtggtcagc    1140
aaacaagtaa atatggaact ggccaagatc aagcaaaaat gcccacttta tgaagccaac    1200
ggacaagctg ttcctaaaga gaaagatgaa atggtagagc aagagtttaa ccggttgcta    1260
gaagctacat cttaccttag tcatcaacta gacttcaatg tcctcaataa taagcctgtg    1320
tcccttggcc aggcattgga agttgtcatt cagttacaag agaagcatgt caaagatgag    1380
cagattgaac attggaagaa gatagtgaaa actcaggaag aattgaaaga acttcttaat    1440
aagatggtaa atttgaaaga gaaaattaaa gaactccatc agcaatacaa agaagcatct    1500
gaagtaaagc cacccagaga tattactgcc gagttcttag tgaaaagcaa acacagggat    1560
ctgaccgccc tatgcaagga atatgatgaa ttagctgaaa cacaaggaaa gctagaagaa    1620
aaacttcagg agttggaagc gaatcccccca agtgatgtat atctctcatc aagagacaga    1680
caaatacttg attggcattt tgcaaatctt gaatttgcta atgccacacc tctctcaact    1740
ctctccctta agcactggga tcaggatgat gactttgagt tcactggcag ccacctgaca    1800
gtaaggaatg ctactcgtg tgtgcctgtg gctttagcag aaggcctaga cattaaactg    1860
aatacagcag tgcgacaggt tcgctacacg gcttcaggat gtgaagtgat agctgtgaat    1920
acccgctcca cgagtcaaac ctttatttat aaatgcgacg cagttctctg tacccttccc    1980
ctgggtgtgc tgaagcagca gccaccagcc gttcagtttg tgccacctct ccctgagtgg    2040
aaaacatctg cagtccaaag gatgggattt ggcaaccta acaaggtggt gttgtgtttt    2100
gatcgggtgt tctgggatcc aagtgtcaat ttgttcgggc atgttggcag tacgactgcc    2160
agcaggggtg agctcttcct cttctggaac ctctataaag ctccaatact gttggcacta    2220
gtggcaggag aagctgctgg tatcatggaa aacataagtg acgatgtgat tgttggccga    2280
tgcctggcca ttctcaaagg gatttttggt agcagtgcag tacctcagcc caaagaaact    2340
gtggtgtctc gttggcgtgc tgatccctgg gctcgggct cttattccta tgttgctgca    2400
ggatcatctg gaaatgacta tgatttaatg gctcagccaa tcactcctgg ccctcgatt    2460 ccaggtgccc cacagccgat tccacgactc ttctttgcgg gagaacatac gatccgtaac    2520
tacccagcca cagtgcatgg tgctctgctg agtgggctgc gagaagcggg aagaattgca    2580
gaccagtttt tgggggccat gtatacgctg cctcgccagg ccacaccagg tgttcctgca    2640
cagcagtccc caagcatgtg agacagatgc attctaaggg aagaggccca tgtgcctgtt    2700
tctgccatgt aaggaaggct cttctagcaa tactagatcc cactgagaaa atccaccctg    2760
gcatctgggc tcctgatcag ctgatggagc tcctgatttg acaaaggagc ttgcctcctt    2820
tgaatgacct agagcacagg gaggaacttg tccattagtt tggaattgtg ttcttcgtaa    2880
agactgaggc aagcaagtgc tgtgaaataa catcatctta gtcccttggt gtgtgggtt    2940 tgttttttt tttatatttt gagaataaaa cttcatataa aattg                    2985
```

<210> SEQ ID NO 25
<211> LENGTH: 136
<212> TYPE: PRT
<213> ORGANISM: Homo sapiens

<400> SEQUENCE: 25

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

```
Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135

<210> SEQ ID NO 26
<211> LENGTH: 790
<212> TYPE: PRT
<213> ORGANISM: Homo sapiens

<400> SEQUENCE: 26

Met Gly Arg Ala Glu Arg Ala Leu Arg Leu Lys Arg Arg Arg Gly Pro
 1               5                  10                  15

Tyr Pro Ser Leu Val Leu Ser Ala Pro Pro Thr Pro Gly His Ala Val
                20                  25                  30

Thr Gly Ala Glu Ala Ala Ala Ala Ala Ala Glu Lys Arg Leu Gly
            35                  40                  45

Leu Ala Ala Arg Leu Gln Pro Ser Cys Ala Arg Gly Ala Arg Leu Arg
        50                  55                  60

Arg Gly Ala Arg Ser Pro Gly Arg Arg Ala Pro Pro Arg Trp Arg Ser
 65                  70                  75                  80

Glu Arg Cys Leu Phe Pro Glu Thr Pro Gly Thr Ser Ser Ala Gln Arg
                85                  90                  95

Leu Phe Asn Val Met Ala Thr Pro Arg Gly Arg Thr Lys Lys Lys Ala
            100                 105                 110

Ser Phe Asp His Ser Pro Asp Ser Leu Pro Leu Arg Ser Ser Gly Arg
        115                 120                 125

Gln Ala Lys Lys Lys Ala Thr Glu Thr Thr Asp Glu Asp Glu Asp Gly
        130                 135                 140

Gly Ser Glu Lys Lys Tyr Arg Lys Cys Glu Lys Ala Gly Cys Thr Ala
145                 150                 155                 160

Thr Cys Pro Val Cys Phe Ala Ser Ala Ser Glu Arg Cys Ala Lys Asn
                165                 170                 175

Gly Tyr Thr Ser Arg Trp Tyr His Leu Ser Cys Gly Glu His Phe Cys
            180                 185                 190

Asn Glu Cys Phe Asp His Tyr Tyr Arg Ser His Lys Asp Gly Tyr Asp
        195                 200                 205

Lys Tyr Thr Thr Trp Lys Lys Ile Trp Thr Ser Asn Gly Lys Thr Glu
        210                 215                 220

Pro Ser Pro Lys Ala Phe Met Ala Asp Gln Gln Leu Pro Tyr Trp Val
225                 230                 235                 240

Gln Cys Thr Lys Pro Glu Cys Arg Lys Trp Arg Gln Leu Thr Lys Glu
                245                 250                 255

Ile Gln Leu Thr Pro Gln Ile Ala Lys Thr Tyr Arg Cys Gly Met Lys
```

```
            260                 265                 270
Pro Asn Thr Ala Ile Lys Pro Glu Thr Ser Asp His Cys Ser Leu Pro
        275                 280                 285
Glu Asp Leu Glu Ala Leu Thr Pro Gln Lys Cys Ile Pro His Ile Ile
    290                 295                 300
Val Arg Gly Leu Val Arg Ile Arg Cys Val Gln Val Glu Arg Ile
305                 310                 315                 320
Leu Tyr Phe Met Thr Arg Lys Gly Leu Ile Asn Thr Gly Val Leu Ser
                325                 330                 335
Val Gly Ala Asp Gln Tyr Leu Leu Pro Lys Asp Tyr His Asn Lys Ser
            340                 345                 350
Val Ile Ile Ile Gly Ala Gly Pro Ala Gly Leu Ala Ala Arg Gln
            355                 360                 365
Leu His Asn Phe Gly Ile Lys Val Thr Val Leu Glu Ala Lys Asp Arg
    370                 375                 380
Ile Gly Gly Arg Val Trp Asp Asp Lys Ser Phe Lys Gly Val Thr Val
385                 390                 395                 400
Gly Arg Gly Ala Gln Ile Val Asn Gly Cys Ile Asn Asn Pro Val Ala
                405                 410                 415
Leu Met Cys Glu Gln Leu Gly Ile Ser Met His Lys Phe Gly Glu Arg
            420                 425                 430
Cys Asp Leu Ile Gln Glu Gly Arg Ile Thr Asp Pro Thr Ile Asp
            435                 440                 445
Lys Arg Met Asp Phe His Phe Asn Ala Leu Leu Asp Val Val Ser Glu
    450                 455                 460
Trp Arg Lys Asp Lys Thr Gln Leu Gln Asp Val Pro Leu Gly Glu Lys
465                 470                 475                 480
Ile Glu Glu Ile Tyr Lys Ala Phe Ile Lys Glu Ser Gly Ile Gln Phe
                485                 490                 495
Ser Glu Leu Glu Gly Gln Val Leu Gln Phe His Leu Ser Asn Leu Glu
            500                 505                 510
Tyr Ala Cys Gly Ser Asn Leu His Gln Val Ser Ala Arg Ser Trp Asp
            515                 520                 525
His Asn Glu Phe Phe Ala Gln Phe Ala Gly Asp His Thr Leu Leu Thr
    530                 535                 540
Pro Gly Tyr Ser Val Ile Glu Lys Leu Ala Glu Gly Leu Asp Ile
545                 550                 555                 560
Gln Leu Lys Ser Pro Val Gln Cys Ile Asp Tyr Ser Gly Asp Glu Val
                565                 570                 575
Gln Val Thr Thr Thr Asp Gly Thr Gly Tyr Ser Ala Gln Lys Val Leu
            580                 585                 590
Val Thr Val Pro Leu Ala Leu Leu Gln Lys Gly Ala Ile Gln Phe Asn
            595                 600                 605
Pro Pro Leu Ser Glu Lys Lys Met Lys Ala Ile Asn Ser Leu Gly Ala
    610                 615                 620
Gly Ile Ile Glu Lys Ile Ala Leu Gln Phe Pro Tyr Arg Phe Trp Asp
625                 630                 635                 640
Ser Lys Val Gln Gly Ala Asp Phe Phe Gly His Val Pro Pro Ser Ala
                645                 650                 655
Ser Lys Arg Gly Leu Phe Ala Val Phe Tyr Asp Met Asp Pro Gln Lys
            660                 665                 670
Lys His Ser Val Leu Met Ser Val Ile Ala Gly Glu Ala Val Ala Ser
    675                 680                 685
```

```
Val Arg Thr Leu Asp Asp Lys Gln Val Leu Gln Cys Met Ala Thr
    690                 695                 700

Leu Arg Glu Leu Phe Lys Glu Gln Glu Val Pro Asp Pro Thr Lys Tyr
705                 710                 715                 720

Phe Val Thr Arg Trp Ser Thr Asp Pro Trp Ile Gln Met Ala Tyr Ser
                725                 730                 735

Phe Val Lys Thr Gly Ser Gly Glu Ala Tyr Asp Ile Ile Ala Glu
            740                 745                 750

Asp Ile Gln Gly Thr Val Phe Phe Ala Gly Glu Ala Thr Asn Arg His
        755                 760                 765

Phe Pro Gln Thr Val Thr Gly Ala Tyr Leu Ser Gly Val Arg Glu Ala
    770                 775                 780

Ser Lys Ile Ala Ala Phe
785                 790

<210> SEQ ID NO 27
<211> LENGTH: 4234
<212> TYPE: DNA
<213> ORGANISM: Homo sapiens

<400> SEQUENCE: 27
atgggcaggg cggagcgagc gctgcggcta aagcgaaggc ggggacccta cccatccta      60 gtcctgtcgg ctcctcccac cccgggtcac gccgtgacag gggcggaagc ggcggcggcg    120
gcggcggccg agaagaggct ggggctcgcg gcgcggctgc agccgtcctg tgcgcgcggc    180
gcgcggctcc ggagaggcgc ccgcagtcca gggcggcgcg caccgcctcg ctggcgctca    240
gagcggtgcc ttttccccga gactcccggc acctcttcag cgcaaagatt atttaatgta    300
atggcaactc cacggggggag gacaaagaaa aaagcatctt ttgatcattc tccggatagc    360
cttcctttga ggagctccgg taggcaggcg aagaagaaag caacagagac aacagatgag    420
gatgaagatg gtggctcaga agaagaagtac aggaaatgtg aaaaggcagg ctgtacggca    480
acatgtcctg tgtgcttttgc aagtgcttct gaaagatgtg ccaaaaatgg ctacacctcc    540
cgatggtatc atctctcctg tgggaacat ttctgtaatg aatgctttga ccattactac    600
agaagccata aggatggata tgacaaatat actacatgga aaaaaatatg gactagcaat    660
ggcaaaaccg aacctagtcc caaagctttc atggcagacc agcaactccc ctactgggtt    720
cagtgtacaa aacctgagtg tagaaaatgg aggcagctta ccaaggaaat ccagcttact    780
ccacagatag ccaagactta tcgatgcggt atgaaaccaa atactgctat taagcctgag    840
acctcagatc attgttccct cccagaggat ctagaagctc ttactcctca gaaatgtatt    900
cctcacatca tcgtccgggg tctcgtgcgt attcgatgcg ttcaggaagt ggagagaata    960
ctgtatttta tgaccagaaa aggtctcatc aacactggag ttctcagcgt gggagccgac   1020
cagtatcttc tccctaagga ctaccacaat aaatcagtca tcattatcgg ggctggtcca   1080
gcaggattag cagctgctag caactgcat aactttggaa ttaaggtgac tgtcctggaa   1140
gccaaagaca gaattggagg ccgagtctgg gatgataaat cttttaaagg cgtcacagtg   1200
ggaagaggag ctcagattgt caatgggtgt attaacaacc cagtagcatt aatgtgtgaa   1260
caacttggca tcagcatgca taaatttgga gaaagatgtg acttaattca ggaaggtgga   1320
agaataactg accccactat tgacaagcgc atggatttc attttaatgc tctcttggat   1380
gttgtctctg agtggagaaa ggataagact cagctccaag atgtccccttt aggagaaaag   1440 atagaagaaa tctacaaggc atttattaag gaatctggta tccaattcag tgagctggag   1500
```

-continued

```
ggacaggtgc ttcagttcca tctcagtaac ctggagtacg cctgtggcag caaccttcac    1560
caggtatctg ctcgctcgtg ggaccacaat gaattctttg cccagtttgc tggtgaccac    1620
actctgctaa ctcccgggta ctcggtgata attgaaaaac tggcagaagg cttgacatt    1680 caactcaaat ctccagtgca gtgtattgat tattctggag atgaagtgca ggttaccact    1740
acagatggca cagggtattc tgcacaaaag gtattagtca ctgtaccact ggctttacta    1800
cagaaaggtg ccattcagtt taatccaccg ttgtcagaga agaagatgaa ggctatcaac    1860
agcttaggcg caggcatcat tgaaaagatt gccttgcaat ttccgtatag attttgggac    1920
agtaaagtac aaggggctga cttttttggt cacgttcctc ccagtgccag caagcgaggg    1980 cttttttgccg tgttctatga catggatccc cagaagaagc acagcgtgct gatgtctgtg    2040
attgccgggg aggctgtcgc atccgtgagg accctggatg acaaacaggt gctgcagcag    2100
tgcatggcca cgctccggga gctgttcaag gagcaggagg tcccagatcc cacaaagtat    2160
tttgtcactc ggtggagcac agacccatgg atccagatgg catacagttt tgtgaagaca    2220
ggtggaagtg gggaggccta cgatatcatt gctgaagaca ttcaaggaac cgtcttttc    2280 gctggtgagg caacaaacag gcatttccca caaactgtta caggggcata tttgagtggc    2340
gttcgagaag caagcaagat tgcagcattt taagaattcg gtggacccag ctttcttctg    2400
taccccagat ggggaaattt gaatcacatg ttaaacctca gttttataag aggggggaaaa    2460 aaccgtctct acatagtaaa actgaaatgt ttctaaggcg atatgataat gcaaacctat    2520
ttcatcactc taaaagcact gacctcaaaa aaccttataa gcacttagat ttaattgcat    2580
tttccatagg ttcaactact gctgaaagtc tggatttcag aataaagcag aatgtaagtt    2640
tcagttgagg ccatggattt gattgttcca tggctggaag ttcccttag atttcacatt    2700 ttatatggct gatcaatttt catacattga gaaaccaagt caatcaagca ggaatcattt    2760
aaaaaccaga taaagccatg tttttcttct gtgacaattt atcagtatct ttaccaatga    2820
gccttaattt ttatataggt ccaatattga gcttttactt aaaatttaga tagaacttt    2880 ttttggatac agcacaaact ccagttgaca gtaaaatgaa gcttctaggt attttgtatt    2940
gtacatattt cctcctactg ggtgttcaaa agaaatttaa attcaagtac cttttgtgat    3000
aaaatgtttt agatttgtgc acccattggc aaaacaggaa agtttccaga taggtattgt    3060
atcattgaga atgcagcaca gatagtgtgg gcttcacact atagacacag aatatagctt    3120
tttcttaaag ccaaatttgg gtgataggac actttaaata tccttaattt tggcaaccac    3180
tagcaaaaaa acttgtcaga ataatttaac caagcccctc tccacttctt ttatttaaaa    3240
gcactgattc aattgctagg aatatttttg cagattttc tttacagtat tccataggca    3300
ggtccactgg aaaactgcag aaaaatgtga gctctcctgg taaatagtat acattttata    3360
agctatattt taaaggccta agaacatggc aagtatttac ttttatcttt ttttaaaaa    3420 cactcatgac agaaaacagt ttaataatat ctcattctaa aataaaacac tggttgcagg    3480
gtcttcagga tgcctatttt gccaagaaac ttcagtatac aggttagaaa tatgcttttg    3540
tttttgaaca ataatatact ggtttgcttt aagaagggaa ctaaatatga ctttaaagag    3600
acttcaaaat attgagtatt ttaaaaattt aaaagtaggt cagtttataa cgagtaaata    3660
cctaacacac caagaatgtg cagtgaacct caggcattta agacacctcc cccaccgccc    3720 gcccccgcc ccccccaatc aaagtgtggt cccaaaacaa gccaacagct gtatatctca    3780
aaagttaacc caagacaact ctgatattta ggttatttgt tgagactcat tggtactgac    3840
```

-continued

```
tggcaagtat tctgctttaa agtatcatgt attaaaatgt ttagacagca tgtgttttaa      3900
agtgataaat gcaaaatgtt aagtttgaaa tggttaacag taaattatta tgttagtttc      3960
caggcacttg aactgtgcta caagtagggg aaaacctact ttaaagtatg gtaaatgtgt      4020
gttttaaact tcctatcaag tgacatactt catttgattt tttgtttaag aagccatggt      4080
acttttttct tgagttactt tggatatgtt ttttcaatgc catctgaaga tttttgtaatt     4140 gagtagcagt aaatatacag atttacaatg ttttaactac agttcatgaa tagctggttg      4200
tgtaaaacta ataaaaaact agactttcac atgt                                  4234
```

<210> SEQ ID NO 28
<211> LENGTH: 3102
<212> TYPE: DNA
<213> ORGANISM: Homo sapiens
<220> FEATURE:
<221> NAME/KEY: CDS
<222> LOCATION: (145)..(2772)

<400> SEQUENCE: 28

```
ggcgggagcg cgcttggcgc gtgcgtacgc gacggcggtt ggcggcgcgc gggcagcgtg       60
aagcgaggcg aggcaaggct tttcggaccc acggagcgac agagcgagcg gcccctacgg      120
ccgtcggcgg cccggcggcc cgag atg tta tct ggg aag aag gcg gca gcc         171
                             Met Leu Ser Gly Lys Lys Ala Ala Ala
                               1               5 gcg gcg gcg gcg gct gca gcg gca gca acc ggg acg gag gct ggc cct        219
Ala Ala Ala Ala Ala Ala Ala Ala Ala Thr Gly Thr Glu Ala Gly Pro
 10                  15                  20                  25 ggg aca gca ggc ggc tcc gag aac ggg tct gag gtg gcc gcg cag ccc        267
Gly Thr Ala Gly Gly Ser Glu Asn Gly Ser Glu Val Ala Ala Gln Pro
                 30                  35                  40 gcg ggc ctg tcg ggc cca gcc gag gtc ggg ccg ggg gcg gtg ggg gag        315
Ala Gly Leu Ser Gly Pro Ala Glu Val Gly Pro Gly Ala Val Gly Glu
             45                  50                  55 cgc aca ccc cgc aag aaa gag cct ccg cgg gcc tcg ccc ccc ggg ggc        363
Arg Thr Pro Arg Lys Lys Glu Pro Pro Arg Ala Ser Pro Pro Gly Gly
         60                  65                  70 ctg gcg gaa ccg ccg ggg tcc gca ggg cct cag gcc ggc cct act gtc        411
Leu Ala Glu Pro Pro Gly Ser Ala Gly Pro Gln Ala Gly Pro Thr Val
     75                  80                  85 gtg cct ggg tct gcg acc ccc atg gaa act gga ata gca gag act ccg        459
Val Pro Gly Ser Ala Thr Pro Met Glu Thr Gly Ile Ala Glu Thr Pro
 90                  95                 100                 105 gag ggg cgt cgg acc agc cgg cgc aag cgg gcg aag gta gag tac aga        507
Glu Gly Arg Arg Thr Ser Arg Arg Lys Arg Ala Lys Val Glu Tyr Arg
                110                 115                 120 gag atg gat gaa agc ttg gcc aac ctc tca gaa gat gag tat tat tca        555
Glu Met Asp Glu Ser Leu Ala Asn Leu Ser Glu Asp Glu Tyr Tyr Ser
            125                 130                 135 gaa gag gag aga aat gcc aaa gca gag aag gaa aag aag ctt ccc cca        603
Glu Glu Glu Arg Asn Ala Lys Ala Glu Lys Glu Lys Lys Leu Pro Pro
        140                 145                 150 cca ccc cct caa gcc cca cct gag gaa gaa aat gaa agt gag cct gaa        651
Pro Pro Pro Gln Ala Pro Pro Glu Glu Glu Asn Glu Ser Glu Pro Glu
    155                 160                 165 gaa cca tcg ggg caa gca gga gga ctt caa gac gac agt tct gga ggg        699
Glu Pro Ser Gly Gln Ala Gly Gly Leu Gln Asp Asp Ser Ser Gly Gly
170                 175                 180                 185 tat gga gac ggc caa gca tca ggt gtg gag ggc gca gct ttc cag agc        747
Tyr Gly Asp Gly Gln Ala Ser Gly Val Glu Gly Ala Ala Phe Gln Ser
```

-continued

```
                   190                 195                 200
cga ctt cct cat gac cgg atg act tct caa gaa gca gcc tgt ttt cca    795
Arg Leu Pro His Asp Arg Met Thr Ser Gln Glu Ala Ala Cys Phe Pro
            205                 210                 215 gat att atc agt gga cca caa cag acc cag aag gtt ttt ctt ttc att    843
Asp Ile Ile Ser Gly Pro Gln Gln Thr Gln Lys Val Phe Leu Phe Ile
            220                 225                 230 aga aac cgc aca ctg cag ttg tgg ttg gat aat cca aag att cag ctg    891
Arg Asn Arg Thr Leu Gln Leu Trp Leu Asp Asn Pro Lys Ile Gln Leu
            235                 240                 245 aca ttt gag gct act ctc caa caa tta gaa gca cct tat aac agt gat    939
Thr Phe Glu Ala Thr Leu Gln Gln Leu Glu Ala Pro Tyr Asn Ser Asp
250                 255                 260                 265 act gtg ctt gtc cac cga gtt cac agt tat tta gag cgt cat ggt ctt    987
Thr Val Leu Val His Arg Val His Ser Tyr Leu Glu Arg His Gly Leu
                270                 275                 280 atc aac ttc ggc atc tat aag agg ata aaa ccc cta cca act aaa aag   1035
Ile Asn Phe Gly Ile Tyr Lys Arg Ile Lys Pro Leu Pro Thr Lys Lys
            285                 290                 295 aca gga aag gta att att ata ggc tct ggg gtc tca ggc ttg gca gca   1083
Thr Gly Lys Val Ile Ile Ile Gly Ser Gly Val Ser Gly Leu Ala Ala
            300                 305                 310 gct cga cag tta caa agt ttt gga atg gat gtc aca ctt ttg gaa gcc   1131
Ala Arg Gln Leu Gln Ser Phe Gly Met Asp Val Thr Leu Leu Glu Ala
315                 320                 325 agg gat cgt gtg ggt gga cga gtt gcc aca ttt cgc aaa gga aac tat   1179
Arg Asp Arg Val Gly Gly Arg Val Ala Thr Phe Arg Lys Gly Asn Tyr
330                 335                 340                 345 gta gct gat ctt gga gcc atg gtg gta aca ggt ctt gga ggg aat cct   1227
Val Ala Asp Leu Gly Ala Met Val Val Thr Gly Leu Gly Gly Asn Pro
                350                 355                 360 atg gct gtg gtc agc aaa caa gta aat atg gaa ctg gcc aag atc aag   1275
Met Ala Val Val Ser Lys Gln Val Asn Met Glu Leu Ala Lys Ile Lys
            365                 370                 375 caa aaa tgc cca ctt tat gaa gcc aac gga caa gct gac act gtc aag   1323
Gln Lys Cys Pro Leu Tyr Glu Ala Asn Gly Gln Ala Asp Thr Val Lys
            380                 385                 390 gtt cct aaa gag aaa gat gaa atg gta gag caa gag ttt aac cgg ttg   1371
Val Pro Lys Glu Lys Asp Glu Met Val Glu Gln Glu Phe Asn Arg Leu
            395                 400                 405 cta gaa gct aca tct tac ctt agt cat caa cta gac ttc aat gtc ctc   1419
Leu Glu Ala Thr Ser Tyr Leu Ser His Gln Leu Asp Phe Asn Val Leu
410                 415                 420                 425 aat aat aag cct gtg tcc ctt ggc cag gca ttg gaa gtt gtc att cag   1467
Asn Asn Lys Pro Val Ser Leu Gly Gln Ala Leu Glu Val Val Ile Gln
                430                 435                 440 tta caa gag aag cat gtc aaa gat gag cag att gaa cat tgg aag aag   1515
Leu Gln Glu Lys His Val Lys Asp Glu Gln Ile Glu His Trp Lys Lys
            445                 450                 455 ata gtg aaa act cag gaa gaa ttg aaa gaa ctt ctt aat aag atg gta   1563
Ile Val Lys Thr Gln Glu Glu Leu Lys Glu Leu Leu Asn Lys Met Val
            460                 465                 470 aat ttg aaa gag aaa att aaa gaa ctc cat cag caa tac aaa gaa gca   1611
Asn Leu Lys Glu Lys Ile Lys Glu Leu His Gln Gln Tyr Lys Glu Ala
475                 480                 485 tct gaa gta aag cca ccc aga gat att act gcc gag ttc tta gtg aaa   1659
Ser Glu Val Lys Pro Pro Arg Asp Ile Thr Ala Glu Phe Leu Val Lys
490                 495                 500                 505 agc aaa cac agg gat ctg acc gcc cta tgc aag gaa tat gat gaa tta   1707
```

```
Ser Lys His Arg Asp Leu Thr Ala Leu Cys Lys Glu Tyr Asp Glu Leu
            510                 515                 520 gct gaa aca caa gga aag cta gaa gaa aaa ctt cag gag ttg gaa gcg      1755
Ala Glu Thr Gln Gly Lys Leu Glu Glu Lys Leu Gln Glu Leu Glu Ala
                525                 530                 535 aat ccc cca agt gat gta tat ctc tca tca aga gac aga caa ata ctt      1803
Asn Pro Pro Ser Asp Val Tyr Leu Ser Ser Arg Asp Arg Gln Ile Leu
            540                 545                 550 gat tgg cat ttt gca aat ctt gaa ttt gct aat gcc aca cct ctc tca      1851
Asp Trp His Phe Ala Asn Leu Glu Phe Ala Asn Ala Thr Pro Leu Ser
        555                 560                 565 act ctc tcc ctt aag cac tgg gat cag gat gat gac ttt gag ttc act      1899
Thr Leu Ser Leu Lys His Trp Asp Gln Asp Asp Asp Phe Glu Phe Thr
570                 575                 580                 585 ggc agc cac ctg aca gta agg aat ggc tac tcg tgt gtg cct gtg gct      1947
Gly Ser His Leu Thr Val Arg Asn Gly Tyr Ser Cys Val Pro Val Ala
                590                 595                 600 tta gca gaa ggc cta gac att aaa ctg aat aca gca gtg cga cag gtt      1995
Leu Ala Glu Gly Leu Asp Ile Lys Leu Asn Thr Ala Val Arg Gln Val
            605                 610                 615 cgc tac acg gct tca gga tgt gaa gtg ata gct gtg aat acc cgc tcc      2043
Arg Tyr Thr Ala Ser Gly Cys Glu Val Ile Ala Val Asn Thr Arg Ser
        620                 625                 630 acg agt caa acc ttt att tat aaa tgc gac gca gtt ctc tgt acc ctt      2091
Thr Ser Gln Thr Phe Ile Tyr Lys Cys Asp Ala Val Leu Cys Thr Leu
635                 640                 645 ccc ctg ggt gtg ctg aag cag cag cca cca gcc gtt cag ttt gtg cca      2139
Pro Leu Gly Val Leu Lys Gln Gln Pro Pro Ala Val Gln Phe Val Pro
650                 655                 660                 665 cct ctc cct gag tgg aaa aca tct gca gtc caa agg atg gga ttt ggc      2187
Pro Leu Pro Glu Trp Lys Thr Ser Ala Val Gln Arg Met Gly Phe Gly
                670                 675                 680 aac ctt aac aag gtg gtg ttg tgt ttt gat cgg gtg ttc tgg gat cca      2235
Asn Leu Asn Lys Val Val Leu Cys Phe Asp Arg Val Phe Trp Asp Pro
            685                 690                 695 agt gtc aat ttg ttc ggg cat gtt ggc agt acg act gcc agc agg ggt      2283
Ser Val Asn Leu Phe Gly His Val Gly Ser Thr Thr Ala Ser Arg Gly
        700                 705                 710 gag ctc ttc ctc ttc tgg aac ctc tat aaa gct cca ata ctg ttg gca      2331
Glu Leu Phe Leu Phe Trp Asn Leu Tyr Lys Ala Pro Ile Leu Leu Ala
715                 720                 725 cta gtg gca gga gaa gct gct ggt atc atg gaa aac ata agt gac gat      2379
Leu Val Ala Gly Glu Ala Ala Gly Ile Met Glu Asn Ile Ser Asp Asp
730                 735                 740                 745 gtg att gtt ggc cga tgc ctg gcc att ctc aaa ggg att ttt ggt agc      2427
Val Ile Val Gly Arg Cys Leu Ala Ile Leu Lys Gly Ile Phe Gly Ser
                750                 755                 760 agt gca gta cct cag ccc aaa gaa act gtg gtg tct cgt tgg cgt gct      2475
Ser Ala Val Pro Gln Pro Lys Glu Thr Val Val Ser Arg Trp Arg Ala
            765                 770                 775 gat ccc tgg gct cgg ggc tct tat tcc tat gtt gct gca gga tca tct      2523
Asp Pro Trp Ala Arg Gly Ser Tyr Ser Tyr Val Ala Ala Gly Ser Ser
        780                 785                 790 gga aat gac tat gat tta atg gct cag cca atc act cct ggc ccc tcg      2571
Gly Asn Asp Tyr Asp Leu Met Ala Gln Pro Ile Thr Pro Gly Pro Ser
795                 800                 805 att cca ggt gcc cca cag ccg att cca cga ctc ttc ttt gcg gga gaa      2619
Ile Pro Gly Ala Pro Gln Pro Ile Pro Arg Leu Phe Phe Ala Gly Glu
810                 815                 820                 825
```

```
cat acg atc cgt aac tac cca gcc aca gtg cat ggt gct ctg ctg agt    2667
His Thr Ile Arg Asn Tyr Pro Ala Thr Val His Gly Ala Leu Leu Ser
                830                 835                 840 ggg ctg cga gaa gcg gga aga att gca gac cag ttt ttg ggg gcc atg    2715
Gly Leu Arg Glu Ala Gly Arg Ile Ala Asp Gln Phe Leu Gly Ala Met
            845                 850                 855 tat acg ctg cct cgc cag gcc aca cca ggt gtt cct gca cag cag tcc    2763
Tyr Thr Leu Pro Arg Gln Ala Thr Pro Gly Val Pro Ala Gln Gln Ser
        860                 865                 870 cca agc atg tgagacagat gcattctaag ggaagaggcc catgtgcctg            2812
Pro Ser Met
    875 tttctgccat gtaaggaagg ctcttctagc aatactagat cccactgaga aaatccaccc    2872 tggcatctgg gctcctgatc agctgatgga gctcctgatt tgacaaagga gcttgcctcc   2932 tttgaatgac ctagagcaca gggaggaact tgtccattag tttggaattg tgttcttcgt   2992 aaagactgag gcaagcaagt gctgtgaaat aacatcatct tagtcccttg gtgtgtgggg   3052 tttttgtttt tttttatat tttgagaata aaacttcata taaaattggc               3102

<210> SEQ ID NO 29
<211> LENGTH: 876
<212> TYPE: PRT
<213> ORGANISM: Homo sapiens

<400> SEQUENCE: 29

Met Leu Ser Gly Lys Lys Ala Ala Ala Ala Ala Ala Ala Ala Ala Ala
 1               5                  10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140

Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Gln Ala Gly
                165                 170                 175

Gly Leu Gln Asp Asp Ser Ser Gly Gly Tyr Gly Asp Gly Gln Ala Ser
            180                 185                 190

Gly Val Glu Gly Ala Ala Phe Gln Ser Arg Leu Pro His Asp Arg Met
        195                 200                 205

Thr Ser Gln Glu Ala Ala Cys Phe Pro Asp Ile Ile Ser Gly Pro Gln
    210                 215                 220

Gln Thr Gln Lys Val Phe Leu Phe Ile Arg Asn Arg Thr Leu Gln Leu
225                 230                 235                 240
```

-continued

```
Trp Leu Asp Asn Pro Lys Ile Gln Leu Thr Phe Glu Ala Thr Leu Gln
            245                 250                 255

Gln Leu Glu Ala Pro Tyr Asn Ser Asp Thr Val Leu Val His Arg Val
        260                 265                 270

His Ser Tyr Leu Glu Arg His Gly Leu Ile Asn Phe Gly Ile Tyr Lys
    275                 280                 285

Arg Ile Lys Pro Leu Pro Thr Lys Lys Thr Gly Lys Val Ile Ile Ile
290                 295                 300

Gly Ser Gly Val Ser Gly Leu Ala Ala Ala Arg Gln Leu Gln Ser Phe
305                 310                 315                 320

Gly Met Asp Val Thr Leu Leu Glu Ala Arg Asp Arg Val Gly Gly Arg
                325                 330                 335

Val Ala Thr Phe Arg Lys Gly Asn Tyr Val Ala Asp Leu Gly Ala Met
            340                 345                 350

Val Val Thr Gly Leu Gly Gly Asn Pro Met Ala Val Val Ser Lys Gln
        355                 360                 365

Val Asn Met Glu Leu Ala Lys Ile Lys Gln Lys Cys Pro Leu Tyr Glu
    370                 375                 380

Ala Asn Gly Gln Ala Asp Thr Val Lys Val Pro Lys Glu Lys Asp Glu
385                 390                 395                 400

Met Val Glu Gln Glu Phe Asn Arg Leu Leu Glu Ala Thr Ser Tyr Leu
                405                 410                 415

Ser His Gln Leu Asp Phe Asn Val Leu Asn Asn Lys Pro Val Ser Leu
            420                 425                 430

Gly Gln Ala Leu Glu Val Val Ile Gln Leu Gln Glu Lys His Val Lys
        435                 440                 445

Asp Glu Gln Ile Glu His Trp Lys Lys Ile Val Lys Thr Gln Glu Glu
    450                 455                 460

Leu Lys Glu Leu Leu Asn Lys Met Val Asn Leu Lys Glu Lys Ile Lys
465                 470                 475                 480

Glu Leu His Gln Gln Tyr Lys Glu Ala Ser Glu Val Lys Pro Pro Arg
                485                 490                 495

Asp Ile Thr Ala Glu Phe Leu Val Lys Ser Lys His Arg Asp Leu Thr
            500                 505                 510

Ala Leu Cys Lys Glu Tyr Asp Glu Leu Ala Glu Thr Gln Gly Lys Leu
        515                 520                 525

Glu Glu Lys Leu Gln Glu Leu Glu Ala Asn Pro Pro Ser Asp Val Tyr
    530                 535                 540

Leu Ser Ser Arg Asp Arg Gln Ile Leu Asp Trp His Phe Ala Asn Leu
545                 550                 555                 560

Glu Phe Ala Asn Ala Thr Pro Leu Ser Thr Leu Ser Leu Lys His Trp
                565                 570                 575

Asp Gln Asp Asp Asp Phe Glu Phe Thr Gly Ser His Leu Thr Val Arg
            580                 585                 590

Asn Gly Tyr Ser Cys Val Pro Val Ala Leu Ala Glu Gly Leu Asp Ile
        595                 600                 605

Lys Leu Asn Thr Ala Val Arg Gln Val Arg Tyr Thr Ala Ser Gly Cys
    610                 615                 620

Glu Val Ile Ala Val Asn Thr Arg Ser Thr Ser Gln Thr Phe Ile Tyr
625                 630                 635                 640

Lys Cys Asp Ala Val Leu Cys Thr Leu Pro Leu Gly Val Leu Lys Gln
                645                 650                 655

Gln Pro Pro Ala Val Gln Phe Val Pro Pro Leu Pro Glu Trp Lys Thr
```

-continued

```
                    660                 665                 670
Ser Ala Val Gln Arg Met Gly Phe Gly Asn Leu Asn Lys Val Val Leu
            675                 680                 685

Cys Phe Asp Arg Val Phe Trp Asp Pro Ser Val Asn Leu Phe Gly His
        690                 695                 700

Val Gly Ser Thr Thr Ala Ser Arg Gly Glu Leu Phe Leu Phe Trp Asn
705                 710                 715                 720

Leu Tyr Lys Ala Pro Ile Leu Leu Ala Leu Val Ala Gly Glu Ala Ala
                725                 730                 735

Gly Ile Met Glu Asn Ile Ser Asp Asp Val Ile Val Gly Arg Cys Leu
            740                 745                 750

Ala Ile Leu Lys Gly Ile Phe Gly Ser Ser Ala Val Pro Gln Pro Lys
        755                 760                 765

Glu Thr Val Val Ser Arg Trp Arg Ala Asp Pro Trp Ala Arg Gly Ser
    770                 775                 780

Tyr Ser Tyr Val Ala Ala Gly Ser Ser Gly Asn Asp Tyr Asp Leu Met
785                 790                 795                 800

Ala Gln Pro Ile Thr Pro Gly Pro Ser Ile Pro Gly Ala Pro Gln Pro
                805                 810                 815

Ile Pro Arg Leu Phe Phe Ala Gly Glu His Thr Ile Arg Asn Tyr Pro
            820                 825                 830

Ala Thr Val His Gly Ala Leu Leu Ser Gly Leu Arg Glu Ala Gly Arg
        835                 840                 845

Ile Ala Asp Gln Phe Leu Gly Ala Met Tyr Thr Leu Pro Arg Gln Ala
    850                 855                 860

Thr Pro Gly Val Pro Ala Gln Gln Ser Pro Ser Met
865                 870                 875

<210> SEQ ID NO 30
<211> LENGTH: 3030
<212> TYPE: DNA
<213> ORGANISM: Homo sapiens
<220> FEATURE:
<221> NAME/KEY: CDS
<222> LOCATION: (145)..(2700)

<400> SEQUENCE: 30
ggcgggagcg cgcttggcgc gtgcgtacgc gacggcggtt ggcggcgcgc gggcagcgtg     60
aagcgaggcg aggcaaggct tttcggaccc acggagcgac agagcgagcg gcccctacgg    120
ccgtcggcgg cccggcggcc cgag atg tta tct ggg aag aag gcg gca gcc       171
                           Met Leu Ser Gly Lys Lys Ala Ala Ala
                             1               5 gcg gcg gcg gcg gct gca gcg gca gca acc ggg acg gag gct ggc cct      219
Ala Ala Ala Ala Ala Ala Ala Ala Thr Gly Thr Glu Ala Gly Pro
 10                  15                  20                  25 ggg aca gca ggc ggc tcc gag aac ggg tct gag gtg gcc gcg cag ccc      267
Gly Thr Ala Gly Gly Ser Glu Asn Gly Ser Glu Val Ala Ala Gln Pro
                30                  35                  40 gcg ggc ctg tcg ggc cca gcc gag gtc ggg ccg ggg gcg gtg ggg gag      315
Ala Gly Leu Ser Gly Pro Ala Glu Val Gly Pro Gly Ala Val Gly Glu
            45                  50                  55 cgc aca ccc cgc aag aaa gag cct ccg cgg gcc tcg ccc ccg ggg ggc      363
Arg Thr Pro Arg Lys Lys Glu Pro Pro Arg Ala Ser Pro Pro Gly Gly
        60                  65                  70 ctg gcg gaa ccg ccg ggg tcc gca ggg cct cag gcc ggc cct act gtc      411
Leu Ala Glu Pro Pro Gly Ser Ala Gly Pro Gln Ala Gly Pro Thr Val
    75                  80                  85
```

-continued

| | | |
|---|---|---|
| gtg cct ggg tct gcg acc ccc atg gaa act gga ata gca gag act ccg<br>Val Pro Gly Ser Ala Thr Pro Met Glu Thr Gly Ile Ala Glu Thr Pro<br>90               95                  100                 105 | 459 |
| gag ggg cgt cgg acc agc cgg cgc aag cgg gcg aag gta gag tac aga<br>Glu Gly Arg Arg Thr Ser Arg Arg Lys Arg Ala Lys Val Glu Tyr Arg<br>         110                 115                 120 | 507 |
| gag atg gat gaa agc ttg gcc aac ctc tca gaa gat gag tat tat tca<br>Glu Met Asp Glu Ser Leu Ala Asn Leu Ser Glu Asp Glu Tyr Tyr Ser<br>     125                 130                 135 | 555 |
| gaa gaa gag aga aat gcc aaa gca gag aag gaa aag aag ctt ccc cca<br>Glu Glu Glu Arg Asn Ala Lys Ala Glu Lys Glu Lys Lys Leu Pro Pro<br> 140                 145                 150 | 603 |
| cca ccc cct caa gcc cca cct gag gaa gaa aat gaa agt gag cct gaa<br>Pro Pro Pro Gln Ala Pro Pro Glu Glu Glu Asn Glu Ser Glu Pro Glu<br>155                 160                 165 | 651 |
| gaa cca tcg ggt gtg gag ggc gca gct ttc cag agc cga ctt cct cat<br>Glu Pro Ser Gly Val Glu Gly Ala Ala Phe Gln Ser Arg Leu Pro His<br>170                 175                 180                 185 | 699 |
| gac cgg atg act tct caa gaa gca gcc tgt ttt cca gat att atc agt<br>Asp Arg Met Thr Ser Gln Glu Ala Ala Cys Phe Pro Asp Ile Ile Ser<br>             190                 195                 200 | 747 |
| gga cca caa cag acc cag aag gtt ttt ctt ttc att aga aac cgc aca<br>Gly Pro Gln Gln Thr Gln Lys Val Phe Leu Phe Ile Arg Asn Arg Thr<br>         205                 210                 215 | 795 |
| ctg cag ttg tgg ttg gat aat cca aag att cag ctg aca ttt gag gct<br>Leu Gln Leu Trp Leu Asp Asn Pro Lys Ile Gln Leu Thr Phe Glu Ala<br>     220                 225                 230 | 843 |
| act ctc caa caa tta gaa gca cct tat aac agt gat act gtg ctt gtc<br>Thr Leu Gln Gln Leu Glu Ala Pro Tyr Asn Ser Asp Thr Val Leu Val<br> 235                 240                 245 | 891 |
| cac cga gtt cac agt tat tta gag cgt cat ggt ctt atc aac ttc ggc<br>His Arg Val His Ser Tyr Leu Glu Arg His Gly Leu Ile Asn Phe Gly<br>250                 255                 260                 265 | 939 |
| atc tat aag agg ata aaa ccc cta cca act aaa aag aca gga aag gta<br>Ile Tyr Lys Arg Ile Lys Pro Leu Pro Thr Lys Lys Thr Gly Lys Val<br>             270                 275                 280 | 987 |
| att att ata ggc tct ggg gtc tca ggc ttg gca gca gct cga cag tta<br>Ile Ile Ile Gly Ser Gly Val Ser Gly Leu Ala Ala Ala Arg Gln Leu<br>         285                 290                 295 | 1035 |
| caa agt ttt gga atg gat gtc aca ctt ttg gaa gcc agg gat cgt gtg<br>Gln Ser Phe Gly Met Asp Val Thr Leu Leu Glu Ala Arg Asp Arg Val<br>     300                 305                 310 | 1083 |
| ggt gga cga gtt gcc aca ttt cgc aaa gga aac tat gta gct gat ctt<br>Gly Gly Arg Val Ala Thr Phe Arg Lys Gly Asn Tyr Val Ala Asp Leu<br> 315                 320                 325 | 1131 |
| gga gcc atg gtg gta aca ggt ctt gga ggg aat cct atg gct gtg gtc<br>Gly Ala Met Val Val Thr Gly Leu Gly Gly Asn Pro Met Ala Val Val<br>330                 335                 340                 345 | 1179 |
| agc aaa caa gta aat atg gaa ctg gcc aag atc aag caa aaa tgc cca<br>Ser Lys Gln Val Asn Met Glu Leu Ala Lys Ile Lys Gln Lys Cys Pro<br>             350                 355                 360 | 1227 |
| ctt tat gaa gcc aac gga caa gct gtt cct aaa gag aaa gat gaa atg<br>Leu Tyr Glu Ala Asn Gly Gln Ala Val Pro Lys Glu Lys Asp Glu Met<br>         365                 370                 375 | 1275 |
| gta gag caa gag ttt aac cgg ttg cta gaa gct aca tct tac ctt agt<br>Val Glu Gln Glu Phe Asn Arg Leu Leu Glu Ala Thr Ser Tyr Leu Ser<br>     380                 385                 390 | 1323 |
| cat caa cta gac ttc aat gtc ctc aat aat aag cct gtg tcc ctt ggc<br>His Gln Leu Asp Phe Asn Val Leu Asn Asn Lys Pro Val Ser Leu Gly | 1371 |

-continued

|     |     |     |     |     |     |     |     |     |     |     |     |     |     |     |     |      |
|---|---|---|---|---|---|---|---|---|---|---|---|---|---|---|---|---|
|     |     |     | 395 |     |     |     | 400 |     |     |     | 405 |     |     |     |     |      |
| cag | gca | ttg | gaa | gtt | gtc | att | cag | tta | caa | gag | aag | cat | gtc | aaa | gat | 1419 |
| Gln | Ala | Leu | Glu | Val | Val | Ile | Gln | Leu | Gln | Glu | Lys | His | Val | Lys | Asp |      |
| 410 |     |     |     |     | 415 |     |     |     |     | 420 |     |     |     |     | 425 |      |
| gag | cag | att | gaa | cat | tgg | aag | aag | ata | gtg | aaa | act | cag | gaa | gaa | ttg | 1467 |
| Glu | Gln | Ile | Glu | His | Trp | Lys | Lys | Ile | Val | Lys | Thr | Gln | Glu | Glu | Leu |      |
|     |     |     |     |     | 430 |     |     |     |     | 435 |     |     |     |     | 440 |      |
| aaa | gaa | ctt | ctt | aat | aag | atg | gta | aat | ttg | aaa | gag | aaa | att | aaa | gaa | 1515 |
| Lys | Glu | Leu | Leu | Asn | Lys | Met | Val | Asn | Leu | Lys | Glu | Lys | Ile | Lys | Glu |      |
|     |     |     |     | 445 |     |     |     |     | 450 |     |     |     |     | 455 |     |      |
| ctc | cat | cag | caa | tac | aaa | gaa | gca | tct | gaa | gta | aag | cca | ccc | aga | gat | 1563 |
| Leu | His | Gln | Gln | Tyr | Lys | Glu | Ala | Ser | Glu | Val | Lys | Pro | Pro | Arg | Asp |      |
|     |     |     | 460 |     |     |     |     | 465 |     |     |     |     | 470 |     |     |      |
| att | act | gcc | gag | ttc | tta | gtg | aaa | agc | aaa | cac | agg | gat | ctg | acc | gcc | 1611 |
| Ile | Thr | Ala | Glu | Phe | Leu | Val | Lys | Ser | Lys | His | Arg | Asp | Leu | Thr | Ala |      |
|     |     | 475 |     |     |     |     | 480 |     |     |     |     | 485 |     |     |     |      |
| cta | tgc | aag | gaa | tat | gat | gaa | tta | gct | gaa | aca | caa | gga | aag | cta | gaa | 1659 |
| Leu | Cys | Lys | Glu | Tyr | Asp | Glu | Leu | Ala | Glu | Thr | Gln | Gly | Lys | Leu | Glu |      |
| 490 |     |     |     |     | 495 |     |     |     |     | 500 |     |     |     |     | 505 |      |
| gaa | aaa | ctt | cag | gag | ttg | gaa | gcg | aat | ccc | cca | agt | gat | gta | tat | ctc | 1707 |
| Glu | Lys | Leu | Gln | Glu | Leu | Glu | Ala | Asn | Pro | Pro | Ser | Asp | Val | Tyr | Leu |      |
|     |     |     |     | 510 |     |     |     |     | 515 |     |     |     |     | 520 |     |      |
| tca | tca | aga | gac | aga | caa | ata | ctt | gat | tgg | cat | ttt | gca | aat | ctt | gaa | 1755 |
| Ser | Ser | Arg | Asp | Arg | Gln | Ile | Leu | Asp | Trp | His | Phe | Ala | Asn | Leu | Glu |      |
|     |     | 525 |     |     |     |     | 530 |     |     |     |     | 535 |     |     |     |      |
| ttt | gct | aat | gcc | aca | cct | ctc | tca | act | ctc | tcc | ctt | aag | cac | tgg | gat | 1803 |
| Phe | Ala | Asn | Ala | Thr | Pro | Leu | Ser | Thr | Leu | Ser | Leu | Lys | His | Trp | Asp |      |
| 540 |     |     |     |     | 545 |     |     |     |     | 550 |     |     |     |     |     |      |
| cag | gat | gat | gac | ttt | gag | ttc | act | ggc | agc | cac | ctg | aca | gta | agg | aat | 1851 |
| Gln | Asp | Asp | Asp | Phe | Glu | Phe | Thr | Gly | Ser | His | Leu | Thr | Val | Arg | Asn |      |
|     | 555 |     |     |     |     | 560 |     |     |     |     | 565 |     |     |     |     |      |
| ggc | tac | tcg | tgt | gtg | cct | gtg | gct | tta | gca | gaa | ggc | cta | gac | att | aaa | 1899 |
| Gly | Tyr | Ser | Cys | Val | Pro | Val | Ala | Leu | Ala | Glu | Gly | Leu | Asp | Ile | Lys |      |
| 570 |     |     |     |     | 575 |     |     |     |     | 580 |     |     |     |     | 585 |      |
| ctg | aat | aca | gca | gtg | cga | cag | gtt | cgc | tac | acg | gct | tca | gga | tgt | gaa | 1947 |
| Leu | Asn | Thr | Ala | Val | Arg | Gln | Val | Arg | Tyr | Thr | Ala | Ser | Gly | Cys | Glu |      |
|     |     |     |     | 590 |     |     |     |     | 595 |     |     |     |     | 600 |     |      |
| gtg | ata | gct | gtg | aat | acc | cgc | tcc | acg | agt | caa | acc | ttt | att | tat | aaa | 1995 |
| Val | Ile | Ala | Val | Asn | Thr | Arg | Ser | Thr | Ser | Gln | Thr | Phe | Ile | Tyr | Lys |      |
|     |     | 605 |     |     |     |     | 610 |     |     |     |     | 615 |     |     |     |      |
| tgc | gac | gca | gtt | ctc | tgt | acc | ctt | ccc | ctg | ggt | gtg | ctg | aag | cag | cag | 2043 |
| Cys | Asp | Ala | Val | Leu | Cys | Thr | Leu | Pro | Leu | Gly | Val | Leu | Lys | Gln | Gln |      |
| 620 |     |     |     |     | 625 |     |     |     |     | 630 |     |     |     |     |     |      |
| cca | cca | gcc | gtt | cag | ttt | gtg | cca | cct | ctc | cct | gag | tgg | aaa | aca | tct | 2091 |
| Pro | Pro | Ala | Val | Gln | Phe | Val | Pro | Pro | Leu | Pro | Glu | Trp | Lys | Thr | Ser |      |
|     | 635 |     |     |     |     | 640 |     |     |     |     | 645 |     |     |     |     |      |
| gca | gtc | caa | agg | atg | gga | ttt | gcc | aac | ctt | aac | aag | gtg | gtg | ttg | tgt | 2139 |
| Ala | Val | Gln | Arg | Met | Gly | Phe | Ala | Asn | Leu | Asn | Lys | Val | Val | Leu | Cys |      |
| 650 |     |     |     |     | 655 |     |     |     |     | 660 |     |     |     |     | 665 |      |
| ttt | gat | cgg | gtg | ttc | tgg | gat | cca | agt | gtc | aat | ttg | ttc | ggg | cat | gtt | 2187 |
| Phe | Asp | Arg | Val | Phe | Trp | Asp | Pro | Ser | Val | Asn | Leu | Phe | Gly | His | Val |      |
|     |     |     | 670 |     |     |     |     | 675 |     |     |     |     | 680 |     |     |      |
| ggc | agt | acg | act | gcc | agc | agg | ggt | gag | ctc | ttc | ctc | ttc | tgg | aac | ctc | 2235 |
| Gly | Ser | Thr | Thr | Ala | Ser | Arg | Gly | Glu | Leu | Phe | Leu | Phe | Trp | Asn | Leu |      |
|     |     | 685 |     |     |     |     | 690 |     |     |     |     | 695 |     |     |     |      |
| tat | aaa | gct | cca | ata | ctg | ttg | gca | cta | gtg | gca | gga | gaa | gct | gct | ggt | 2283 |
| Tyr | Lys | Ala | Pro | Ile | Leu | Leu | Ala | Leu | Val | Ala | Gly | Glu | Ala | Ala | Gly |      |
|     |     |     | 700 |     |     |     |     | 705 |     |     |     |     | 710 |     |     |      |
| atc | atg | gaa | aac | ata | agt | gac | gat | gtg | att | gtt | ggc | cga | tgc | ctg | gcc | 2331 |

-continued

```
Ile Met Glu Asn Ile Ser Asp Asp Val Ile Val Gly Arg Cys Leu Ala
    715                 720                 725 att ctc aaa ggg att ttt ggt agc agt gca gta cct cag ccc aaa gaa    2379
Ile Leu Lys Gly Ile Phe Gly Ser Ser Ala Val Pro Gln Pro Lys Glu
730                 735                 740                 745 act gtg gtg tct cgt tgg cgt gct gat ccc tgg gct cgg ggc tct tat    2427
Thr Val Val Ser Arg Trp Arg Ala Asp Pro Trp Ala Arg Gly Ser Tyr
                750                 755                 760 tcc tat gtt gct gca gga tca tct gga aat gac tat gat tta atg gct    2475
Ser Tyr Val Ala Ala Gly Ser Ser Gly Asn Asp Tyr Asp Leu Met Ala
            765                 770                 775 cag cca atc act cct ggc ccc tcg att cca ggt gcc cca cag ccg att    2523
Gln Pro Ile Thr Pro Gly Pro Ser Ile Pro Gly Ala Pro Gln Pro Ile
        780                 785                 790 cca cga ctc ttc ttt gcg gga gaa cat acg atc cgt aac tac cca gcc    2571
Pro Arg Leu Phe Phe Ala Gly Glu His Thr Ile Arg Asn Tyr Pro Ala
    795                 800                 805 aca gtg cat ggt gct ctg ctg agt ggg ctg cga gaa gcg gga aga att    2619
Thr Val His Gly Ala Leu Leu Ser Gly Leu Arg Glu Ala Gly Arg Ile
810                 815                 820                 825 gca gac cag ttt ttg ggg gcc atg tat acg ctg cct cgc cag gcc aca    2667
Ala Asp Gln Phe Leu Gly Ala Met Tyr Thr Leu Pro Arg Gln Ala Thr
                830                 835                 840 cca ggt gtt cct gca cag cag tcc cca agc atg tgagacagat gcattctaag   2720
Pro Gly Val Pro Ala Gln Gln Ser Pro Ser Met
            845                 850 ggaagaggcc catgtgcctg tttctgccat gtaaggaagg ctcttctagc aatactagat   2780
cccactgaga aaatccaccc tggcatctgg gctcctgatc agctgatgga gctcctgatt   2840
tgacaaagga gcttgcctcc tttgaatgac ctagagcaca gggaggaact tgtccattag   2900
tttggaattg tgttcttcgt aaagactgag gcaagcaagt gctgtgaaat aacatcatct   2960
tagtcccttg gtgtgtgggg ttttttgtttt tttttttatat tttgagaata aaacttcata  3020
taaaattggc                                                          3030
```

```
<210> SEQ ID NO 31
<211> LENGTH: 852
<212> TYPE: PRT
<213> ORGANISM: Homo sapiens

<400> SEQUENCE: 31

Met Leu Ser Gly Lys Lys Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125
```

-continued

```
Asn Leu Ser Glu Asp Glu Tyr Tyr Ser Glu Glu Arg Asn Ala Lys
        130                 135                 140

Ala Glu Lys Glu Lys Lys Leu Pro Pro Pro Gln Ala Pro Pro
145                 150                 155                 160

Glu Glu Glu Asn Glu Ser Glu Pro Glu Pro Ser Gly Val Glu Gly
                165                 170                 175

Ala Ala Phe Gln Ser Arg Leu Pro His Asp Arg Met Thr Ser Gln Glu
        180                 185                 190

Ala Ala Cys Phe Pro Asp Ile Ile Ser Gly Pro Gln Gln Thr Gln Lys
        195                 200                 205

Val Phe Leu Phe Ile Arg Asn Arg Thr Leu Gln Leu Trp Leu Asp Asn
210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
                245                 250                 255

Glu Arg His Gly Leu Ile Asn Phe Gly Ile Tyr Lys Arg Ile Lys Pro
        260                 265                 270

Leu Pro Thr Lys Lys Thr Gly Lys Val Ile Ile Gly Ser Gly Val
        275                 280                 285

Ser Gly Leu Ala Ala Ala Arg Gln Leu Gln Ser Phe Gly Met Asp Val
290                 295                 300

Thr Leu Leu Glu Ala Arg Asp Arg Val Gly Gly Arg Val Ala Thr Phe
305                 310                 315                 320

Arg Lys Gly Asn Tyr Val Ala Asp Leu Gly Ala Met Val Val Thr Gly
                325                 330                 335

Leu Gly Gly Asn Pro Met Ala Val Val Ser Lys Gln Val Asn Met Glu
        340                 345                 350

Leu Ala Lys Ile Lys Gln Lys Cys Pro Leu Tyr Glu Ala Asn Gly Gln
        355                 360                 365

Ala Val Pro Lys Glu Lys Asp Glu Met Val Glu Gln Glu Phe Asn Arg
        370                 375                 380

Leu Leu Glu Ala Thr Ser Tyr Leu Ser His Gln Leu Asp Phe Asn Val
385                 390                 395                 400

Leu Asn Asn Lys Pro Val Ser Leu Gly Gln Ala Leu Glu Val Val Ile
                405                 410                 415

Gln Leu Gln Glu Lys His Val Lys Asp Glu Gln Ile Glu His Trp Lys
        420                 425                 430

Lys Ile Val Lys Thr Gln Glu Glu Leu Lys Glu Leu Leu Asn Lys Met
        435                 440                 445

Val Asn Leu Lys Glu Lys Ile Lys Glu Leu His Gln Gln Tyr Lys Glu
450                 455                 460

Ala Ser Glu Val Lys Pro Pro Arg Asp Ile Thr Ala Glu Phe Leu Val
465                 470                 475                 480

Lys Ser Lys His Arg Asp Leu Thr Ala Leu Cys Lys Glu Tyr Asp Glu
                485                 490                 495

Leu Ala Glu Thr Gln Gly Lys Leu Glu Glu Lys Leu Gln Glu Leu Glu
        500                 505                 510

Ala Asn Pro Pro Ser Asp Val Tyr Leu Ser Ser Arg Asp Arg Gln Ile
        515                 520                 525

Leu Asp Trp His Phe Ala Asn Leu Glu Phe Ala Asn Ala Thr Pro Leu
530                 535                 540

Ser Thr Leu Ser Leu Lys His Trp Asp Gln Asp Asp Asp Phe Glu Phe
```

```
                        545                 550                 555                 560

Thr Gly Ser His Leu Thr Val Arg Asn Gly Tyr Ser Cys Val Pro Val
                         565                 570                 575

Ala Leu Ala Glu Gly Leu Asp Ile Lys Leu Asn Thr Ala Val Arg Gln
                         580                 585                 590

Val Arg Tyr Thr Ala Ser Gly Cys Glu Val Ile Ala Val Asn Thr Arg
                         595                 600                 605

Ser Thr Ser Gln Thr Phe Ile Tyr Lys Cys Asp Ala Val Leu Cys Thr
                         610                 615                 620

Leu Pro Leu Gly Val Leu Lys Gln Gln Pro Ala Val Gln Phe Val
         625                 630                 635                 640

Pro Pro Leu Pro Glu Trp Lys Thr Ser Ala Val Gln Arg Met Gly Phe
                         645                 650                 655

Gly Asn Leu Asn Lys Val Val Leu Cys Phe Asp Arg Val Phe Trp Asp
                         660                 665                 670

Pro Ser Val Asn Leu Phe Gly His Val Gly Ser Thr Thr Ala Ser Arg
                         675                 680                 685

Gly Glu Leu Phe Leu Phe Trp Asn Leu Tyr Lys Ala Pro Ile Leu Leu
                         690                 695                 700

Ala Leu Val Ala Gly Glu Ala Gly Ile Met Glu Asn Ile Ser Asp
         705                 710                 715                 720

Asp Val Ile Val Gly Arg Cys Leu Ala Ile Leu Lys Gly Ile Phe Gly
                         725                 730                 735

Ser Ser Ala Val Pro Gln Pro Lys Glu Thr Val Val Ser Arg Trp Arg
                         740                 745                 750

Ala Asp Pro Trp Ala Arg Gly Ser Tyr Ser Tyr Val Ala Ala Gly Ser
                         755                 760                 765

Ser Gly Asn Asp Tyr Asp Leu Met Ala Gln Pro Ile Thr Pro Gly Pro
                         770                 775                 780

Ser Ile Pro Gly Ala Pro Gln Pro Ile Pro Arg Leu Phe Phe Ala Gly
         785                 790                 795                 800

Glu His Thr Ile Arg Asn Tyr Pro Ala Thr Val His Gly Ala Leu Leu
                         805                 810                 815

Ser Gly Leu Arg Glu Ala Gly Arg Ile Ala Asp Gln Phe Leu Gly Ala
                         820                 825                 830

Met Tyr Thr Leu Pro Arg Gln Ala Thr Pro Gly Val Pro Ala Gln Gln
                         835                 840                 845

Ser Pro Ser Met
             850

<210> SEQ ID NO 32
<211> LENGTH: 1449
<212> TYPE: DNA
<213> ORGANISM: Homo sapiens
<220> FEATURE:
<221> NAME/KEY: CDS
<222> LOCATION: (1)..(1446)

<400> SEQUENCE: 32 atg gtg gag aag ggc ccc gag gtc tca ggg aag cgg aga ggg agg aac      48
Met Val Glu Lys Gly Pro Glu Val Ser Gly Lys Arg Arg Gly Arg Asn
 1               5                  10                  15 aac gcg gcc gcc tcc gcc tcc gcc gcc gcc tcc gcc gcc tcg             96
Asn Ala Ala Ala Ser Ala Ser Ala Ala Ala Ser Ala Ala Ser
                20                  25                  30 gcc gcc tgc gcc tcg cca gcc gcc act gcc gcc tcg ggc gcc gcc gcc    144
```

```
                Ala Ala Cys Ala Ser Pro Ala Ala Thr Ala Ala Ser Gly Ala Ala Ala
                         35                  40                  45 tcc tca gcc tcg gcc gcc gcc tca gcc gcc gcc gcc ccc aat aat              192
Ser Ser Ala Ser Ala Ala Ala Ser Ala Ala Ala Ala Pro Asn Asn
 50                  55                  60 ggc cag aat aaa agt ttg gcg gcg gcg gcg ccc aat ggc aac agc agc          240
Gly Gln Asn Lys Ser Leu Ala Ala Ala Ala Pro Asn Gly Asn Ser Ser
 65                  70                  75                  80 agc aac tcc tgg gag gaa ggc agc tcg ggc tcg tcc agc gac gag gag          288
Ser Asn Ser Trp Glu Glu Gly Ser Ser Gly Ser Ser Ser Asp Glu Glu
                     85                  90                  95 cac ggt ggc ggt ggc atg agg gtc gga ccc cag tac cag gcg gtg gtg          336
His Gly Gly Gly Gly Met Arg Val Gly Pro Gln Tyr Gln Ala Val Val
                 100                 105                 110 ccc gac ttc gac ccc gcc aaa ctg gca aga cgc agt caa gaa cgg gac          384
Pro Asp Phe Asp Pro Ala Lys Leu Ala Arg Arg Ser Gln Glu Arg Asp
             115                 120                 125 aat ctt ggc atg ttg gtc tgg tca ccc aat caa aat ctg tca gaa gca          432
Asn Leu Gly Met Leu Val Trp Ser Pro Asn Gln Asn Leu Ser Glu Ala
         130                 135                 140 aag ttg gat gaa tac att gcc att gcc aaa gaa aag cat ggg tac aac          480
Lys Leu Asp Glu Tyr Ile Ala Ile Ala Lys Glu Lys His Gly Tyr Asn
145                 150                 155                 160 atg gaa cag gct ctt ggg atg ctc ttc tgg cat aaa cat aat atc gaa          528
Met Glu Gln Ala Leu Gly Met Leu Phe Trp His Lys His Asn Ile Glu
                 165                 170                 175 aag tca ttg gct gat ttg ccc aac ttt acc cct ttc cca gat gag tgg          576
Lys Ser Leu Ala Asp Leu Pro Asn Phe Thr Pro Phe Pro Asp Glu Trp
             180                 185                 190 act gtg gaa gat aaa gtc tta ttt gag caa gcc ttt agt ttt cat ggg          624
Thr Val Glu Asp Lys Val Leu Phe Glu Gln Ala Phe Ser Phe His Gly
         195                 200                 205 aaa act ttt cat aga atc caa caa atg ctt cca gat aaa tct ata gca          672
Lys Thr Phe His Arg Ile Gln Gln Met Leu Pro Asp Lys Ser Ile Ala
     210                 215                 220 agt ctg gtg aaa ttt tac tat tct tgg aag aag acg agg act aaa act          720
Ser Leu Val Lys Phe Tyr Tyr Ser Trp Lys Lys Thr Arg Thr Lys Thr
225                 230                 235                 240 agt gtg atg gat cgc cat gcc cgg aaa caa aaa cgg gag cgg gag gag          768
Ser Val Met Asp Arg His Ala Arg Lys Gln Lys Arg Glu Arg Glu Glu
                 245                 250                 255 agc gag gat gaa ctg gaa gag gca aat gga aac aat ccc att gac att          816
Ser Glu Asp Glu Leu Glu Glu Ala Asn Gly Asn Asn Pro Ile Asp Ile
             260                 265                 270 gag gtt gat caa aac aag gaa agc aaa aag gag gtt ccc cct act gag          864
Glu Val Asp Gln Asn Lys Glu Ser Lys Lys Glu Val Pro Pro Thr Glu
         275                 280                 285 aca gtt cct cag gtc aaa aaa gaa aaa cat agc aca caa gct aaa aat          912
Thr Val Pro Gln Val Lys Lys Glu Lys His Ser Thr Gln Ala Lys Asn
     290                 295                 300 aga gca aaa agg aaa cct cca aaa gga atg ttt ctt tct caa gaa gat          960
Arg Ala Lys Arg Lys Pro Pro Lys Gly Met Phe Leu Ser Gln Glu Asp
305                 310                 315                 320 gtg gag gct gtt tct gcc aat gcc act gct gct acc acg gtg ctg aga         1008
Val Glu Ala Val Ser Ala Asn Ala Thr Ala Ala Thr Thr Val Leu Arg
                 325                 330                 335 caa cta gac atg gaa ttg gtt tca gtc aaa cga cag atc cag aat att         1056
Gln Leu Asp Met Glu Leu Val Ser Val Lys Arg Gln Ile Gln Asn Ile
             340                 345                 350
```

-continued

| | | | | | | | | | | | | | | | |
|---|---|---|---|---|---|---|---|---|---|---|---|---|---|---|---|
| aaa | cag | aca | aac | agt | gct | ctc | aaa | gaa | aaa | ctt | gat | ggt | gga | ata | gaa | 1104 |
| Lys | Gln | Thr | Asn | Ser | Ala | Leu | Lys | Glu | Lys | Leu | Asp | Gly | Gly | Ile | Glu |
| | 355 | | | | 360 | | | | 365 | | | | | | |

| cca | tat | cga | ctt | cca | gag | gtc | att | cag | aaa | tgt | aat | gca | cgt | tgg | act | 1152 |
| Pro | Tyr | Arg | Leu | Pro | Glu | Val | Ile | Gln | Lys | Cys | Asn | Ala | Arg | Trp | Thr |
| 370 | | | | 375 | | | | | 380 | | | | | | |

| aca | gaa | gag | cag | ctt | ctc | gcc | gta | caa | gcc | atc | agg | aaa | tat | ggc | cga | 1200 |
| Thr | Glu | Glu | Gln | Leu | Leu | Ala | Val | Gln | Ala | Ile | Arg | Lys | Tyr | Gly | Arg |
| 385 | | | | 390 | | | | | 395 | | | | | | 400 |

| gat | ttt | cag | gca | atc | tca | gac | gtg | att | ggg | aac | aaa | tca | gtg | gta | caa | 1248 |
| Asp | Phe | Gln | Ala | Ile | Ser | Asp | Val | Ile | Gly | Asn | Lys | Ser | Val | Val | Gln |
| | | | | 405 | | | | | 410 | | | | | 415 | |

| gtg | aaa | aac | ttt | ttt | gta | aat | tat | cga | cgc | cgc | ttc | aac | ata | gat | gaa | 1296 |
| Val | Lys | Asn | Phe | Phe | Val | Asn | Tyr | Arg | Arg | Arg | Phe | Asn | Ile | Asp | Glu |
| | | 420 | | | | | 425 | | | | | 430 | | | |

| gtt | tta | caa | gaa | tgg | gag | gca | gaa | cat | ggt | aaa | gaa | gag | acc | aat | ggg | 1344 |
| Val | Leu | Gln | Glu | Trp | Glu | Ala | Glu | His | Gly | Lys | Glu | Glu | Thr | Asn | Gly |
| | | | 435 | | | | | 440 | | | | | 445 | | |

| ccc | agt | aac | cag | aag | cct | gtg | aag | tcc | cca | gat | aat | tcc | att | aag | atg | 1392 |
| Pro | Ser | Asn | Gln | Lys | Pro | Val | Lys | Ser | Pro | Asp | Asn | Ser | Ile | Lys | Met |
| 450 | | | | | 455 | | | | | 460 | | | | | |

| ccc | gaa | gag | gaa | gac | gag | gct | cct | gtt | ctg | gat | gtc | aga | tat | gca | tct | 1440 |
| Pro | Glu | Glu | Glu | Asp | Glu | Ala | Pro | Val | Leu | Asp | Val | Arg | Tyr | Ala | Ser |
| 465 | | | | 470 | | | | | 475 | | | | | 480 | |

| gcc | tcc | tga | | | | | | | | | | | | | | 1449 |
| Ala | Ser | | | | | | | | | | | | | | |

<210> SEQ ID NO 33
<211> LENGTH: 482
<212> TYPE: PRT
<213> ORGANISM: Homo sapiens

<400> SEQUENCE: 33

Met Val Glu Lys Gly Pro Glu Val Ser Gly Lys Arg Arg Gly Arg Asn
1               5                   10                  15

Asn Ala Ala Ala Ser Ala Ser Ala Ala Ala Ser Ala Ala Ala Ser
            20                  25                  30

Ala Ala Cys Ala Ser Pro Ala Ala Thr Ala Ser Gly Ala Ala Ala
        35                  40                  45

Ser Ser Ala Ser Ala Ala Ala Ser Ala Ala Ala Ala Pro Asn Asn
    50                  55                  60

Gly Gln Asn Lys Ser Leu Ala Ala Ala Pro Asn Gly Asn Ser Ser
65                  70                  75                  80

Ser Asn Ser Trp Glu Glu Gly Ser Ser Gly Ser Ser Ser Asp Glu Glu
                85                  90                  95

His Gly Gly Gly Gly Met Arg Val Gly Pro Gln Tyr Gln Ala Val Val
            100                 105                 110

Pro Asp Phe Asp Pro Ala Lys Leu Ala Arg Arg Ser Gln Glu Arg Asp
        115                 120                 125

Asn Leu Gly Met Leu Val Trp Ser Pro Asn Gln Asn Leu Ser Glu Ala
    130                 135                 140

Lys Leu Asp Glu Tyr Ile Ala Ile Ala Lys Glu Lys His Gly Tyr Asn
145                 150                 155                 160

Met Glu Gln Ala Leu Gly Met Leu Phe Trp His Lys His Asn Ile Glu
                165                 170                 175

Lys Ser Leu Ala Asp Leu Pro Asn Phe Thr Pro Phe Pro Asp Glu Trp
            180                 185                 190

```
Thr Val Glu Asp Lys Val Leu Phe Glu Gln Ala Phe Ser Phe His Gly
            195                 200                 205

Lys Thr Phe His Arg Ile Gln Gln Met Leu Pro Asp Lys Ser Ile Ala
        210                 215                 220

Ser Leu Val Lys Phe Tyr Tyr Ser Trp Lys Lys Thr Arg Thr Lys Thr
225                 230                 235                 240

Ser Val Met Asp Arg His Ala Arg Lys Gln Lys Arg Glu Arg Glu Glu
                245                 250                 255

Ser Glu Asp Glu Leu Glu Glu Ala Asn Gly Asn Asn Pro Ile Asp Ile
                260                 265                 270

Glu Val Asp Gln Asn Lys Glu Ser Lys Lys Val Pro Pro Thr Glu
            275                 280                 285

Thr Val Pro Gln Val Lys Lys Glu Lys His Ser Thr Gln Ala Lys Asn
        290                 295                 300

Arg Ala Lys Arg Lys Pro Pro Lys Gly Met Phe Leu Ser Gln Glu Asp
305                 310                 315                 320

Val Glu Ala Val Ser Ala Asn Ala Thr Ala Ala Thr Thr Val Leu Arg
                325                 330                 335

Gln Leu Asp Met Glu Leu Val Ser Val Lys Arg Gln Ile Gln Asn Ile
            340                 345                 350

Lys Gln Thr Asn Ser Ala Leu Lys Glu Lys Leu Asp Gly Gly Ile Glu
        355                 360                 365

Pro Tyr Arg Leu Pro Glu Val Ile Gln Lys Cys Asn Ala Arg Trp Thr
    370                 375                 380

Thr Glu Glu Gln Leu Leu Ala Val Gln Ala Ile Arg Lys Tyr Gly Arg
385                 390                 395                 400

Asp Phe Gln Ala Ile Ser Asp Val Ile Gly Asn Lys Ser Val Val Gln
                405                 410                 415

Val Lys Asn Phe Phe Val Asn Tyr Arg Arg Arg Phe Asn Ile Asp Glu
            420                 425                 430

Val Leu Gln Glu Trp Glu Ala Glu His Gly Lys Glu Glu Thr Asn Gly
        435                 440                 445

Pro Ser Asn Gln Lys Pro Val Lys Ser Pro Asp Asn Ser Ile Lys Met
    450                 455                 460

Pro Glu Glu Glu Asp Glu Ala Pro Val Leu Asp Val Arg Tyr Ala Ser
465                 470                 475                 480

Ala Ser

<210> SEQ ID NO 34
<211> LENGTH: 3692
<212> TYPE: DNA
<213> ORGANISM: Homo sapiens
<220> FEATURE:
<221> NAME/KEY: CDS
<222> LOCATION: (386)..(2287)

<400> SEQUENCE: 34
ggtgaatggg ctggtggtgc tcgctgctgc tgctgagagg aggaggagga tgaagagttg      60
ggcttgtttg tctcctcctc ctcctgcttc ccctgctcag agttcctgcc tccagctgcc     120
aggggggaca gccagccagc agcaggaggg gggctagaga gctgaaggag agccagtttc     180
cccaaaattg gacttctcag aacctttaat atgctaatgt gcattgtgaa ctccaagag      240 ggggatatga tatgcagcat tcttgaatac ttctaatgac agggagccca ctacctcata     300
agctgcagtg agaagaggag tttgttactt taaacagagg ctgaagaaac tatagaatta     360
```

| | |
|---|---|
| gcagagaaag tggagaaggt agagg atg gag ttg cag act cta cag gag gct<br>                                      Met Glu Leu Gln Thr Leu Gln Glu Ala<br>                                       1               5 | 412 |
| ctt aaa gtg gaa att cag gtt cac cag aaa ctg gtt gct caa atg aag<br>Leu Lys Val Glu Ile Gln Val His Gln Lys Leu Val Ala Gln Met Lys<br> 10                    15                    20                    25 | 460 |
| cag gat cca cag aat gct gac tta aag aaa cag ctt cat gaa ctc caa<br>Gln Asp Pro Gln Asn Ala Asp Leu Lys Lys Gln Leu His Glu Leu Gln<br>              30                    35                    40 | 508 |
| gcc aaa atc aca gct ttg agt gag aaa cag aaa aga gta gtt gaa cag<br>Ala Lys Ile Thr Ala Leu Ser Glu Lys Gln Lys Arg Val Val Glu Gln<br>                  45                    50                    55 | 556 |
| cta cgg aag aac ctg ata gta aag caa gaa caa ccg gac aag ttc caa<br>Leu Arg Lys Asn Leu Ile Val Lys Gln Glu Gln Pro Asp Lys Phe Gln<br>       60                    65                    70 | 604 |
| ata cag cca ttg cca caa tct gaa aac aaa cta caa aca gca cag cag<br>Ile Gln Pro Leu Pro Gln Ser Glu Asn Lys Leu Gln Thr Ala Gln Gln<br> 75                    80                    85 | 652 |
| caa cca cta cag caa cta caa caa cag cag cag tac cac cac cac cac<br>Gln Pro Leu Gln Gln Leu Gln Gln Gln Gln Gln Tyr His His His His<br> 90                    95                  100             105 | 700 |
| gcc cag cag tca gct gca gcc tct ccc aac ctg act gct tca cag aag<br>Ala Gln Gln Ser Ala Ala Ala Ser Pro Asn Leu Thr Ala Ser Gln Lys<br>                  110                  115                120 | 748 |
| act gta act aca gct tct atg att acc aca aag aca cta cct ctc gtc<br>Thr Val Thr Thr Ala Ser Met Ile Thr Thr Lys Thr Leu Pro Leu Val<br>             125                    130                    135 | 796 |
| ttg aaa gca gca act gcg acc atg cct gcc tct gtg gtg ggc cag aga<br>Leu Lys Ala Ala Thr Ala Thr Met Pro Ala Ser Val Val Gly Gln Arg<br>        140                    145                    150 | 844 |
| cct acc att gct atg gtg acc gcc atc aac agt cag aag gct gtg ctc<br>Pro Thr Ile Ala Met Val Thr Ala Ile Asn Ser Gln Lys Ala Val Leu<br>             155                    160                    165 | 892 |
| agc act gat gtg cag aac aca cca gtc aac ctc cag acg tct agt aag<br>Ser Thr Asp Val Gln Asn Thr Pro Val Asn Leu Gln Thr Ser Ser Lys<br>170                   175                    180                    185 | 940 |
| gtc act ggg cct ggg gca gag gct gtc caa att gtg gca aaa aac aca<br>Val Thr Gly Pro Gly Ala Glu Ala Val Gln Ile Val Ala Lys Asn Thr<br>                  190                  195                200 | 988 |
| gtc act ctg cag gtt cag gca aca cct cct cag ccc atc aaa gta cca<br>Val Thr Leu Gln Val Gln Ala Thr Pro Pro Gln Pro Ile Lys Val Pro<br>             205                    210                    215 | 1036 |
| cag ttt atc ccc cct cct aga ctc act cca cgt cca aac ttt ctt cca<br>Gln Phe Ile Pro Pro Pro Arg Leu Thr Pro Arg Pro Asn Phe Leu Pro<br>        220                    225                    230 | 1084 |
| cag gtt cga ccc aag cct gtg gcc cag aat aac att cct att gcc cca<br>Gln Val Arg Pro Lys Pro Val Ala Gln Asn Asn Ile Pro Ile Ala Pro<br>            235                    240                    245 | 1132 |
| gca cca cct ccc atg ctc gca gct cct cag ctt atc cag agg ccc gtc<br>Ala Pro Pro Pro Met Leu Ala Ala Pro Gln Leu Ile Gln Arg Pro Val<br>250                   255                    260                    265 | 1180 |
| atg ctg acc aag ttc acc ccc aca acc ctt ccc aca tcc cag aat tcc<br>Met Leu Thr Lys Phe Thr Pro Thr Thr Leu Pro Thr Ser Gln Asn Ser<br>                  270                  275                280 | 1228 |
| atc cac ccc gtc cgt gtc gtc aat ggg cag act gca acc ata gcc aaa<br>Ile His Pro Val Arg Val Val Asn Gly Gln Thr Ala Thr Ile Ala Lys<br>             285                    290                    295 | 1276 |
| acg ttc ccc atg gcc cag ctc acc agc att gtg ata gct act cca ggg<br>Thr Phe Pro Met Ala Gln Leu Thr Ser Ile Val Ile Ala Thr Pro Gly<br>        300                    305                    310 | 1324 |

```
acc aga ctc gct gga cct caa act gta cag ctt agc aag cca agt ctt    1372
Thr Arg Leu Ala Gly Pro Gln Thr Val Gln Leu Ser Lys Pro Ser Leu
315                 320                 325 gaa aaa cag aca gtt aaa tct cac aca gaa aca gat gag aaa caa aca    1420
Glu Lys Gln Thr Val Lys Ser His Thr Glu Thr Asp Glu Lys Gln Thr
330                 335                 340                 345 gag agc cac acc atc acc cca cct gct gca ccc aaa cca aaa cgg gag    1468
Glu Ser His Thr Ile Thr Pro Pro Ala Ala Pro Lys Pro Lys Arg Glu
                350                 355                 360 gag aac cct cag aaa ctt gcc ttc atg gtg tct cta ggg ttg gta aca    1516
Glu Asn Pro Gln Lys Leu Ala Phe Met Val Ser Leu Gly Leu Val Thr
        365                 370                 375 cat gac cat cta gaa gaa atc caa agc aag agg caa gag cga aaa aga    1564
His Asp His Leu Glu Glu Ile Gln Ser Lys Arg Gln Glu Arg Lys Arg
            380                 385                 390 aga aca aca gca aat ccg gtc tac agt gga gca gtc ttt gag cca gag    1612
Arg Thr Thr Ala Asn Pro Val Tyr Ser Gly Ala Val Phe Glu Pro Glu
        395                 400                 405 cgt aag aag agt gca gtg aca tac cta aac agc aca atg cac cct ggg    1660
Arg Lys Lys Ser Ala Val Thr Tyr Leu Asn Ser Thr Met His Pro Gly
410                 415                 420                 425 acc cgg aag aga gcc aat gag gaa cac tgg cca aag ggt gat att cat    1708
Thr Arg Lys Arg Ala Asn Glu Glu His Trp Pro Lys Gly Asp Ile His
                430                 435                 440 gag gat ttt tgc agc gtt tgc aga aaa agt ggc cag tta ctg atg tgc    1756
Glu Asp Phe Cys Ser Val Cys Arg Lys Ser Gly Gln Leu Leu Met Cys
            445                 450                 455 gac acg tgt tcc cgt gta tat cat ttg gac tgc tta gac ccc cct ctg    1804
Asp Thr Cys Ser Arg Val Tyr His Leu Asp Cys Leu Asp Pro Pro Leu
        460                 465                 470 aaa aca att ccc aag ggc atg tgg atc tgt ccc aga tgt cag gac cag    1852
Lys Thr Ile Pro Lys Gly Met Trp Ile Cys Pro Arg Cys Gln Asp Gln
475                 480                 485 atg ctg aag aag gaa gaa gca att cca tgg cct gga act tta gca att    1900
Met Leu Lys Lys Glu Glu Ala Ile Pro Trp Pro Gly Thr Leu Ala Ile
490                 495                 500                 505 gtt cat tcc tat att gcc tac aaa gca gca aaa gaa gaa gag aaa cag    1948
Val His Ser Tyr Ile Ala Tyr Lys Ala Ala Lys Glu Glu Glu Lys Gln
                510                 515                 520 aag tta ctt aaa tgg agt tca gat tta aaa caa gaa cga gaa caa cta    1996
Lys Leu Leu Lys Trp Ser Ser Asp Leu Lys Gln Glu Arg Glu Gln Leu
            525                 530                 535 gag caa aag gtg aaa cag ctc agc aat tcc ata agt aaa tgc atg gaa    2044
Glu Gln Lys Val Lys Gln Leu Ser Asn Ser Ile Ser Lys Cys Met Glu
        540                 545                 550 atg aag aac acc atc ctg gcc cgg cag aag gag atg cac agc tcc ctg    2092
Met Lys Asn Thr Ile Leu Ala Arg Gln Lys Glu Met His Ser Ser Leu
555                 560                 565 gag aag gta aaa cag ctg att cgc ctc atc cac ggc atc gac ctc tcc    2140
Glu Lys Val Lys Gln Leu Ile Arg Leu Ile His Gly Ile Asp Leu Ser
570                 575                 580                 585 aaa cct gta gac tct gag gcc act gtg ggg gcc atc tcc aat ggc ccg    2188
Lys Pro Val Asp Ser Glu Ala Thr Val Gly Ala Ile Ser Asn Gly Pro
                590                 595                 600 gac tgc acc ccc cct gcc aat gcc gcc acc tcc acg ccg gcc cct tcc    2236
Asp Cys Thr Pro Pro Ala Asn Ala Ala Thr Ser Thr Pro Ala Pro Ser
            605                 610                 615 ccc tcc tcc cag agc tgc aca gcg aac tgt aac cag ggg gaa gag act    2284
Pro Ser Ser Gln Ser Cys Thr Ala Asn Cys Asn Gln Gly Glu Glu Thr
```

```
                  620         625         630
aaa taacagagcc cctctaggag aagccacggg atcccggcgg caaggagaac      2337
Lys agaacactga agactctaga aaagcaaagc cggatttctg gaaagtgcag aattcttttg 2397 gttctttggt tccagagaga gagaagatgc ttgtgccagg tggcaccaga gtttgccaat 2457 tgatccttct tattctgtgt gtacatgcaa agattggacc atgttacatg aaatagtgcc 2517 agctggaggt tctttgccag caccatgcca agtgaaataa tatatttact ctctctatta 2577 tacaccagtg tgtgcctgca gcagcctcca cagccacgat gggtttgttt ctgttttctt 2637 gggtggggag cagggacggg cggagggagg agagcaggtt tcagatcctt acttgccgag 2697 ccgtttgttt aggtagagaa gacaagtcca aagagtgtgt gggctttcct gtttctaaac 2757 tttcgctact ataaaaccaa aaaaaggaat tgagatttca ccaaccccag tgcccagaag 2817 agggaagggg agtggctgga gggagcaggg ggtgggacag tgtatcaaat aagcagtatt 2877 taatcacctc tggcgggggc ctcgtgcaag gggagactga caccaagaac agccagtagg 2937 ttcttctccc ctgcactctg ctccctgcgc ggtaacccca ccactcctga agcctgccca 2997 gtctccttcc ttccctgctt ggtgagtcgc gcatctccgt ggttatcccg ctgtctcctc 3057 tccaagaaca agcagagccc gggccactgg cccttgccca aggcagggaa gaaggatgtg 3117 tgtgtccagg aaggaaaaaa aggtggatca gtgattttac ttgaaaacaa gctccatccc 3177 ttttctatat ttataagaag agaagatctt gagtgaagca gcacgcgacc caggtgtgtg 3237 tgaattgaat ggagacgttt cttttctctt tctttaattt ttgttttgt tcttttttc  3297 tttaaggaaa gttttatttt actgttcatt ttactttctt ggtaacaaaa actaaaataa 3357 ggaatagaaa agctgttttt caggctgaca gtccaattaa gggtagccaa gaccttgcat 3417 ggtagagtag aatcatagt gtcagtgagg tcccgtgagt ctttgtgagt ccttgtgtca  3477
tcgttcgggc actgttttttt tatgcaaggg caaaaatctt tgtatctggg gaaaaaaaac 3537 ttttttttaa attaaaaagg aaaataaaag atattgaggt cttcctagtg ttacttaaat 3597 taagatcaag gtaagaaaca ttgtaaaaaa aaattacaaa agtgctattt gtttcctaaa 3657 aacagtgatt tctattaaaa aggtgtcaga actgg                          3692

<210> SEQ ID NO 35
<211> LENGTH: 634
<212> TYPE: PRT
<213> ORGANISM: Homo sapiens

<400> SEQUENCE: 35

Met Glu Leu Gln Thr Leu Gln Glu Ala Leu Lys Val Glu Ile Gln Val
 1               5                  10                  15

His Gln Lys Leu Val Ala Gln Met Lys Gln Asp Pro Gln Asn Ala Asp
                20                  25                  30

Leu Lys Lys Gln Leu His Glu Leu Gln Ala Lys Ile Thr Ala Leu Ser
            35                  40                  45

Glu Lys Gln Lys Arg Val Val Glu Gln Leu Arg Lys Asn Leu Ile Val
        50                  55                  60

Lys Gln Glu Gln Pro Asp Lys Phe Gln Ile Gln Pro Leu Pro Gln Ser
    65                  70                  75                  80

Glu Asn Lys Leu Gln Thr Ala Gln Gln Pro Leu Gln Gln Leu Gln
                85                  90                  95

Gln Gln Gln Gln Tyr His His His Ala Gln Ser Ala Ala Ala
               100                 105                 110
```

-continued

Ser Pro Asn Leu Thr Ala Ser Gln Lys Thr Val Thr Ala Ser Met
            115                 120                 125

Ile Thr Thr Lys Thr Leu Pro Leu Val Leu Lys Ala Ala Thr Ala Thr
130                 135                 140

Met Pro Ala Ser Val Val Gly Gln Arg Pro Thr Ile Ala Met Val Thr
145                 150                 155                 160

Ala Ile Asn Ser Gln Lys Ala Val Leu Ser Thr Asp Val Gln Asn Thr
                165                 170                 175

Pro Val Asn Leu Gln Thr Ser Ser Lys Val Thr Gly Pro Gly Ala Glu
            180                 185                 190

Ala Val Gln Ile Val Ala Lys Asn Thr Val Thr Leu Gln Val Gln Ala
        195                 200                 205

Thr Pro Pro Gln Pro Ile Lys Val Pro Gln Phe Ile Pro Pro Pro Arg
    210                 215                 220

Leu Thr Pro Arg Pro Asn Phe Leu Pro Gln Val Arg Pro Lys Pro Val
225                 230                 235                 240

Ala Gln Asn Asn Ile Pro Ile Ala Pro Ala Pro Pro Met Leu Ala
                245                 250                 255

Ala Pro Gln Leu Ile Gln Arg Pro Val Met Leu Thr Lys Phe Thr Pro
            260                 265                 270

Thr Thr Leu Pro Thr Ser Gln Asn Ser Ile His Pro Val Arg Val Val
        275                 280                 285

Asn Gly Gln Thr Ala Thr Ile Ala Lys Thr Phe Pro Met Ala Gln Leu
    290                 295                 300

Thr Ser Ile Val Ile Ala Thr Pro Gly Thr Arg Leu Ala Gly Pro Gln
305                 310                 315                 320

Thr Val Gln Leu Ser Lys Pro Ser Leu Glu Lys Gln Thr Val Lys Ser
                325                 330                 335

His Thr Glu Thr Asp Glu Lys Gln Thr Glu Ser His Thr Ile Thr Pro
            340                 345                 350

Pro Ala Ala Pro Lys Pro Lys Arg Glu Glu Asn Pro Gln Lys Leu Ala
        355                 360                 365

Phe Met Val Ser Leu Gly Leu Val Thr His Asp His Leu Glu Glu Ile
    370                 375                 380

Gln Ser Lys Arg Gln Glu Arg Lys Arg Arg Thr Thr Ala Asn Pro Val
385                 390                 395                 400

Tyr Ser Gly Ala Val Phe Glu Pro Glu Arg Lys Lys Ser Ala Val Thr
                405                 410                 415

Tyr Leu Asn Ser Thr Met His Pro Gly Thr Arg Lys Arg Ala Asn Glu
            420                 425                 430

Glu His Trp Pro Lys Gly Asp Ile His Glu Asp Phe Cys Ser Val Cys
        435                 440                 445

Arg Lys Ser Gly Gln Leu Leu Met Cys Asp Thr Cys Ser Arg Val Tyr
    450                 455                 460

His Leu Asp Cys Leu Asp Pro Pro Leu Lys Thr Ile Pro Lys Gly Met
465                 470                 475                 480

Trp Ile Cys Pro Arg Cys Gln Asp Gln Met Leu Lys Lys Glu Glu Ala
                485                 490                 495

Ile Pro Trp Pro Gly Thr Leu Ala Ile Val His Ser Tyr Ile Ala Tyr
            500                 505                 510

Lys Ala Ala Lys Glu Glu Glu Lys Gln Lys Leu Leu Lys Trp Ser Ser
        515                 520                 525

```
Asp Leu Lys Gln Glu Arg Glu Gln Leu Glu Gln Lys Val Lys Gln Leu
        530                 535                 540

Ser Asn Ser Ile Ser Lys Cys Met Glu Met Lys Asn Thr Ile Leu Ala
545                 550                 555                 560

Arg Gln Lys Glu Met His Ser Ser Leu Glu Lys Val Lys Gln Leu Ile
                565                 570                 575

Arg Leu Ile His Gly Ile Asp Leu Ser Lys Pro Val Asp Ser Glu Ala
            580                 585                 590

Thr Val Gly Ala Ile Ser Asn Gly Pro Asp Cys Thr Pro Pro Ala Asn
        595                 600                 605

Ala Ala Thr Ser Thr Pro Ala Pro Ser Pro Ser Gln Ser Cys Thr
    610                 615                 620

Ala Asn Cys Asn Gln Gly Glu Glu Thr Lys
625                 630

<210> SEQ ID NO 36
<211> LENGTH: 3811
<212> TYPE: DNA
<213> ORGANISM: Homo sapiens
<220> FEATURE:
<221> NAME/KEY: CDS
<222> LOCATION: (178)..(1947)

<400> SEQUENCE: 36
gcggccgaga agaggctggg gctcgcggcg cggctgcagc cgtcctgtgc gcgcggcgcg      60
cggctccgga gaggcgcccg cagtccaggg cggcgcgcac cgcctcgctg gcgctcagag     120
cggtgccttt tccccgagac tcccggcacc tcttcagcgc aaagattatt taatgta       177 atg gca act cca cgg ggg agg aca aag aaa aaa gca tct ttt gat cat      225
Met Ala Thr Pro Arg Gly Arg Thr Lys Lys Lys Ala Ser Phe Asp His
1               5                   10                  15 tct ccg gat agc ctt cct ttg agg agc tcc ggt agg cag gcg aag aag      273
Ser Pro Asp Ser Leu Pro Leu Arg Ser Ser Gly Arg Gln Ala Lys Lys
                20                  25                  30 aaa gca aca gag aca aca gat gag gat gaa gat ggt ggc tca gag aag      321
Lys Ala Thr Glu Thr Thr Asp Glu Asp Glu Asp Gly Gly Ser Glu Lys
            35                  40                  45 aag tac agg aaa tgt gaa aag gca ggc tgt acg gca aca tgt cct gtg      369
Lys Tyr Arg Lys Cys Glu Lys Ala Gly Cys Thr Ala Thr Cys Pro Val
        50                  55                  60 tgc ttt gca agt gct tct gaa aga tgt gcc aaa aat ggc tac acc tcc      417
Cys Phe Ala Ser Ala Ser Glu Arg Cys Ala Lys Asn Gly Tyr Thr Ser
65                  70                  75                  80 cga tgg tat cat ctc tcc tgt ggg gaa cat ttc tgt aat gaa tgc ttt      465
Arg Trp Tyr His Leu Ser Cys Gly Glu His Phe Cys Asn Glu Cys Phe
                85                  90                  95 gac cat tac tac aga agc cat aag gat gga tat gac aaa tat act aca      513
Asp His Tyr Tyr Arg Ser His Lys Asp Gly Tyr Asp Lys Tyr Thr Thr
                100                 105                 110 tgg aaa aaa ata tgg act agc aat ggc aaa acc gaa cct agt ccc aaa      561
Trp Lys Lys Ile Trp Thr Ser Asn Gly Lys Thr Glu Pro Ser Pro Lys
            115                 120                 125 gct ttc atg gca gac cag caa ctc ccc tac tgg gtt cag tgt aca aaa      609
Ala Phe Met Ala Asp Gln Gln Leu Pro Tyr Trp Val Gln Cys Thr Lys
        130                 135                 140 cct gag tgt aga aaa tgg agg cag ctt acc aag gaa atc cag ctt act      657
Pro Glu Cys Arg Lys Trp Arg Gln Leu Thr Lys Glu Ile Gln Leu Thr
145                 150                 155                 160 cca cag ata gcc aag act tat cga tgc ggt atg aaa cca aat act gct      705
```

```
Pro Gln Ile Ala Lys Thr Tyr Arg Cys Gly Met Lys Pro Asn Thr Ala
            165                 170                 175 att aag cct gag acc tca gat cat tgt tcc ctc cca gag gat cta gaa      753
Ile Lys Pro Glu Thr Ser Asp His Cys Ser Leu Pro Glu Asp Leu Glu
            180                 185                 190 gct ctt act cct cag aaa tgt att cct cac atc atc gtc cgg ggt ctc      801
Ala Leu Thr Pro Gln Lys Cys Ile Pro His Ile Ile Val Arg Gly Leu
            195                 200                 205 gtg cgt att cga tgc gtt cag gaa gtg gag aga ata ctg tat ttt atg      849
Val Arg Ile Arg Cys Val Gln Glu Val Glu Arg Ile Leu Tyr Phe Met
        210                 215                 220 acc aga aaa ggt ctc atc aac act gga gtt ctc agc gtg gga gcc gac      897
Thr Arg Lys Gly Leu Ile Asn Thr Gly Val Leu Ser Val Gly Ala Asp
225                 230                 235                 240 cag tat ctt ctc cct aag gac tac cac aat aaa tca gtc atc att atc      945
Gln Tyr Leu Leu Pro Lys Asp Tyr His Asn Lys Ser Val Ile Ile Ile
                245                 250                 255 ggg gct ggt cca gca gga tta gca gct gct agg caa ctg cat aac ttt      993
Gly Ala Gly Pro Ala Gly Leu Ala Ala Ala Arg Gln Leu His Asn Phe
            260                 265                 270 gga att aag gtg act gtc ctg gaa gcc aaa gac aga att gga ggc cga     1041
Gly Ile Lys Val Thr Val Leu Glu Ala Lys Asp Arg Ile Gly Gly Arg
            275                 280                 285 gtc tgg gat gat aaa tct ttt aaa ggc gtc aca gtg gga aga gga gct     1089
Val Trp Asp Asp Lys Ser Phe Lys Gly Val Thr Val Gly Arg Gly Ala
        290                 295                 300 cag att gtc aat ggg tgt att aac aac cca gta gca tta atg tgt gaa     1137
Gln Ile Val Asn Gly Cys Ile Asn Asn Pro Val Ala Leu Met Cys Glu
305                 310                 315                 320 caa gta tct gct cgc tcg tgg gac cac aat gaa ttc ttt gcc cag ttt     1185
Gln Val Ser Ala Arg Ser Trp Asp His Asn Glu Phe Phe Ala Gln Phe
                325                 330                 335 gct ggt gac cac act ctg cta act ccc ggg tac tcg gtg ata att gaa     1233
Ala Gly Asp His Thr Leu Leu Thr Pro Gly Tyr Ser Val Ile Ile Glu
            340                 345                 350 aaa ctg gca gaa ggg ctt gac att caa ctc aaa tct cca gtg cag tgt     1281
Lys Leu Ala Glu Gly Leu Asp Ile Gln Leu Lys Ser Pro Val Gln Cys
            355                 360                 365 att gat tat tct gga gat gaa gtg cag gtt acc act aca gat ggc aca     1329
Ile Asp Tyr Ser Gly Asp Glu Val Gln Val Thr Thr Thr Asp Gly Thr
        370                 375                 380 ggg tat tct gca caa aag gta tta gtc act gta cca ctg gct tta cta     1377
Gly Tyr Ser Ala Gln Lys Val Leu Val Thr Val Pro Leu Ala Leu Leu
385                 390                 395                 400 cag aaa ggt gcc att cag ttt aat cca ccg ttg tca gag aag aag atg     1425
Gln Lys Gly Ala Ile Gln Phe Asn Pro Pro Leu Ser Glu Lys Lys Met
                405                 410                 415 aag gct acc aac agc tta ggc gca ggc atc att gaa aag att gcc ttg     1473
Lys Ala Thr Asn Ser Leu Gly Ala Gly Ile Ile Glu Lys Ile Ala Leu
            420                 425                 430 caa ttt ccg tat aga ttt tgg gac agt aaa gta caa ggg gct gac ttt     1521
Gln Phe Pro Tyr Arg Phe Trp Asp Ser Lys Val Gln Gly Ala Asp Phe
            435                 440                 445 ttt ggt cac gtt cct ccc agt gcc agc aag cga ggg ctt ttt gcc gtg     1569
Phe Gly His Val Pro Pro Ser Ala Ser Lys Arg Gly Leu Phe Ala Val
        450                 455                 460 ttc tat gac atg gat ccc cag aag aag cac agc gtg ctg atg tct gtg     1617
Phe Tyr Asp Met Asp Pro Gln Lys Lys His Ser Val Leu Met Ser Val
465                 470                 475                 480
```

```
att gcc ggg gag gct gtc gca tcc gtg agg acc ctg gac gac aaa cag      1665
Ile Ala Gly Glu Ala Val Ala Ser Val Arg Thr Leu Asp Asp Lys Gln
            485                 490                 495 gtg ctg cag cag tgc atg gcc acg ctc cgg gag ctg ttc aag gag cag      1713
Val Leu Gln Gln Cys Met Ala Thr Leu Arg Glu Leu Phe Lys Glu Gln
            500                 505                 510 gag gtc cca gat ccc aca aag tat ttt gtc act cgg tgg agc aca gac      1761
Glu Val Pro Asp Pro Thr Lys Tyr Phe Val Thr Arg Trp Ser Thr Asp
            515                 520                 525 cca tgg atc cag atg gca tac agt ttt gtg aag aca ggt gga agt ggg      1809
Pro Trp Ile Gln Met Ala Tyr Ser Phe Val Lys Thr Gly Gly Ser Gly
            530                 535                 540 gag gcc tac gat atc att gct gaa gac att caa gga acc gtc ttt ttc      1857
Glu Ala Tyr Asp Ile Ile Ala Glu Asp Ile Gln Gly Thr Val Phe Phe
545                 550                 555                 560 gct ggt gag gca aca aac agg cat ttc cca caa act gtt aca ggg gca      1905
Ala Gly Glu Ala Thr Asn Arg His Phe Pro Gln Thr Val Thr Gly Ala
                565                 570                 575 tat ttg agt ggc gtt cga gaa gca agc aag att gca gca ttt                1947
Tyr Leu Ser Gly Val Arg Glu Ala Ser Lys Ile Ala Ala Phe
            580                 585                 590 taagaattcg gtggacccag ctttcttctg tacccccagat ggggaaattt gaatcacatg     2007
ttaaacctca gttttataag aggggggaaaa aaccgtctct acatagtaaa actgaaatgt     2067
ttctaaggcg atatgataat gcaaacctat ttcatcactc taaaagcact gacctcaaaa     2127
aaccttataa gcacttagat ttaattgcat tttccatagg ttcaactact gctgaaagtc     2187
tggatttcag aataaagcag aatgtaagtt tcagttgagg ccatggattt gattgttcca     2247
tggctggaag ttcccttag atttcacatt ttatatggct gatcaatttt catacattga      2307
gaaaccaagt caatcaagca ggaatcattt aaaaaccaga taaagccatg ttttcttct      2367
gtgacaattt atcagtatct ttaccaatga gccttaattt ttatataggt ccaatattga     2427
gcttttactt aaaatttaga tagaaccttt ttttggatac agcacaaact ccagttgaca     2487
gtaaaatgaa gcttctaggt atttgtatt gtacatattt cctcctactg ggtgttcaaa      2547
agaaatttaa attcaagtac cttttgtgat aaaatgtttt agatttgtgc acccattggc     2607
aaaacaggaa agtttccaga taggtattgt atcattgaga atgcagcaca gatagtgtgg     2667
gcttcacact atagacacag aatatagctt tttcttaaag ccaaatttgg gtgataggac     2727
actttaaata tccttaattt tggcaaccac tagcaaaaaa acttgtcaga ataatttaac     2787
caagcccctc tccacttctt ttatttaaaa gcactgattc aattgctagg aatatttttg     2847
cagatttttc tttacagtat tccataggca ggtccactgg aaaactgcag aaaaatgtga     2907
gctctcctgg taaatagtat acattttata agctatattt taaaggccta agaacatggc     2967
aagtatttac ttttatcttt ttttaaaaa cactcatgac agaaaacagt ttaataatat      3027
ctcattctaa aataaaacac tggttgcagg gtcttcagga tgcctatttt gccaagaaac     3087
ttcagtatac aggttagaaa tatgcttttg ttttttgaaca ataatatact ggtttgcttt    3147
aaagaaggga ctaaatatga ctttaaagag acttcaaaat attgagtatt ttaaaaattt     3207
aaaagtaggt cagtttataa cgagtaaata cctaacacac caagaatgtg cagtgaacct     3267
caggcattta agacacctcc cccaccgccc gcccccgcc ccccccaatc aaagtgtggt      3327
cccaaaacaa gccaacagct gtatatctca aaagttaacc caagacaact ctgatattta     3387
ggttattgt tgagactcat tggtactgac tggcaagtat tctgctttaa agtatcatgt     3447
attaaaatgt ttagacagca tgtgttttaa agtgataaat gcaaaatgtt aagtttgaaa     3507
```

```
tggttaacag taaattatta tgttagtttc caggcacttg aactgtgcta caagtagggg    3567
aaaacctact ttaaagtatg gtaaatgtgt gttttaaact tcctatcaag tgacatactt    3627
catttgattt tttgtttaag aagccatggt acttttttct tgagttactt tggatatgtt    3687
ttttcaatgc catctgaaga ttttgtaatt gagtagcagt aaatatacag atttacaatg    3747
ttttaactac agttcatgaa tagctggttg tgtaaaacta ataaaaaact agactttcac    3807
atgt                                                                  3811
```

```
<210> SEQ ID NO 37
<211> LENGTH: 590
<212> TYPE: PRT
<213> ORGANISM: Homo sapiens

<400> SEQUENCE: 37

Met Ala Thr Pro Arg Gly Arg Thr Lys Lys Ala Ser Phe Asp His
 1               5                  10                  15

Ser Pro Asp Ser Leu Pro Leu Arg Ser Ser Gly Arg Gln Ala Lys Lys
                20                  25                  30

Lys Ala Thr Glu Thr Thr Asp Glu Asp Glu Asp Gly Gly Ser Glu Lys
            35                  40                  45

Lys Tyr Arg Lys Cys Glu Lys Ala Gly Cys Thr Ala Thr Cys Pro Val
        50                  55                  60

Cys Phe Ala Ser Ala Ser Glu Arg Cys Ala Lys Asn Gly Tyr Thr Ser
    65                  70                  75                  80

Arg Trp Tyr His Leu Ser Cys Gly Glu His Phe Cys Asn Glu Cys Phe
                85                  90                  95

Asp His Tyr Tyr Arg Ser His Lys Asp Gly Tyr Asp Lys Tyr Thr Thr
            100                 105                 110

Trp Lys Lys Ile Trp Thr Ser Asn Gly Lys Thr Glu Pro Ser Pro Lys
        115                 120                 125

Ala Phe Met Ala Asp Gln Gln Leu Pro Tyr Trp Val Gln Cys Thr Lys
    130                 135                 140

Pro Glu Cys Arg Lys Trp Arg Gln Leu Thr Lys Glu Ile Gln Leu Thr
145                 150                 155                 160

Pro Gln Ile Ala Lys Thr Tyr Arg Cys Gly Met Lys Pro Asn Thr Ala
                165                 170                 175

Ile Lys Pro Glu Thr Ser Asp His Cys Ser Leu Pro Glu Asp Leu Glu
            180                 185                 190

Ala Leu Thr Pro Gln Lys Cys Ile Pro His Ile Ile Val Arg Gly Leu
        195                 200                 205

Val Arg Ile Arg Cys Val Gln Glu Val Glu Arg Ile Leu Tyr Phe Met
    210                 215                 220

Thr Arg Lys Gly Leu Ile Asn Thr Gly Val Leu Ser Val Gly Ala Asp
225                 230                 235                 240

Gln Tyr Leu Leu Pro Lys Asp Tyr His Asn Lys Ser Val Ile Ile Ile
                245                 250                 255

Gly Ala Gly Pro Ala Gly Leu Ala Ala Ala Arg Gln Leu His Asn Phe
            260                 265                 270

Gly Ile Lys Val Thr Val Leu Glu Ala Lys Asp Arg Ile Gly Gly Arg
        275                 280                 285

Val Trp Asp Asp Lys Ser Phe Lys Gly Val Thr Val Gly Arg Gly Ala
    290                 295                 300

Gln Ile Val Asn Gly Cys Ile Asn Asn Pro Val Ala Leu Met Cys Glu
```

```
            305                 310                 315                 320
    Gln Val Ser Ala Arg Ser Trp Asp His Asn Glu Phe Phe Ala Gln Phe
                    325                 330                 335

Ala Gly Asp His Thr Leu Leu Thr Pro Gly Tyr Ser Val Ile Ile Glu
                340                 345                 350

Lys Leu Ala Glu Gly Leu Asp Ile Gln Leu Lys Ser Pro Val Gln Cys
            355                 360                 365

Ile Asp Tyr Ser Gly Asp Glu Val Gln Val Thr Thr Thr Asp Gly Thr
        370                 375                 380

Gly Tyr Ser Ala Gln Lys Val Leu Val Thr Val Pro Leu Ala Leu Leu
    385                 390                 395                 400

Gln Lys Gly Ala Ile Gln Phe Asn Pro Pro Leu Ser Glu Lys Lys Met
                    405                 410                 415

Lys Ala Thr Asn Ser Leu Gly Ala Gly Ile Ile Glu Lys Ile Ala Leu
                420                 425                 430

Gln Phe Pro Tyr Arg Phe Trp Asp Ser Lys Val Gln Gly Ala Asp Phe
            435                 440                 445

Phe Gly His Val Pro Pro Ser Ala Ser Lys Arg Gly Leu Phe Ala Val
        450                 455                 460

Phe Tyr Asp Met Asp Pro Gln Lys Lys His Ser Val Leu Met Ser Val
    465                 470                 475                 480

Ile Ala Gly Glu Ala Val Ala Ser Val Arg Thr Leu Asp Asp Lys Gln
                    485                 490                 495

Val Leu Gln Gln Cys Met Ala Thr Leu Arg Glu Leu Phe Lys Glu Gln
                500                 505                 510

Glu Val Pro Asp Pro Thr Lys Tyr Phe Val Thr Arg Trp Ser Thr Asp
            515                 520                 525

Pro Trp Ile Gln Met Ala Tyr Ser Phe Val Lys Thr Gly Gly Ser Gly
        530                 535                 540

Glu Ala Tyr Asp Ile Ile Ala Glu Asp Ile Gln Gly Thr Val Phe Phe
    545                 550                 555                 560

Ala Gly Glu Ala Thr Asn Arg His Phe Pro Gln Thr Val Thr Gly Ala
                    565                 570                 575

Tyr Leu Ser Gly Val Arg Glu Ala Ser Lys Ile Ala Ala Phe
                580                 585                 590

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atgtcaaaga tgagcagatt                                                  20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggcgaaggta gagtacagag a                                                21
```

```
<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccatggttgt aacaggtctt                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gacaatcttg gcatgttggt                                               20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggacctcaaa ctgtacagct t                                             21

<210> SEQ ID NO 43
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Val Ile Ile Ile Gly Ser Gly Val Ser Gly Leu Ala Ala Ala Arg
 1               5                  10                  15

Gln Leu Gln Ser Phe Gly Met Asp Val Thr Leu Leu Glu Ala Arg Asp
            20                  25                  30

Arg Val Gly Gly Arg Val Ala Thr Phe Arg Lys Gly Asn Tyr Val Ala
        35                  40                  45

Asp Leu Gly Ala Met Val Val Thr Gly Leu Gly Gly
    50                  55                  60

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cccgaattca tggtggagaa gggcccgag t                                   31

<210> SEQ ID NO 45
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 45
cccctcgagt caggaggcag atgcatatct                                        30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cccctcgagg acctgaggaa ctgtctcagt                                        30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cccgaattca ctgagacagt tcctcaggtc                                        30

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cccgaattca gggtcggacc ccagtacca                                         29

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cccctcgagc caacgtgcat tacatttctg a                                      31

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 50

His His His His His His
  1               5
```